United States Patent [19]
Lasky et al.

[11] Patent Number: 6,040,437
[45] Date of Patent: Mar. 21, 2000

[54] TYROSINE PHOSPHORYLATED CLEAVAGE FURROW-ASSOCIATED PROTEINS (PSTPIPS)

[75] Inventors: Laurence A. Lasky, Sausalito; Donald J. Dowbenko, San Bruno, both of Calif.

[73] Assignee: Genentech, Inc., So. San Francisco, Calif.

[21] Appl. No.: 08/938,830

[22] Filed: Sep. 29, 1997

Related U.S. Application Data

[60] Provisional application No. 60/104,590, Feb. 7, 1997.

[51] Int. Cl.$^7$ .................................................. C07H 21/02
[52] U.S. Cl. .................... 536/23.1; 536/23.5; 435/320.1; 435/69.1
[58] Field of Search .................................. 536/23.1, 23.5, 536/23.2; 435/320.1, 69.1, 69.2

[56] References Cited

PUBLICATIONS

Marra et al, Database Genbank, subsection EST Accession No. AA038079, Aug. 1996.

Kitts, Database EMBL, Accession No. U13188, Mar. 1996.

Aoki et al., "The novel protein–tyrosine phosphatase PTP20 is a positive regulator of PC12 cell neuronal differentiation" *Journal of Biological Chemistry* 271(46):29422–29426 (1996).

Astier et al., "The related adhesion focal tyrosine kinase is tyrosine–phosphorylated after β1–integrin stimulation in B cells and binds to p130cas" *Journal of Biological Chemistry* 272(1):228–232 (1997).

Charest et al., "Phosphotyrosine–independent binding of SHC to the NPLH sequence of murine protein–tyrosine phosphatase–PEST" *Journal of Biological Chemistry* 271(14):8424–8429 (1996).

Cheng et al., "A novel protein tyrosine phosphatase expressed in lin lo CD34 hi Sca hi hematopoietic progenitor cells" *Blood* 88(4):1156–1167 (1996).

Cloutier et al., "Association of inhibitory tyrosine protein kinase p50csk with protein tyrosine phosphatase PEP in T cells and other hemopoietic cells" *EMBO Journal* 15(18):4909–4918 (1996).

Dixon, J., "Protein Tyrosine Phosphatases: their roles in single transduction" *Recent Prog. Hom. Res.* 51:405–414 (1996).

Dosil et al., "Cloning and characterization of fetal liver phosphatase 1, a nuclear protein tyrosine phosphatase isolated from hematopoietic stem cells" *Blood* 88(12):4510–4525 (1996).

Fantl et al., "Signalling by Receptor Tyrosine Kinases" *Annual Review in Biochemistry* 62:453–481 (1993).

Garton et al., "Identification of p130cas as a substrate for the cytosolic protein tyrosine phosphatase PTP–PEST" *Molecular & Cellular Biology* 16(11):6408–6418 (1996).

Huang et al., "Cloning and characterization of PTK–K1, a novel nonreceptor protein tyrosine phosphatase highly expressed in bone marrow" *Oncogene* 13:1567–1573 (1996).

Hunter *1001 Protein Kinases Redux toward 2000* 5:367–376 (1994).

Kim et al., "Characterization of the PEST family protein tyrosine phosphatase BDP1" *Oncogene* 13:2275–2279 (1996).

Matthews et al., "Characterization of hematopoietic intracellular protein tyrosine phosphatases: description of a phosphatase containing an SH2 domain and another enriched in proline–, glutamic acid–, serine–, and threonine–rich sequences" *Molecular and Cellular Biology* 12(5):2396–2405 (1992).

Petch et al., "Adhesion–induced tyrosine phosphorylation of the p130 SRC substrate" *J. Cell. Sci.* 108:1371–1379 (1995).

Tonks, N., "Introduction: Protein tyrosine phosphatases" *Semin. Cell Biol.* 4:373–377 (1993).

Yang et al., "Cloning and expression of PTP–Pest. A novel, human, nontransmembrane protein tyrosine phosphatase" *Journal of Biological Chemistry* 268(23):17650 (1993).

Campbell, A., "General Properties and applications of monoclonal antibodies" *Monoclonal Antibody Technology*, The Netherlands:Elsevier Science Publishers B.V., Chapter 1, pp. 1–32 (1984).

Chevray et al., "Protein interaction cloning in yeast: identification of mammalian proteins that react with the Leucine Zipper of Jun" *Proc. Natl. Acad. Sci. USA* 89:5789–5793 (1992).

Chien et al., "The Two–Hybrid System: A method to identify and clone genes for proteins that interact with a protein of interest" *Proc. Natl. Acad. Sci. USA* 88:9578–9582 (1991).

Fankhauser et al., "The S. pombe cdc15 Gene Is a Key Element in the Reorganization of F–Actin at Mitosis" *Cell* 82:435–444 (1995).

Fields and Song, "A novel genetic system to detect protein––protein interactions" *Nature* 340:245–246 (1989).

Spencer et al., "PSTPIP: a tyrosine phosphorylated cleavage furrow–associated protein that is a substrate for a PEST tyrosine phosphatase" *Journal of Cell Biology* 138(4):845–860 (Aug. 25, 1997).

Wu et al., "Tyrosine Phosphorylation Regulates the SH3–mediated Binding of the Wiskott–Aldrich Syndrome Protein to PSTPIP, a Cytoskeletal–associated Protein" *Journal of Biological Chemistry* 273(10):5765–5770 (Mar. 6, 1998).

*Primary Examiner*—Sheela Huff
*Attorney, Agent, or Firm*—Mark T. Kresnak

[57] ABSTRACT

This invention concerns new PSTPIP polypeptides which are bound by and dephosphorylated by the PEST family of protein tyrosine phosphatases. The invention specifically concerns native murine PSTPIP polypeptides and their homologues in other mammals, and their functional derivatives. The invention further relates to nucleic acids encoding these proteins, vectors containing and capable of expressing such nucleic acid, and recombinant host cells transformed with such nucleic acid. Methods for inducing the polymerization of actin monomers in eukaryotic cells and assays for identifying antagonists and agonists of the PSTPIP polypeptides of the present invention are also provided.

10 Claims, 14 Drawing Sheets

FIG. 1A-1

```
cdc15    437  TKDNDDIILSSQLQPTATGSRSSRLSFSRHGHGSQTSLGSIKRKSIMERM
cdc15    487  GRPTSPFMGSSFSNMGSRSTSPTKEGFASNQHATGASVQSDELEDIDPRA
cdc15    537  NVVLNVGPNMLSVGEAPVESTSKEEDKDVPDPIANAMAELSSSMRRQST
cdc15    587  SVDDEAPVSLSKTSSSTRLNGLGYHSRNTSIASDIDGVPKKSTLGAPPAA
cdc15    637  HTSAQMQRMSNSFASQTKQVFGEQRTENSARESLRHSRSNMSRSPSPMLS
cdc15    687  RRSSTLRPSFERSASSLSVRQSDVVSPAPSTRARGQSVSGQQRPSSSMSL PSTPIP   289  · · · · · · · · · · · · · · · · · · · · · · · · · DREVTPLIGS
cdc15    737  YGEYNKSQPQLSMQRSVSPNPLGPNRRSSSVLQSQKSTSSNTSNRNNGGY PSTPIP   299  PSIQPSCGVIKRFSGLLHGSPKTTPSAPAASTETLTPTPERNELVYASIE
cdc15    787  SGSRPSSEMGHRY-GSMSGRSMRQVSQRSTSRARSPEPTNRNSVQSKNVD
                                         *                    *
                                            SH3 domain PSTPIP   349  VQATQGNLNSSAQDY-RALYDYTAQNSDELDISAGDILAVILEGEDGWWT
cdc15    836  PRATFTAEGEPILGYVIALYDYQAQIPEEISFQKGDTLMVLRTQEDGWWD PSTPIP   398  VE----RNGQRGFVPGSYLEKL
cdc15    886  GEIINVPNSKRGLFPSNFVQTV
```

FIG. 1A-2

```
3 pstpip.sh3    1 L Y D Y T A Q N S D E L D I S A G D I L A V L E G E D G W W T V E R N G Q R G F V P G S Y L E K L
4 myosin.sh3    1 L Y Q Y I G Q D V D E L S F N V N E V I E I L I E D S S G W W K G R L H G Q E G L F P G N Y V E K I
5 spectrin.sh3  1 L Y D Y Q E K S P R E V T M K K G D I L T L L N S T N K D W W K V E V N D R Q G F V P A A Y V K K L
6 fodrin.sh3    1 L Y D Y Q E K S P R E V T M K K G D I L T L L N S T N K D W W K V E V N D R Q G F V P A A Y V K K L
7 hsp.sh3       1 L Y D Y Q G E G S D E L S F D P D D I I T D I E M V D E G W W R G Q C R G H F G L F P A N Y V K K L
8 cortactin.sh3 1 L Y D Y Q A A G D D E I S F D P D D I I T N I E M I D D G W W R G V C K G R Y G L F P A N Y V E -
```

FIG. 1B

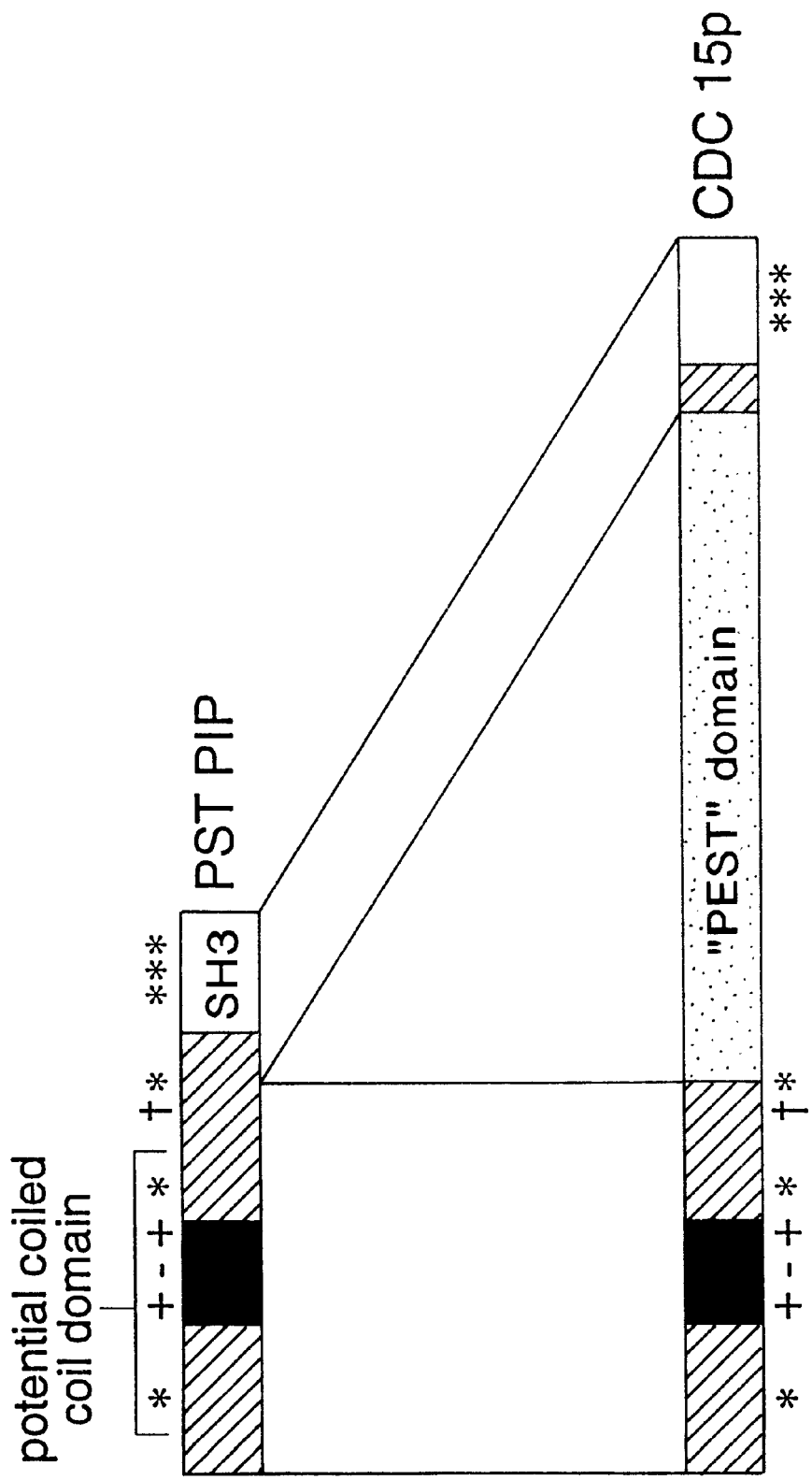

|         |   |   |   |   |   |   |   |   |
|---------|---|---|---|---|---|---|---|---|
| PSTPIP  | + | + | + | + | + | + | + | + |
| V-SRC   | − | + | − | + | − | + | − | + |
| wt HSCF | − | − | − | − | − | − | + | + |
| C-S HSCF| − | − | + | + | − | − | − | − |
| D-A HSCF| − | − | − | − | + | + | − | − |
FIG. 6B
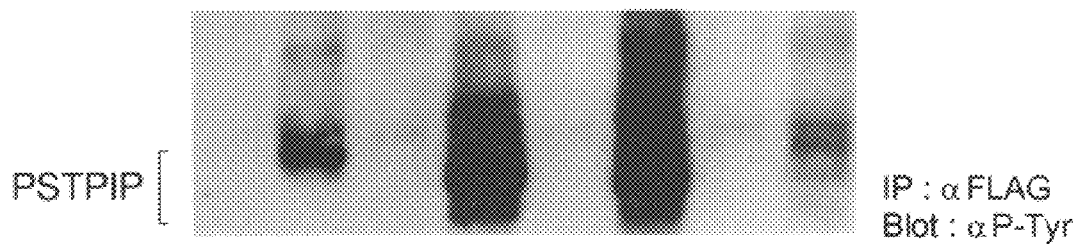
FIG. 6C
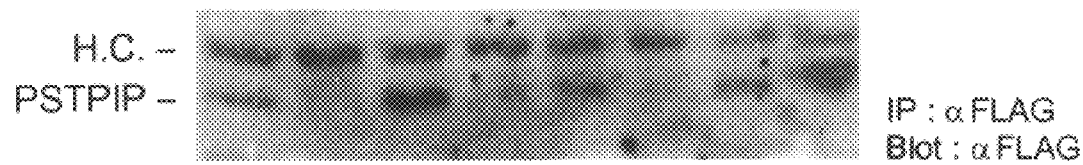
FIG. 6D
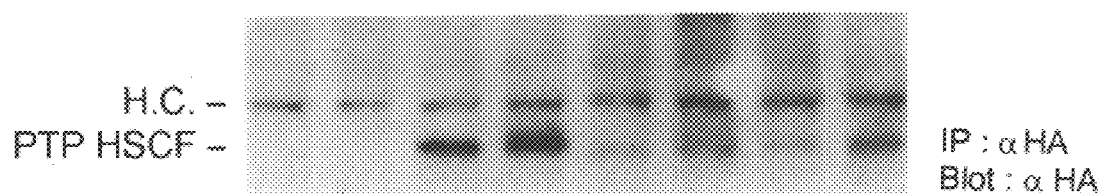
FIG. 6E

| DA HSCF | + | − | + | − |
| wt HSCF | − | + | − | + |
| PSTPIP | − | − | + | + |

PTP HSCF →

IP : αFLAG
Blot : αHA

PTP HSCF →

IP : αHA
Blot : αHA

PSTPIP →

IP : αFLAG
Blot : αFLAG

PSTPIP →

IP : αHA
Blot : αFLAG

SEQUENCE LISTING (1) GENERAL INFORMATION:

(iii) NUMBER OF SEQUENCES: 73

(2) INFORMATION FOR SEQ ID NO:1:

(i) SEQUENCE CHARACTERISTICS:
      (A) LENGTH: 415 amino acids
      (B) TYPE: Amino Acid
      (D) TOPOLOGY: Linear (xi) SEQUENCE DESCRIPTION: SEQ ID NO:1:

```
Met Met Ala Gln Leu Gln Phe Arg Asp Ala Phe Trp Cys Arg Asp
 1               5                  10                  15

Phe Thr Ala His Thr Gly Tyr Glu Val Leu Leu Gln Arg Leu Leu
                20                  25                  30

Asp Gly Arg Lys Met Cys Lys Asp Val Glu Glu Leu Leu Arg Gln
                35                  40                  45

Arg Ala Gln Ala Glu Glu Arg Tyr Gly Lys Glu Leu Val Gln Ile
                50                  55                  60

Ala Arg Lys Ala Gly Gly Gln Thr Glu Met Asn Ser Leu Arg Thr
                65                  70                  75

Ser Phe Asp Ser Leu Lys Gln Thr Glu Asn Val Gly Ser Ala
                80                  85                  90

His Ile Gln Leu Ala Leu Ala Leu Arg Glu Glu Leu Arg Ser Leu
                95                 100                 105

Glu Glu Phe Arg Glu Arg Gln Lys Glu Gln Arg Lys Lys Tyr Glu
               110                 115                 120

Ala Ile Met Asp Arg Val Gln Lys Ser Lys Leu Ser Leu Tyr Lys
               125                 130                 135

Lys Thr Met Glu Ser Lys Lys Ala Tyr Asp Gln Lys Cys Arg Asp
               140                 145                 150

Ala Asp Asp Ala Glu Gln Ala Phe Glu Arg Val Ser Ala Asn Gly
               155                 160                 165

His Gln Lys Gln Val Glu Lys Ser Gln Asn Lys Ala Lys Gln Cys
               170                 175                 180

Lys Glu Ser Ala Thr Glu Ala Glu Arg Val Tyr Arg Gln Asn Ile
               185                 190                 195

Glu Gln Leu Glu Arg Ala Arg Thr Glu Trp Glu Gln Glu His Arg
               200                 205                 210

Thr Thr Cys Glu Ala Phe Gln Leu Gln Glu Phe Asp Arg Leu Thr
               215                 220                 225

Ile Leu Arg Asn Ala Leu Trp Val His Cys Asn Gln Leu Ser Met
               230                 235                 240

Gln Cys Val Lys Asp Asp Glu Leu Tyr Glu Glu Val Arg Leu Thr
               245                 250                 255

Leu Glu Gly Cys Asp Val Glu Gly Asp Ile Asn Gly Phe Ile Gln
               260                 265                 270

Ser Lys Ser Thr Gly Arg Glu Pro Pro Ala Pro Val Pro Tyr Gln
               275                 280                 285

Asn Tyr Tyr Asp Arg Glu Val Thr Pro Leu Ile Gly Ser Pro Ser
               290                 295                 300

Ile Gln Pro Ser Cys Gly Val Ile Lys Arg Phe Ser Gly Leu Leu
               305                 310                 315

His Gly Ser Pro Lys Thr Thr Pro Ser Ala Pro Ala Ala Ser Thr
               320                 325                 330

Glu Thr Leu Thr Pro Thr Pro Glu Arg Asn Glu Leu Val Tyr Ala
               335                 340                 345

Ser Ile Glu Val Gln Ala Thr Gln Gly Asn Leu Asn Ser Ser Ala
               350                 355                 360

Gln Asp Tyr Arg Ala Leu Tyr Asp Tyr Thr Ala Gln Asn Ser Asp
               365                 370                 375

Glu Leu Asp Ile Ser Ala Gly Asp Ile Leu Ala Val Ile Leu Glu
```

-continued

```
                380              385              390
Gly Glu Asp Gly Trp Trp Thr Val Glu Arg Asn Gly Gln Arg Gly
                    395              400              405

Phe Val Pro Gly Ser Tyr Leu Glu Lys Leu
                    410              415
```

(2) INFORMATION FOR SEQ ID NO:2:

(i) SEQUENCE CHARACTERISTICS:
        (A) LENGTH: 2100 base pairs
        (B) TYPE: Nucleic Acid
        (C) STRANDEDNESS: Single
        (D) TOPOLOGY: Linear (xi) SEQUENCE DESCRIPTION: SEQ ID NO:2:

| | | | | |
|---|---|---|---|---|
| CAATATTTCA | AGCTATACCA | AGCATACAAT | CAACTCCAAG | CTTATGCCCA | 50 |
| AGAAGAAGCG | GAAGGTCTCG | AGCGGCGCCA | ATTTTAATCA | AAGTGGGAAT | 100 |
| ATTGCTGATA | GCTCATTGTC | CTTCACTTTC | ACTAACAGTA | GCAACGGTCC | 150 |
| GAACCTCATA | ACAACTCAAA | CAAATTCTCA | AGCGCTTTCA | CAACCAATTG | 200 |
| CCTCCTCTAA | CGTTCATGAT | AACTTCATGA | ATAATGAAAT | CACGGCTAGT | 250 |
| AAAATTGATG | ATGGTAATAA | TTCAAAACCA | CTGTCACCTG | GTTGGACGGA | 300 |
| CCAAACTGCG | TATAACGCGT | TTGGAATCAC | TACAGGGATG | TTTAATACCA | 350 |
| CTACAATGGA | TGATGTATAT | AACTATCTAT | TCGATGATGA | AGATACCCCA | 400 |
| CCAAACCCAA | AAAAAGAGGG | TGGGTCGACC | CACGCGTCCG | GCTCCTTCCT | 450 |
| CATTTCGCTG | CTGATTCTAG | CCCCAAACAA | AACAGGTTGA | GCCTTTTTCC | 500 |
| TCCTCCGGCA | GTTGCCTCTG | GCTTGTGGCT | GCCTTCTGAG | CGTTTCAGAC | 550 |
| GGCGCCGGCT | GGGAGTGGGA | GGGAGGGCCT | GGGCTAGCCG | CGCTGGGACT | 600 |
| GGGACGTGCT | CCTGGCTCCT | GGCCCATGCT | CAGCCCTGCT | TGAAGCAGGA | 650 |
| GTGCTAGCAT | TTGACACAAC | GCCCTTGGAG | GATGATGGCC | CAGCTGCAGT | 700 |
| TCCGAGATGC | CTTCTGGTGC | AGGGACTTCA | CGGCCCACAC | AGGGTATGAG | 750 |
| GTGCTACTGC | AGAGGCTGCT | GGACGGCAGG | AAGATGTGCA | AGGATGTGGA | 800 |
| GGAGCTGCTC | AGACAGAGGG | CCCAGGCGGA | GGAGAGGTAC | GGGAAGGAGC | 850 |
| TGGTGCAGAT | TGCACGCAAG | GCTGGTGGCC | AGACAGAGAT | GAATTCCCTG | 900 |
| AGGACCTCCT | TTGACTCCCT | GAAGCAGCAA | ACAGAGAATG | TGGGCAGTGC | 950 |
| ACACATCCAG | CTGGCCCTGG | CCCTGCGTGA | GGAGCTGCGG | AGCCTGGAGG | 1000 |
| AGTTCCGAGA | GAGACAGAAA | GAGCAGCGGA | AGAAGTATGA | GGCCATCATG | 1050 |
| GACCGTGTCC | AGAAGAGCAA | GTTGTCGCTC | TACAAGAAGA | CCATGGAGTC | 1100 |
| CAAGAAGGCA | TATGACCAGA | AGTGCAGGGA | TGCAGATGAT | GCTGAGCAGG | 1150 |
| CCTTCGAGCG | TGTGAGTGCC | AATGGCCACC | AGAAGCAAGT | AGAAAAGAGC | 1200 |
| CAGAACAAAG | CCAAGCAGTG | CAAGGAGTCA | GCCACAGAGG | CAGAAAGAGT | 1250 |
| GTACAGGCAA | AATATCGAAC | AACTGGAGAG | AGCGAGGACC | GAGTGGGAGC | 1300 |
| AGGAGCACCG | GACTACCTGT | GAGGCCTTCC | AGTTGCAGGA | GTTTGACCGG | 1350 |
| CTCACCATCC | TCCGCAATGC | CCTGTGGGTG | CACTGTAACC | AGCTCTCCAT | 1400 |
| GCAGTGTGTC | AAGGATGATG | AGCTCTATGA | GGAAGTGCGG | CTGACCCTTG | 1450 |
| AGGGCTGTGA | TGTGGAAGGT | GACATCAATG | GCTTCATCCA | GTCCAAGAGC | 1500 |

```
ACTGGCAGAG AGCCCCCAGC TCCGGTGCCT TATCAGAACT ACTATGACAG        1550

GGAGGTGACC CCACTGATTG GCAGCCCTAG CATCCAGCCC TCCTGCGGTG        1600

TGATAAAGAG GTTCTCTGGG CTGCTACATG GAAGTCCCAA GACCACACCT        1650

TCTGCTCCTG CTGCTTCCAC AGAGACTCTG ACTCCCACCC CTGAGCGGAA        1700

TGAGTTGGTC TACGCATCCA TCGAAGTGCA GGCGACCCAG GGAAACCTTA        1750

ACTCATCAGC CCAGGACTAC CGGGCACTCT ACGACTACAC TGCACAGAAT        1800

TCTGATGAGC TGGACATTTC CGCGGGAGAC ATCCTGGCGG TCATCCTGGA        1850

AGGGGAGGAT GGCTGGTGGA CTGTGGAGCG GAACGGACAA CGTGGCTTTG        1900

TCCCTGGGTC GTACTTGGAG AAGCTCTGAG GAAAGGCTAG CAGTCTCCAC        1950

ATACCTCCGC CCTGACTGTG AGGTCAGGAC TGTTTCTTTC CATCACCGCC        2000

CAGGCCTCAC GGGGCCAGAA CCAAGCCCGG TGGTGCTGGG CATGGGCTGG        2050

GTGCTGGCTA CTCTCAATAA ATGTCTCCCA GAAGGAAAAA AAAAAAAAAA        2100
```

(2) INFORMATION FOR SEQ ID NO:3:

(i) SEQUENCE CHARACTERISTICS:
        (A) LENGTH: 48 amino acids
        (B) TYPE: Amino Acid
        (D) TOPOLOGY: Linear (xi) SEQUENCE DESCRIPTION: SEQ ID NO:3:

```
Leu Tyr Asp Tyr Thr Ala Gln Asn Ser Asp Glu Leu Asp Ile Ser
 1               5                  10                  15

Ala Gly Asp Ile Leu Ala Val Ile Leu Xaa Gly Glu Asp Gly Trp
                20                  25                  30

Trp Thr Val Glu Arg Asn Gly Gln Arg Gly Phe Val Pro Gly Ser
                35                  40                  45

Tyr Leu Arg
        48
```

(2) INFORMATION FOR SEQ ID NO:4:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO:4:

```
Leu Tyr Gln Tyr Ile Gly Gln Asp Val Asp Glu Leu Ser Phe Asn
 1               5                  10                  15

Val Asn Glu Val Ile Glu Ile Leu Ile Glu Asp Ser Ser Gly Trp
                20                  25                  30

Trp Lys Gly Arg Leu His Gly Gln Glu Gly Leu Phe Pro Gly Asn
                35                  40                  45

Tyr Val Glu Lys Ile
            50
```

(2) INFORMATION FOR SEQ ID NO:5:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO:5:

Leu Tyr Asp Tyr Gln Glu Lys Ser Pro Arg Glu Val Thr Met Lys

```
                    1               5                  10                 15
Lys Gly Asp Ile Leu Thr Leu Leu Asn Ser Thr Asn Lys Asp Trp
                        20                25                 30
Trp Lys Val Glu Val Asn Asp Arg Gln Gly Phe Val Pro Ala Ala
                        35                40                 45
Tyr Val Lys Lys Leu
                50

(2) INFORMATION FOR SEQ ID NO:6:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO:6:

Leu Tyr Asp Tyr Gln Gly Glu Gly Ser Asp Glu Leu Ser Phe Asp
 1               5                  10                 15
Pro Asp Asp Ile Ile Thr Asp Ile Glu Met Val Asp Glu Gly Trp
                        20                25                 30
Trp Arg Gly Gln Cys Arg Gly His Phe Gly Leu Phe Pro Ala Asn
                        35                40                 45
Tyr Val Lys Leu Leu
                50

(2) INFORMATION FOR SEQ ID NO:7:

(i) SEQUENCE CHARACTERISTICS:
        (A) LENGTH: 48 amino acids
        (B) TYPE: Amino Acid
        (D) TOPOLOGY: Linear (xi) SEQUENCE DESCRIPTION: SEQ ID NO:7:

Leu Tyr Asp Tyr Gln Ala Ala Gly Asp Asp Glu Ile Ser Phe Asp
 1               5                  10                 15
Pro Asp Asp Ile Ile Thr Asn Ile Glu Met Ile Asp Asp Gly Trp
                        20                25                 30
Trp Arg Gly Val Cys Lys Gly Arg Tyr Gly Leu Phe Pro Ala Asn
                        35                40                 45
Tyr Val Glu
        48

(2) INFORMATION FOR SEQ ID NO:8:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:8:

Asp Tyr Lys Asp Asp Asp Asp Lys
 1               5           8

(2) INFORMATION FOR SEQ ID NO:9:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO:9:
```

```
CGCGGATCCA CCATGATGGC CCAGCTGCAG TTC                              33
```

(2) INFORMATION FOR SEQ ID NO:10:

(i) SEQUENCE CHARACTERISTICS:
        (A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO:10:

```
GTACGCGTCG ACTCACTTGT CATCGTCGTC CTTGTAGTCG AGCTT                 45
```

(2) INFORMATION FOR SEQ ID NO:11:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:11:

```
TGCCTTTCTC TCCACAGG                                               18
```

(2) INFORMATION FOR SEQ ID NO:12:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO:12:

```
CTCCTTGAGG TTCTACTAGT GGGGGCTGGT GTCCTG                           36
```

(2) INFORMATION FOR SEQ ID NO:13:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO:13:

```
GCGGCCGCAC TAGTATCCAG TCTGTGCTCC ATCTGTTAC                        39
```

(2) INFORMATION FOR SEQ ID NO:14:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (xi) SEQUENCE DESCRIPTION: SEQ ID NO:14:

```
GCGTTTGGAA TCACTAC                                                17
```

(2) INFORMATION FOR SEQ ID NO:15:

(i) SEQUENCE CHARACTERISTICS:
        (A) LENGTH: 41 base pairs
        (B) TYPE: Nucleic Acid
        (C) STRANDEDNESS: Single
        (D) TOPOLOGY: Linear (xi) SEQUENCE DESCRIPTION: SEQ ID NO:15:

```
TTATAGTTTA GCGGCCGCTC ACCGGTAGTC CTGGGCTGAT G                     41
```

(2) INFORMATION FOR SEQ ID NO:16:

(i) SEQUENCE CHARACTERISTICS:
        (A) LENGTH: 37 base pairs
        (B) TYPE: Nucleic Acid
        (C) STRANDEDNESS: Single
        (D) TOPOLOGY: Linear (xi) SEQUENCE DESCRIPTION: SEQ ID NO:16:

GTACGCGTCG ACCGCACTCT ACGACTACAC TGCACAG                    37

(2) INFORMATION FOR SEQ ID NO:17:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (xi) SEQUENCE DESCRIPTION: SEQ ID NO:17:

CTCTGGCGAA GAAGTCC                                              17

(2) INFORMATION FOR SEQ ID NO:18:

(i) SEQUENCE CHARACTERISTICS:
        (A) LENGTH: 32 base pairs
        (B) TYPE: Nucleic Acid
        (C) STRANDEDNESS: Single
        (D) TOPOLOGY: Linear (xi) SEQUENCE DESCRIPTION: SEQ ID NO:18:

GATCGAATTC CCAGAACCTC AAGGAGAACT GC                         32

(2) INFORMATION FOR SEQ ID NO:19:

(i) SEQUENCE CHARACTERISTICS:
        (A) LENGTH: 38 base pairs
        (B) TYPE: Nucleic Acid
        (C) STRANDEDNESS: Single
        (D) TOPOLOGY: Linear (xi) SEQUENCE DESCRIPTION: SEQ ID NO:19:

GATCCTCGAG TTACACCCGT GTCCACTCTG CTGGAGGA                   38

(2) INFORMATION FOR SEQ ID NO:20:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO:20:

Gly Phe Asn Leu Arg Ile Gly Arg Pro Lys Gly Pro Arg Asp Pro
 1          5                10              15

Pro Ala Glu Trp Thr
           20

(2) INFORMATION FOR SEQ ID NO:21:

(i) SEQUENCE CHARACTERISTICS:
        (A) LENGTH: 19 amino acids
        (B) TYPE: Amino Acid
        (D) TOPOLOGY: Linear (xi) SEQUENCE DESCRIPTION: SEQ ID NO:21:

−continued

```
Gly Phe Gly Asn Arg Phe Ser Lys Pro Lys Gly Pro Arg Asn Pro
1               5                   10                  15

Pro Ser Ala Trp
            19
```

(2) INFORMATION FOR SEQ ID NO:22:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO:22:

```
Gly Phe Gly Asn Arg Cys Gly Lys Pro Lys Gly Pro Arg Asp Pro
1               5                   10                  15

Pro Ser Glu Trp Thr
                20
```

(2) INFORMATION FOR SEQ ID NO:23:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO:23:

```
Gly Gly Val Leu Arg Ser Ile Ser Val Pro Ala Pro Pro Thr Leu
1               5                   10                  15

Pro Met Ala Asp Thr
                20
```

(2) INFORMATION FOR SEQ ID NO:24:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO:24:

```
GTATATGTCC TGGCCAGCCC ATGGGGTTCC CAGCAG                          36
```

(2) INFORMATION FOR SEQ ID NO:25:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO:25:

```
GCAGGTCGAC TCTAGATTAC ACCCGTGTCC ACTCTG                          36
```

(2) INFORMATION FOR SEQ ID NO:26:

(i) SEQUENCE CHARACTERISTICS:
        (A) LENGTH: 907 amino acids
        (B) TYPE: Amino Acid
        (D) TOPOLOGY: Linear (xi) SEQUENCE DESCRIPTION: SEQ ID NO:26:

```
Met Leu Thr Lys Ser Leu Gln Gly Ser Glu Asp Ala Gly Met Asp
1               5                   10                  15

Ala Leu Met Ser Arg Thr Lys Ser Ser Leu Ser Val Leu Glu Ser
                20                  25                  30
```

-continued

```
Ile Asp Glu Phe Tyr Ala Lys Arg Ala Ser Ile Glu Arg Glu Tyr
                 35                  40                  45

Ala Ser Lys Leu Gln Glu Leu Ala Ala Ser Ala Asp Ile Pro
         50                  55                  60

Glu Val Gly Ser Thr Leu Asn Asn Ile Leu Ser Met Arg Thr Glu
             65                  70                  75

Thr Gly Ser Met Ala Lys Ala His Glu Glu Val Ser Gln Gln Ile
                 80                  85                  90

Asn Thr Glu Leu Arg Asn Lys Ile Arg Glu Tyr Ile Asp Gln Thr
                 95                 100                 105

Glu Gln Gln Lys Val Val Ala Ala Asn Ala Ile Glu Glu Leu Tyr
                110                 115                 120

Gln Lys Lys Thr Ala Leu Glu Ile Asp Leu Ser Glu Lys Lys Asp
                125                 130                 135

Ala Tyr Glu Tyr Ser Cys Asn Lys Leu Asn Ser Tyr Met Arg Gln
                140                 145                 150

Thr Lys Lys Met Thr Gly Arg Glu Leu Asp Lys Tyr Asn Leu Lys
                155                 160                 165

Ile Arg Gln Ala Ala Leu Ala Val Lys Lys Met Asp Ala Glu Tyr
                170                 175                 180

Arg Glu Thr Asn Glu Leu Leu Leu Thr Val Thr Arg Glu Trp Ile
                185                 190                 195

Asp Arg Trp Thr Glu Val Cys Asp Ala Phe Gln His Ile Glu Glu
                200                 205                 210

Tyr Arg Leu Glu Phe Leu Lys Thr Asn Met Trp Ala Tyr Ala Asn
                215                 220                 225

Ile Ile Ser Thr Ala Cys Val Lys Asp Asp Glu Ser Cys Glu Lys
                230                 235                 240

Ile Arg Leu Thr Leu Glu Asn Thr Asn Ile Asp Glu Asp Ile Thr
                245                 250                 255

Gln Met Ile Gln Asn Glu Gly Thr Gly Thr Thr Ile Pro Pro Leu
                260                 265                 270

Pro Glu Phe Asn Asp Tyr Phe Lys Glu Asn Gly Leu Asn Tyr Asp
                275                 280                 285

Ile Asp Gln Leu Ile Ser Lys Ala Pro Ser Tyr Pro Tyr Ser Ser
                290                 295                 300

Ser Arg Pro Ser Ala Ser Ala Ser Leu Ala Ser Ser Pro Thr Arg
                305                 310                 315

Ser Ala Phe Arg Pro Lys Thr Ser Glu Thr Val Ser Ser Glu Val
                320                 325                 330

Val Ser Ser Pro Pro Thr Ser Pro Leu His Ser Pro Val Lys Pro
                335                 340                 345

Val Ser Asn Glu Gln Val Glu Gln Val Thr Glu Val Glu Leu Ser
                350                 355                 360

Ile Pro Val Pro Ser Ile Gln Glu Ala Glu Ser Gln Lys Pro Val
                365                 370                 375

Leu Thr Gly Ser Ser Met Arg Arg Pro Ser Val Thr Ser Pro Thr
                380                 385                 390

Phe Glu Val Ala Ala Arg Pro Leu Thr Ser Met Asp Val Arg Ser
                395                 400                 405

Ser His Asn Ala Glu Thr Glu Val Gln Ala Ile Pro Ala Ala Thr
                410                 415                 420
```

-continued

```
Asp Ile Ser Pro Glu Val Lys Glu Gly Lys Asn Ser Glu Asn Ala
            425                 430                 435

Ile Thr Lys Asp Asn Asp Asp Ile Ile Leu Ser Ser Gln Leu Gln
            440                 445                 450

Pro Thr Ala Thr Gly Ser Arg Ser Ser Arg Leu Ser Phe Ser Arg
            455                 460                 465

His Gly His Gly Ser Gln Thr Ser Leu Gly Ser Ile Lys Arg Lys
            470                 475                 480

Ser Ile Met Glu Arg Met Gly Arg Pro Thr Ser Pro Phe Met Gly
            485                 490                 495

Ser Ser Phe Ser Asn Met Gly Ser Arg Ser Thr Ser Pro Thr Lys
            500                 505                 510

Glu Gly Phe Ala Ser Asn Gln His Ala Thr Gly Ala Ser Val Gln
            515                 520                 525

Ser Asp Glu Leu Glu Asp Ile Asp Pro Arg Ala Asn Val Val Leu
            530                 535                 540

Asn Val Gly Pro Asn Met Leu Ser Val Gly Glu Ala Pro Val Glu
            545                 550                 555

Ser Thr Ser Lys Glu Glu Asp Lys Asp Val Pro Asp Pro Ile Ala
            560                 565                 570

Asn Ala Met Ala Glu Leu Ser Ser Ser Met Arg Arg Arg Gln Ser
            575                 580                 585

Thr Ser Val Asp Asp Glu Ala Pro Val Ser Leu Ser Lys Thr Ser
            590                 595                 600

Ser Ser Thr Arg Leu Asn Gly Leu Gly Tyr His Ser Arg Asn Thr
            605                 610                 615

Ser Ile Ala Ser Asp Ile Asp Gly Val Pro Lys Lys Ser Thr Leu
            620                 625                 630

Gly Ala Pro Pro Ala Ala His Thr Ser Ala Gln Met Gln Arg Met
            635                 640                 645

Ser Asn Ser Phe Ala Ser Gln Thr Lys Gln Val Phe Gly Glu Gln
            650                 655                 660

Arg Thr Glu Asn Ser Ala Arg Glu Ser Leu Arg His Ser Arg Ser
            665                 670                 675

Asn Met Ser Arg Ser Pro Ser Pro Met Leu Ser Arg Arg Ser Ser
            680                 685                 690

Thr Leu Arg Pro Ser Phe Glu Arg Ser Ala Ser Ser Leu Ser Val
            695                 700                 705

Arg Gln Ser Asp Val Val Ser Pro Ala Pro Ser Thr Arg Ala Arg
            710                 715                 720

Gly Gln Ser Val Ser Gly Gln Gln Arg Pro Ser Ser Ser Met Ser
            725                 730                 735

Leu Tyr Gly Glu Tyr Asn Lys Ser Gln Pro Gln Leu Ser Met Gln
            740                 745                 750

Arg Ser Val Ser Pro Asn Pro Leu Gly Pro Asn Arg Arg Ser Ser
            755                 760                 765

Ser Val Leu Gln Ser Gln Lys Ser Thr Ser Ser Asn Thr Ser Asn
            770                 775                 780

Arg Asn Asn Gly Gly Tyr Ser Gly Ser Arg Pro Ser Ser Glu Met
            785                 790                 795

Gly His Arg Tyr Gly Ser Met Ser Gly Arg Ser Met Arg Gln Val
            800                 805                 810

Ser Gln Arg Ser Thr Ser Arg Ala Arg Ser Pro Glu Pro Thr Asn
```

```
                  815                 820                 825
Arg Asn Ser Val Gln Ser Lys Asn Val Asp Pro Arg Ala Thr Phe
              830                 835                 840
Thr Ala Glu Gly Glu Pro Ile Leu Gly Tyr Val Ile Ala Leu Tyr
              845                 850                 855
Asp Tyr Gln Ala Gln Ile Pro Glu Glu Ile Ser Phe Gln Lys Gly
              860                 865                 870
Asp Thr Leu Met Val Leu Arg Thr Gln Glu Asp Gly Trp Trp Asp
              875                 880                 885
Gly Glu Ile Ile Asn Val Pro Asn Ser Lys Arg Gly Leu Phe Pro
              890                 895                 900
Ser Asn Phe Val Gln Thr Val
              905     907

(2) INFORMATION FOR SEQ ID NO:27:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:27:

Pro Xaa Xaa Pro
 1           4

(2) INFORMATION FOR SEQ ID NO:28:

(i) SEQUENCE CHARACTERISTICS:
        (A) LENGTH: 1613 base pairs
        (B) TYPE: Nucleic Acid
        (C) STRANDEDNESS: Single
        (D) TOPOLOGY: Linear (xi) SEQUENCE DESCRIPTION: SEQ ID NO:28:

ACGATCACTA TAGGGCGAAT TGGGCCTCTA GATGCATGCT CGAGCGGCCG           50

CCAGTGTGAT GGATATCTGC AGAATTCGGC TTCCATCCTA ATACGACTCA          100

CTATAGGGCT CGAGCGGCCG CCCGGGCAGG TCTAGAATTC AGCGGCCGCT          150

GAATTCTCTT TTTCCTCCCC TCAGAAGCTC CTCTCTGGCT CGTGGCTGCC          200

TTCTGAGTGT TGCAGACGGC GCCGGCCGGG AAGGGGGGCC TGGGCCAGCC          250

CTGCCAGGAC TGGGACGCTG CTGCTGACGC CTGGCCCTCC ATCAGGCCAG          300

CCTGTGGCAG GAGAGTGAGC TTTGCCGCGG CAGACGCCTG AGGATGATGC          350

CCCAGCTGCA GTTCAAAGAT GCCTTTTGGT GCAGGGACTT CACAGCCCAC          400

ACGGGCTACG AGGTGCTGCT GCAGCGGCTT CTGGATGGCA GGAAGATGTG          450

CAAAGACATG GAGGAGCTAC TGAGGCAGAG GGCCCAGGCG GAGGAGCGGT          500

ACGGGAAGGA GCTGGTGCAG ATCGCACGGA AGGCAGGTGG CCAGACGGAG          550

ATCAACTCCC TGAGGGCCTC CTTTGACTCC TTGAAGCAGC AAATGGAGAA          600

TGTGGGCAGC TCACACATCC AGCTGGCCCT GACCCTGCGT GAGGAGCTGC          650

GGAGTCTCGA GGAGTTTCGT GAGAGGCAGA AGGAGCAGAG GAAGAAGGGC          700

ATGGCTGTCC CGAGACAGAG TGACTGCATG GAAGTGAAGT CCCCATCATG          750

GGAGTATGAG GCCGTCATGG ACCGGGTCCA GAAGAGCAAG CTGTCGCTCT          800

ACAAGAAGGC CATGGAGTCC AAGAAGACAT ACGAGCAGAA GTGCCGGGAC          850

GCGGACGACG CGGAGCAGGC CTTCGAGCGC ATTAGCGCCA ACGGCCACCA          900
```

```
GAAGCAGGTG GAGAAGAGTC AGAACAAAGC CAGGCAGTGC AAGGACTCGG          950

CCACCGAGGC AGAGCGGGTA TACAGGCAGA GCATTGCGCA GCTGGAGAAG         1000

GTCCGGGCTG AGTGGGAGCA GGAGCACCGG ACCACCTGTG AGGCCTTTCA         1050

GCTGCAAGAG TTTGACCGGC TGACCATTCT CCGCAACGCC CTGTGGGTGC         1100

ACAGTAACCA GCTCTCCATG CAGTGTGTCA AGGATGATGA GCTCTACGAG         1150

GAAGTGCGGC TGACGCTGGA AGGCTGCAGC ATAGACGCCG ACATCGACAG         1200

TTTCATCCAG GCCAAGAGCA CGGGCACAGA GCCCCCCAGG TTCTCTGGAC         1250

TGCTGCACGG AAGTCCCAAG ACCACTTCGT CAGCTTCTGC TGGCTCCACA         1300

GAGACCCTGA CCCCCACCCC CGAGCGGAAT GAGGGTGTCT ACACAGCCAT         1350

CGCAGTGCAG GAGATACAGG GAAACCCGGC CTCACCAGCC CAGGACTACC         1400

GGGCGCTCTA CGATTATACA GCGCAGAACC CAGATGAGCT GGACCTGTCC         1450

GCGGGAGACA TCCTGGAAGG GGAGGATGGC TGGTGGACTG TGGAGAGGAA         1500

CGGGCAGCGT GGCTTCGTCC CTGGTTCCTA CCTGGAGAAG CTTTGAGGGA         1550

AGGCCAGGAG CCCCTTCGGA CCTCCGCCCT GCCAGTGGAG CCAGCAGTGC         1600

CCCCAGCACT GTC                                                 1613

(2) INFORMATION FOR SEQ ID NO:29:

(i) SEQUENCE CHARACTERISTICS:
        (A) LENGTH: 400 amino acids
        (B) TYPE: Amino Acid
        (D) TOPOLOGY: Linear (xi) SEQUENCE DESCRIPTION: SEQ ID NO:29:

Met Met Pro Gln Leu Gln Phe Lys Asp Ala Phe Trp Cys Arg Asp
 1               5                  10                  15

Phe Thr Ala His Thr Gly Tyr Glu Val Leu Leu Gln Arg Leu Leu
                20                  25                  30

Asp Gly Arg Lys Met Cys Lys Asp Met Glu Glu Leu Leu Arg Gln
                35                  40                  45

Arg Ala Gln Ala Glu Glu Arg Tyr Gly Lys Glu Leu Val Gln Ile
                50                  55                  60

Ala Arg Lys Ala Gly Gly Gln Thr Glu Ile Asn Ser Leu Arg Ala
                65                  70                  75

Ser Phe Asp Ser Leu Lys Gln Gln Met Glu Asn Val Gly Ser Ser
                80                  85                  90

His Ile Gln Leu Ala Leu Thr Leu Arg Glu Glu Leu Arg Ser Leu
                95                 100                 105

Glu Glu Phe Arg Glu Arg Gln Lys Glu Gln Arg Lys Lys Gly Met
               110                 115                 120

Ala Val Pro Arg Gln Ser Asp Cys Met Glu Val Lys Ser Pro Ser
               125                 130                 135

Trp Glu Tyr Glu Ala Val Met Asp Arg Val Gln Lys Ser Lys Leu
               140                 145                 150

Ser Leu Tyr Lys Lys Ala Met Glu Ser Lys Lys Thr Tyr Glu Gln
               155                 160                 165

Lys Cys Arg Asp Ala Asp Asp Ala Glu Gln Ala Phe Glu Arg Ile
               170                 175                 180

Ser Ala Asn Gly His Gln Lys Gln Val Glu Lys Ser Gln Asn Lys
               185                 190                 195
```

```
Ala Arg Gln Cys Lys Asp Ser Ala Thr Glu Ala Glu Arg Val Tyr
            200                 205                 210

Arg Gln Ser Ile Ala Gln Leu Glu Lys Val Arg Ala Glu Trp Glu
            215                 220                 225

Gln Glu His Arg Thr Thr Cys Glu Ala Phe Gln Leu Gln Glu Phe
            230                 235                 240

Asp Arg Leu Thr Ile Leu Arg Asn Ala Leu Trp Val His Ser Asn
            245                 250                 255

Gln Leu Ser Met Gln Cys Val Lys Asp Asp Glu Leu Tyr Glu Glu
            260                 265                 270

Val Arg Leu Thr Leu Glu Gly Cys Ser Ile Asp Ala Asp Ile Asp
            275                 280                 285

Ser Phe Ile Gln Ala Lys Ser Thr Gly Thr Glu Pro Pro Arg Phe
            290                 295                 300

Ser Gly Leu Leu His Gly Ser Pro Lys Thr Thr Ser Ser Ala Ser
            305                 310                 315

Ala Gly Ser Thr Glu Thr Leu Thr Pro Thr Pro Glu Arg Asn Glu
            320                 325                 330

Gly Val Tyr Thr Ala Ile Ala Val Gln Glu Ile Gln Gly Asn Pro
            335                 340                 345

Ala Ser Pro Ala Gln Asp Tyr Arg Ala Leu Tyr Asp Tyr Thr Ala
            350                 355                 360

Gln Asn Pro Asp Glu Leu Asp Leu Ser Ala Gly Asp Ile Leu Glu
            365                 370                 375

Gly Glu Asp Gly Trp Trp Thr Val Glu Arg Asn Gly Gln Arg Gly
            380                 385                 390

Phe Val Pro Gly Ser Tyr Leu Glu Lys Leu
            395                 400

(2) INFORMATION FOR SEQ ID NO:30:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO:30:

CAGTTCGGAT CCATGATGCT GCAGAGGCTG CTGGACGGCA GG                              42

(2) INFORMATION FOR SEQ ID NO:31:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO:31:

CAGTTCGGAT CCATGATGGA GAGGTACGGG AAGGAGCTGG TG                              42

(2) INFORMATION FOR SEQ ID NO:32:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO:32:
```

CAGTTCGGAT CCATGATGTC CTTTGACTCC CTGAAGCAGC AA                    42

(2) INFORMATION FOR SEQ ID NO:33:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO:33:

CAGTTCGGAT CCATGATGGA GCTGCGGAGC CTGGAGGAGT TC                    42

(2) INFORMATION FOR SEQ ID NO:34:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO:34:

CAGTTCGGAT CCATGATGGT CCAGAAGAGC AAGTTGTCGC TC                    42

(2) INFORMATION FOR SEQ ID NO:35:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO:35:

CAGTTCGGAT CCATGATGGC AGATGATGCT GAGCAGGCCT TC                    42

(2) INFORMATION FOR SEQ ID NO:36:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO:36:

ACGTCACTCG AGTCACTTGT CATCGTCGTC CTT                              33

(2) INFORMATION FOR SEQ ID NO:37:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO:37:

TTGACCTCGA GTCATCACCG CTCAGGGGTG GGAGTCAGAG TC                    42

(2) INFORMATION FOR SEQ ID NO:38:

(i) SEQUENCE CHARACTERISTICS:
        (A) LENGTH: 40 base pairs
        (B) TYPE: Nucleic Acid
        (C) STRANDEDNESS: Single
        (D) TOPOLOGY: Linear (xi) SEQUENCE DESCRIPTION: SEQ ID NO:38:

```
TTGACCTCGA GTCATCACAG CCCAGAGAAC CTCTTTATCA                              40
```

(2) INFORMATION FOR SEQ ID NO:39:

(i) SEQUENCE CHARACTERISTICS:
        (A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO:39:

```
TTGACCTCGA GTCATCAGTC ATAGTAGTTC TGATAAGGCA CCGGA                        45
```

(2) INFORMATION FOR SEQ ID NO:40:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO:40:

```
TTGACCTCGA GTCATCAGTC ACCTTCCACA TCACAGCCCT CAAGGGTC                     48
```

(2) INFORMATION FOR SEQ ID NO:41:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO:41:

```
TTGACCTCGA GTCATCAGGA GAGCTGGTTA CAGTGCACCC ACAGGGCA                     48
```

(2) INFORMATION FOR SEQ ID NO:42:

(i) SEQUENCE CHARACTERISTICS:
        (A) LENGTH: 47 base pairs
        (B) TYPE: Nucleic Acid
        (C) STRANDEDNESS: Single
        (D) TOPOLOGY: Linear (xi) SEQUENCE DESCRIPTION: SEQ ID NO:42:

```
TTGACCTCGA GTCATCACTC ACGCAGGGCC AGGGCCAGCT GGATGTG                      47
```

(2) INFORMATION FOR SEQ ID NO:43:

(i) SEQUENCE CHARACTERISTICS:
        (A) LENGTH: 29 base pairs
        (B) TYPE: Nucleic Acid
        (C) STRANDEDNESS: Single
        (D) TOPOLOGY: Linear (xi) SEQUENCE DESCRIPTION: SEQ ID NO:43:

```
GTCTGAGGAG CTCCGCCGCA GCCTTGCAC                                          29
```

(2) INFORMATION FOR SEQ ID NO:44:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO:44:

```
CCTTCCCGTA CGCCGCCGCC GCCTGAGCTC TCTG                                    34
```

(2) INFORMATION FOR SEQ ID NO:45:

(i) SEQUENCE CHARACTERISTICS:
        (A) LENGTH: 32 base pairs
        (B) TYPE: Nucleic Acid
        (C) STRANDEDNESS: Single
        (D) TOPOLOGY: Linear (xi) SEQUENCE DESCRIPTION: SEQ ID NO:45:

GGCCACCAGC CGCGGCTGCA ATCTGCACGA GC                            32

(2) INFORMATION FOR SEQ ID NO:46:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO:46:

CAGGGAGTCA AAGGCGGCCG CCAGGGAGTT CATC                          34

(2) INFORMATION FOR SEQ ID NO:47:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO:47:

CTGGATGTGC GCGCTGGCCG CAGCCTCTGT TTGC                          34

(2) INFORMATION FOR SEQ ID NO:48:

(i) SEQUENCE CHARACTERISTICS:
        (A) LENGTH: 37 base pairs
        (B) TYPE: Nucleic Acid
        (C) STRANDEDNESS: Single
        (D) TOPOLOGY: Linear (xi) SEQUENCE DESCRIPTION: SEQ ID NO:48:

CCTCCAAGCT TCGCAGCGCC GCAGCCAGGG CCAGGGC                       37

(2) INFORMATION FOR SEQ ID NO:49:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO:49:

CCGCTGCTCT TTCGCTGCCG CTCGGAATTC CTCC                          34

(2) INFORMATION FOR SEQ ID NO:50:

(i) SEQUENCE CHARACTERISTICS:
        (A) LENGTH: 35 base pairs
        (B) TYPE: Nucleic Acid
        (C) STRANDEDNESS: Single
        (D) TOPOLOGY: Linear (xi) SEQUENCE DESCRIPTION: SEQ ID NO:50:

CTTCTGGACA CGGGCCGCGG CGGCCTCATA CTTCT                         35

```
(2) INFORMATION FOR SEQ ID NO:51:

(i) SEQUENCE CHARACTERISTICS:
        (A) LENGTH: 32 base pairs
        (B) TYPE: Nucleic Acid
        (C) STRANDEDNESS: Single
        (D) TOPOLOGY: Linear (xi) SEQUENCE DESCRIPTION: SEQ ID NO:51:

GGTCTTCTTG GCGGCCGCAA GCTTGCTCTT CT                                  32

(2) INFORMATION FOR SEQ ID NO:52:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO:52:

GCATCCCTGC ACGCCGCGGC ATATAAGCTT TCTTGGACTC CA                       42

(2) INFORMATION FOR SEQ ID NO:53:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO:53:

GTGGCCATTG GCACTCGCAG CCGCGAAAGC TTGCTCAGCA TC                       42

(2) INFORMATION FOR SEQ ID NO:54:

(i) SEQUENCE CHARACTERISTICS:
        (A) LENGTH: 45 base pairs
        (B) TYPE: Nucleic Acid
        (C) STRANDEDNESS: Single
        (D) TOPOLOGY: Linear (xi) SEQUENCE DESCRIPTION: SEQ ID NO:54:

GGCTTTGTTC TGGCTCTTTG CTGCTGCCTT CTGGTGACCA TTGGC                    45

(2) INFORMATION FOR SEQ ID NO:55:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO:55:

CCTCGCTCTC TCCAGTTGTT CAATAGCTGC CGCGTACACT CT                       42

(2) INFORMATION FOR SEQ ID NO:56:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO:56:

CTCCTGCTCC GCCTCGGTCC GAGCTCTCTC C                                   31
```

(2) INFORMATION FOR SEQ ID NO:57:

(i) SEQUENCE CHARACTERISTICS:
        (A) LENGTH: 37 base pairs
        (B) TYPE: Nucleic Acid
        (C) STRANDEDNESS: Single
        (D) TOPOLOGY: Linear (xi) SEQUENCE DESCRIPTION: SEQ ID NO:57:

GGATGGTGAG CCGGTCTGCC TCCTGCAGCT GGAGGCC                      37

(2) INFORMATION FOR SEQ ID NO:58:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO:58:

CGGAGGATGG TGGCCCGGTC GAATTCCTGC AACTGG                       36

(2) INFORMATION FOR SEQ ID NO:59:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO:59:

ATGGAGAGCT GGTTACAGTG CACCGCCAAT GCATTGCGGA GG               42

(2) INFORMATION FOR SEQ ID NO:60:

(i) SEQUENCE CHARACTERISTICS:
        (A) LENGTH: 24 base pairs
        (B) TYPE: Nucleic Acid
        (C) STRANDEDNESS: Single
        (D) TOPOLOGY: Linear (xi) SEQUENCE DESCRIPTION: SEQ ID NO:60:

TCCACATCCT TGGACATCTT CCTG                                   24

(2) INFORMATION FOR SEQ ID NO:61:

(i) SEQUENCE CHARACTERISTICS:
        (A) LENGTH: 41 base pairs
        (B) TYPE: Nucleic Acid
        (C) STRANDEDNESS: Single
        (D) TOPOLOGY: Linear (xi) SEQUENCE DESCRIPTION: SEQ ID NO:61:

CATCATCTGC ATCCCTGGCC TTCTGGTCAT ATCCCTTCTT G                41

(2) INFORMATION FOR SEQ ID NO:62:

(i) SEQUENCE CHARACTERISTICS:
        (A) LENGTH: 24 base pairs
        (B) TYPE: Nucleic Acid
        (C) STRANDEDNESS: Single
        (D) TOPOLOGY: Linear (xi) SEQUENCE DESCRIPTION: SEQ ID NO:62:

GGCTGACTCC TTGGACTGCT TGGC                                   24

(2) INFORMATION FOR SEQ ID NO:63:

(i) SEQUENCE CHARACTERISTICS:
    (A) LENGTH: 27 base pairs
    (B) TYPE: Nucleic Acid
    (C) STRANDEDNESS: Single
    (D) TOPOLOGY: Linear (xi) SEQUENCE DESCRIPTION: SEQ ID NO:63:

GAAGGCCTCG GAGGTAGTCC GGTGCTC                              27

(2) INFORMATION FOR SEQ ID NO:64:

(i) SEQUENCE CHARACTERISTICS:
        (A) LENGTH: 28 base pairs
        (B) TYPE: Nucleic Acid
        (C) STRANDEDNESS: Single
        (D) TOPOLOGY: Linear (xi) SEQUENCE DESCRIPTION: SEQ ID NO:64:

ATGGAGAGCT GGTTGGAGTG CACCCACA                             28

(2) INFORMATION FOR SEQ ID NO:65:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO:65:

CATCATCCTT GACGGACTGC ATGGAGAGCT                           30

(2) INFORMATION FOR SEQ ID NO:66:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO:66:

GATGTCACCT TCCACATCGG AGCCCTCAAG GGTCAG                    36

(2) INFORMATION FOR SEQ ID NO:67:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO:67:

CCCTTTGGGT CGACCGATGG CCAAGTTGAA GCC                       33

(2) INFORMATION FOR SEQ ID NO:68:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO:68:

AGGATCTCGG GGCCCTTTGG CCCTTCCGAT GCGC                      34

(2) INFORMATION FOR SEQ ID NO:69:

```
        (i) SEQUENCE CHARACTERISTICS:
            (A) LENGTH: 31 base pairs
            (B) TYPE: Nucleic Acid
            (C) STRANDEDNESS: Single
            (D) TOPOLOGY: Linear (xi) SEQUENCE DESCRIPTION: SEQ ID NO:69:

CTGGAGGATC TCGAGGTGCT TTGGGCCTTC C                                31

(2) INFORMATION FOR SEQ ID NO:70:

(i) SEQUENCE CHARACTERISTICS:
            (A) LENGTH: 30 base pairs
            (B) TYPE: Nucleic Acid
            (C) STRANDEDNESS: Single
            (D) TOPOLOGY: Linear (xi) SEQUENCE DESCRIPTION: SEQ ID NO:70:

GGAGGATCTC GGGCCCCTTT GGGCCTTCCG                                  30

(2) INFORMATION FOR SEQ ID NO:71:

(i) SEQUENCE CHARACTERISTICS:
            (A) LENGTH: 34 base pairs
            (B) TYPE: Nucleic Acid
            (C) STRANDEDNESS: Single
            (D) TOPOLOGY: Linear (xi) SEQUENCE DESCRIPTION: SEQ ID NO:71:

CTGCAGGAGG ATCCGCGGGC CCTTTGGGCC TTCC                             34

(2) INFORMATION FOR SEQ ID NO:72:

(i) SEQUENCE CHARACTERISTICS:
            (A) LENGTH: 31 base pairs
            (B) TYPE: Nucleic Acid
            (C) STRANDEDNESS: Single
            (D) TOPOLOGY: Linear (xi) SEQUENCE DESCRIPTION: SEQ ID NO:72:

GTCCACTCTG CAGCAGGATC CCGGGGCCCT T                                31

(2) INFORMATION FOR SEQ ID NO:73:

(i) SEQUENCE CHARACTERISTICS:
            (A) LENGTH: 34 base pairs
            (B) TYPE: Nucleic Acid
            (C) STRANDEDNESS: Single
            (D) TOPOLOGY: Linear (xi) SEQUENCE DESCRIPTION: SEQ ID NO:73:

GTTACACCCG TGTCGCCTCT GCAGGAGGAT CCCG                             34
```

TYROSINE PHOSPHORYLATED CLEAVAGE FURROW-ASSOCIATED PROTEINS (PSTPIPS)

This application is a non-provisional application which claims priority to provisional application Ser. No. 60/104,590, filed on Feb. 7, 1997.

FIELD OF THE INVENTION

This present invention concerns novel proteins which interact with and are dephosphorylated by PEST-type protein tyrosine phosphatases. More particularly, the present invention concerns PSTPIP polypeptides which interact with the protein tyrosine phosphatase enzyme PTP HSCF and which are associated with the polymerization of actin monomers.

BACKGROUND OF THE INVENTION

The phosphorylation of tyrosine residues in eukaryotic proteins has been shown to play extremely important roles in the regulation of numerous eukaryotic cellular processes (Fantl et al., *Annu. Rev. Biochem.* 62:453–481 (1993) and Hunter, 1001 *Protein Kinases Redux Toward 2000* 5:367–376 (1994)). While a great deal of information has been accumulated regarding the functions of the protein tyrosine kinases, far less is understood about the physiological roles of protein tyrosine phosphatases (PTPs), the enzymes which remove phosphate from tyrosine residues in proteins. While approximately 50 PTPs have now been described, the functions of only a very few are beginning to be understood (Tonks, *Semin. Cell Biol.* 4:373–453(1993) and Dixon, *Recent Prog. Horm. Res.* 51:405–414 (1996)). However, in general, it appears that many of the PTPs function to modulate the positive or negative signals induced by various protein tyrosine kinases. Therefore, it is likely that PTPs play critical roles in numerous and diverse cellular processes.

The PEST family of PTPs are a group of phosphatase enzymes. The four known examples of these enzymes, PTP PEST [Yang et al., *J. Biol. Chem.* 268(23): 17650 (1993)], PTP PEP [Matthews et al., *Mol. Cell. Biol.* 12(5):2396–2405 (1992)], PTP HSCF [Cheng et al., *Blood* 88(4):1156–1167 (1996); U.S. Ser. No. 08/620,526 filed Mar. 22, 1996]; also known as PTP-K1 [Huang et al., *Oncogene* 13:1567–1573 (1996)], PTP20 [Aoki et al., *J. Biol. Chem.* 271(46):29422–29426(1996)] or FLP1 [Dosil et al., *Blood* 88(12):4510–4525 (1996)] and PTP BDP1 (Kim et al., *Oncogene* 13:2275–2279 (1996)), all contain an N-terminal phosphatase domain which is followed by a variably sized region that is rich in proline, serine and threonine residues, but which has no obvious homology to other proteins. The PEST family of PTPs also contain a highly conserved 20 amino acid long proline rich region at the very C-terminus of the proteins which are believed to be involved in protein-protein interactions. With regard to cell type expression, PTP PEST is ubiquitously expressed (Yang et al., (1993) supra), PTP PEP is expressed in lymphoid cells (Matthews et al., (1992) supra), PTP HSCF is expressed in hematopoietic stem/progenitor cells and fetal thymus (Cheng et al. (1996) supra and Dosil et al., (1996) supra) as well as a subset of adult tissues including bone marrow (Huang et al., (1996) supra) and PTP BDP1 is expressed at low levels in the brain as well as other adult tissues (Kim et al., (1996) supra).

Insight into the physiological functions of PEST PTPs may be obtained from an examination of the proteins which interact with these enzymes, the effects of overexpression of the proteins on cellular differentiation and the possible modes of regulation of the molecules. Transfection of dominant negative forms of PTP PEST into COS cells results in an endogenous, hyperphosphorylated protein that has been identified as p130$^{CAS}$, a cytoplasmic docking/adaptor-type molecule which contains an SH3 domain as well as several potential tyrosine phosphorylated SH2 binding sites (Garton et al., *Mol. Cell. Biol.* 16(11):6408–6418 (1996)). The function of p130$^{CAS}$ is incompletely understood, but it appears to be associated with focal adhesions and is phosphorylated by the p125$^{FAK}$ (Petch et al., *J. Cell. Sci.* 108:1371–1379 (1995) and the RAFTK (Astier et al., *J. Biol. Chem.* 272(1):228–232 (1997) tyrosine kinases, suggesting that it may play a role in integrin-mediated signal transduction. Because dominant negative PTP PEST inhibits dephosphorylation of p130$^{CAS}$, it is likely that this phosphoprotein is a substrate for this PTP.

Interestingly, it has also been recently shown that the PTB domain of the cytoplasmic adaptor protein SHC interacts with a non-phosphorylated PTB-related binding site in the C-terminal region PTP PEST (Charest et al., *J. Biol. Chem.* 271(14):8424–8429 (1996)). In addition, recent data have demonstrated that Csk, a cytoplasmic tyrosine kinase which inactivates Src family kinases by phosphorylation of their C-terminal inhibitory tyrosines, associates with the PEP PTP via an interaction between the Csk SH3 domain and one of the four proline-rich potential SH3 binding sites in the C-terminal region of the enzyme (Cloutier et al., *EMBO J.* 15(18):4909–4918(1996)). Together, these results suggest that the biological activities of PTP PEST and PTP PEP (as well as possibly other PEST PTPs) are mediated through their interaction with critical cytoplasmic signaling proteins involved with the transmission of information from various cell surface receptors.

However, it is believed that the PSTPIP proteins which bind to and are dephosphorylated by members of the PEST-type protein tyrosine phosphatases have not been heretofore disclosed. Therefore, it is an object of the present invention to provide PSTPIP polypeptides which bind to and are dephosphorylated by members of the PEST-type protein tyrosine phosphatases.

It is a further object of the present invention to provide nucleic acid encoding the PSTPIP polypeptides so that those polypeptides may be prepared by recombinant DNA techniques.

These and further objects will be apparent to the ordinarily skilled artisan upon consideration of the specification as a whole.

SUMMARY OF THE INVENTION

These objects are accomplished, in one aspect, by providing isolated PSTPIP polypeptides selected from the group consisting of:

(i) a polypeptide comprising the amino acid sequence of the PSTPIP polypeptide shown in FIG. 1A (SEQ ID NO: 1);

(ii) a further mammalian homologue of the polypeptide of (i);

(iii) a polypeptide encoded by nucleic acid which hybridizes under stringent conditions to nucleic acid encoding the polypeptide of (i) or (ii) and which substantially retains the ability to bind to a member of the PEST-type protein tyrosine phosphatases; and (iv) a functional derivative of any of the polypeptides (i)–(iii) substantially retaining the ability to bind to a member of the PEST-type protein tyrosine phosphatases.

In another aspect, the present invention provides antagonists of the above described PSTPIP polypeptides.

In yet other aspects, the present invention provides isolated nucleic acid sequences which encode the above described PSTPIP polypeptides, vectors comprising those nucleic acid sequences operably linked to control sequences recognized by host cells transformed with those vectors and host cells comprising the above described nucleic acid sequences.

In yet other aspects, the present invention provides antibodies which are capable of binding to the above described PSTPIP polypeptides and hybridoma cell lines which produce such antibodies. In one embodiment, the antibodies are monoclonal antibodies.

The present invention also provides a method for producing the above described PSTPIP polypeptides comprising transforming a host cell with nucleic acid encoding the polypeptide, culturing the transformed cell and recovering the polypeptide from the cell culture.

In another embodiment, the present invention provides a method for inducing the polymerization of actin monomers in a eukaryotic cell comprising introducing the above described PSTPIP polypeptide into the cell.

The present invention also provides an assay for identifying antagonists and agonists of the above described PSTPIP polypeptides comprising contacting the PSTPIP polypeptide with a candidate antagonist or agonist and monitoring the ability of the polypeptide to induce the polymerization of actin monomers.

In yet another embodiment, the invention concerns an assay for identifying a polypeptide capable of interacting with a PST Phosphatase Interacting Protein (PSTPIP), comprising
  (a) expressing nucleic acid molecules encoding a polypeptide comprising a fusion of a native PSTPIP sequence or a fragment thereof to the DNA-binding domain of a transcriptional activator, and a fusion of a candidate polypeptide to the activation domain of a transcriptional activator, in a single host cell carrying a reporter gene; and
  (b) monitoring the association of said candidate polypeptide wit said native PSTPIP sequence or a fragment thereof by detecting a signal of the molecule encoded by said reporter gene.

The present invention further concerns an assay for identifying peptides capable of inhibiting the interaction of a native PST Phosphatase Interacting Protein (PSTPIP) and a native protein tyrosine phosphatase hematopoietic stemcell fraction (PTP HSCF), which comprises contacting said PSPIP and a PTP HSCF, or fragments thereof, with a candidate peptide, and detecting the ability of the PTPPIP and PTP HSCF, of fragments thereof, to interact with each other

BRIEF DESCRIPTION OF THE DRAWINGS

FIGS. 1A–1C. Protein Sequence and Putative Domain Structure of PSTPIP. A. Illustrated is a comparison of the protein sequences of murine PSTPIP (PSTPIP) (SEQ ID NO:1) and S. pombe cdc15 (cdc15) (SEQ ID NO:26). The asterisks illustrate the conserved tyrosine residues and the "+" shows the conserved potential SH3 binding site. The predicted coiled coil and SH3 domains are overlined. B. Sequence comparisons of the SH3 domains of PSTPIP (pstpip.sh3) (SEQ ID NO:3) and several different proteins known to interact with the cytoskeleton including myosin heavy chain (myosin.sh3) (SEQ ID NO:4), spectrin (spectrin.sh3) (SEQ ID NO:5), fodrin (fodrin.sh3) (SEQ ID NO:5), hematopoietic specific protein 1 (hsp.sh3) (SEQ ID NO:6) and cortactin (cortactin.sh3)(SEQ ID NO:7). C. Domain structure of PSTPIP and cdc15p. Illustrated are the predicted coiled coil regions containing regions rich in basic and acidic residues (+-+), the conserved tyrosine residues (*), the conserved potential SH3 binding site (†) and the conserved SH3 domains. Also, shown is the large region in the S. pombe protein which contains predicted PEST degradation signals and which is missing from the mammalian homologue.

FIGS. 6A–6F. In vivo Tyrosine Phosphorylation of PSTPIP. A. Illustrated is the immunoprecipitation of endogenous PSTPIP from Baf3 cells with anti-PSTPIP polyclonal antibody in the presence and absence of the PTP inhibitor pervanadate. Precipitates were blotted with either anti-PSTPIP (αPSTPIP) or anti-phosphotyrosine (α PTyr) antibodies. Note that the protein in the absence of pervanadate is more diffuse and shows a lower phosphotyrosine content than the protein in the presence of the inhibitor. B. Shown are immunoprecipitations done with the indicated antibodies on cells transfected as illustrated. C. Immunoprecipitation of PSTPIP with anti-FLAG antibody (α FLAG) directed against a C-terminal PSTPIP FLAG epitope and blotting with anti-phosphotyrosine antibodies (α P-Tyr). D. Immunoprecipitation of PSTPIP with anti-FLAG antibody (α FLAG) and blotting with anti-FLAG (α FLAG). The absence of visible protein in the lanes containing tyrosine phosphorylated PSTPIP may be due to phosphorylation of the tyrosine in the FLAG epitope. The proteins are clearly visible in the anti-phosphotyrosine blot, however. E. Immunoprecipitation of PTP HSCF with anti-HA antibody (α HA) directed against an N-terminal hemagglutinin epitope and blotting with the same antibody. F. Shown are coprecipitation experiments demonstrating that precipitation of PSTPIP (anti-FLAG tagged) brings down PTP HSCF (anti-HA tagged) and precipitation of PTP HSCF (anti-HA tagged) brings down PSTPIP (anti-FLAG tagged).

DETAILED DESCRIPTION OF THE INVENTION

A. Definitions

Figure 1A-1:
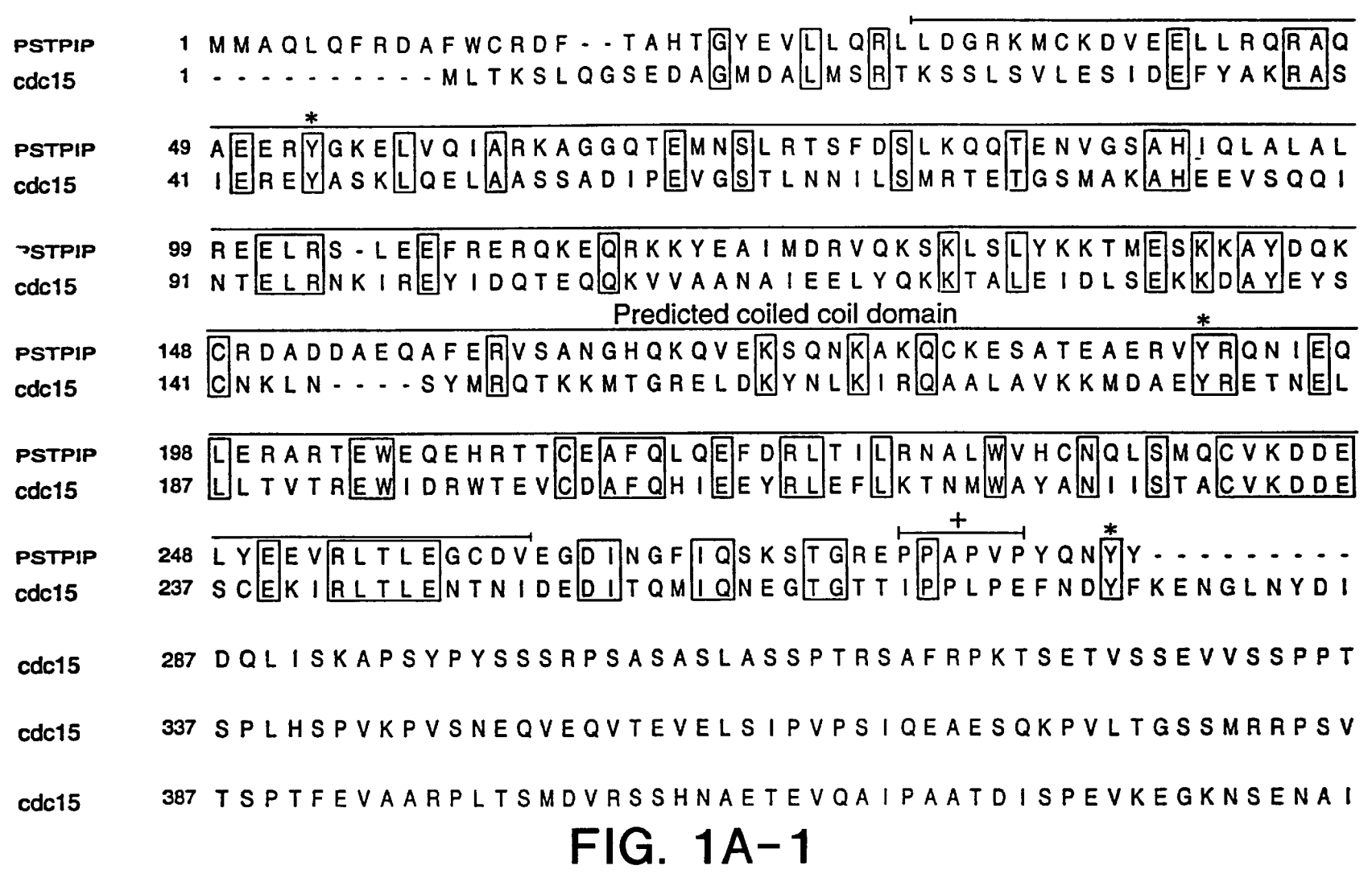
Figure 2A:
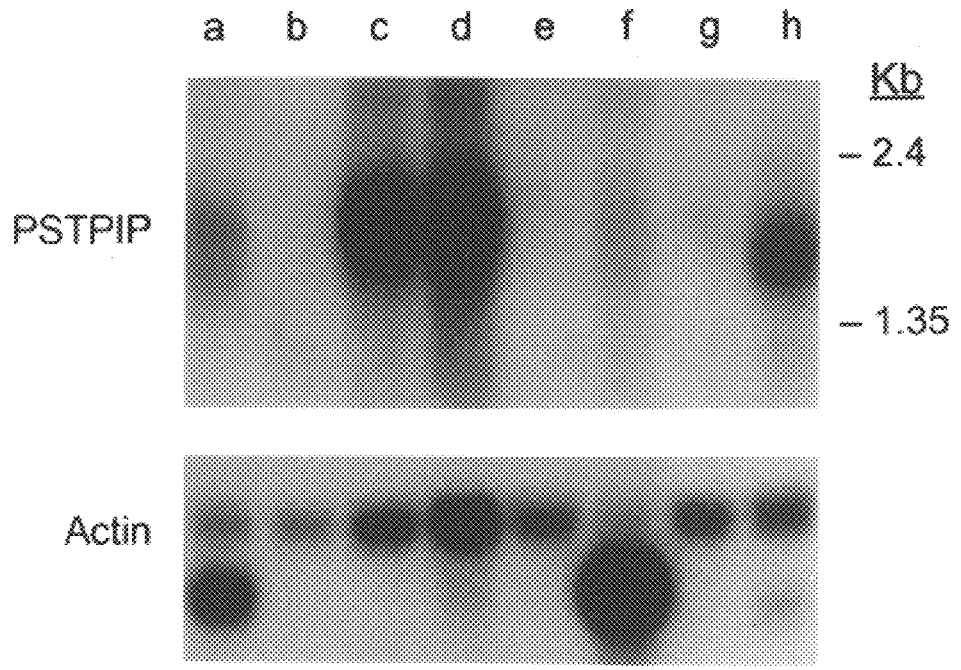
FIGS. 2A–2B. Northern Blot Analysis of the Expression of PSTPIP Transcript. A. Expression of PSTPIP and actin in heart (lane a), brain (lane b), spleen (lane c), lung (lane d), liver (lane e), muscle (lane f), kidney (lane g) and testis (lane h). B. Expression of PSTPIP and actin in 7 day murine embryos (lane a), 11 day murine embryos (lane b), 15 day murine embryos (lane c) and 17 day murine embryos (lane d).

The phrase "PSTPIP polypeptide","PSTPIP", "PST Phosphatase Interacting Protein" and "PTP HSCF interacting protein" are used interchangeably and refer to a polypeptide which comprises the amino acid sequence of the PSTPIP polypeptide shown in FIG. 1 A (SEQ ID NO:1) or a further mammalian homologue thereof. The above terms are also intended to encompass functional polypeptides encoded by nucleic acid which hybridizes under stringent conditions to nucleic acid which encodes a polypeptide comprising the amino acid sequence of the PSTPIP polypeptide shown in FIG. 1A (SEQ ID NO:2) or a further mammalian homologue thereof as well as functional derivatives of any of the above polypeptides.

By "further mammalian homologue" or grammatical equivalents thereof is meant a PSTPIP polypeptide from a mammalian species other than murine which is functionally similar to the PSTPIP polypeptide shown in FIG. 1A (SEQ ID NO:1). Such PSTPIP homologues may be identified in such mammals as, for example, human, rabbit, rat, porcine, non-human primates, equine and ovine. Screening cDNA libraries prepared from these mammals with a probe derived from the nucleic acid encoding the murine PSTPIP polypeptide shown in FIG. 1A (SEQ ID NO:2) will allow identification of such homologues, such as the human homologue (SEQ ID NOS.:28 and 29).

The term "native PSTPIP polypeptide" in this context refers to a naturally occurring PSTPIP polypeptide, having the described properties, of any human or non-human animal species, with or without the initiating methionine, whether purified from the native source, synthesized, produced by recombinant DNA technology or by any combination of these and/or other methods. Native PSTPIP polypeptide specifically includes the native murine PSTPIP protein shown in FIG. 1A (SEQ ID NO:1), and the native human PST PIP protein (SEQ ID NO:29).

A "functional derivative" of a polypeptide is a compound having a qualitative biological activity in common with the native polypeptide. Thus, a functional derivative of a native PSTPIP polypeptide is a compound that has a qualitative biological activity in common with a native PSTPIP polypeptide, for example, as being capable of binding to a member of the PEST-type protein tyrosine phosphatase family and/or being dephosphorylated by a member of the PEST-type protein tyrosine phosphatases when having at least one phosphorylated tyrosine residue and/or associating with actin. "Functional derivatives" include, but are not limited to, fragments of native polypeptides from any animal species (including humans), derivatives of native (human and non-human) polypeptides and their fragments, glycosylation variants of a native polypeptide, and peptide and non-peptide analogs of native polypeptides, provided that they have a biological activity in common with a respective native polypeptide. "Fragments" comprise regions within the sequence of a mature native polypeptide. The term "derivative" is used to define amino acid sequence variants (insertional, deletional and substitutional), and covalent modifications of a native polypeptide. "Non-peptide analogs" are organic compounds which display substantially the same surface as peptide analogs of the native polypeptides. Thus, the non-peptide analogs of the native PSTPIP polypeptide of the present invention are organic compounds which display substantially the same surface as peptide analogs of the native PSTPIP. Such compounds interact with other molecules in a similar fashion as the peptide analogs, and mimic a biological activity of a native PSTPIP of the present invention. The polypeptide functional derivatives of the native PSTPIP of the present invention preferably have at least about 65%, more preferably at least about 75%, even more preferably at least about 85%, most preferably at least about 95% overall sequence homology with the PSTPIP amino acid sequence shown in FIG. 1A (SEQ ID NO:1) and substantially retain the ability to bind to a member of the PEST-type protein tyrosine phosphatases.

The term "biological activity" in the context of the definition of functional derivatives is defined as the possession of at least one physiological function qualitatively in common with a native polypeptide. The functional derivatives of the native PSTPIP of the present invention are unified by their qualitative ability to bind to a member of the PEST-type protein tyrosine phosphatases.

By "PEST-type protein tyrosine phosphatase" is meant a protein tyrosine phosphatase enzyme which possesses a non-catalytic domain comprising a variable sized region that is rich in proline, serine and threonine residues and a C-terminal 20 amino acid segment which is rich in proline residues and which defines at least one potential SH3 binding domain [Pawson, Nature 373:573–580 (1995)]. Included within the PEST-type protein tyrosine phosphatase family are the protein tyrosine phosphatases PTP PEST [Yang et al., (1993) supra], PTP PEP [Matthews et al., (1992) supra], PTP HSCF [Cheng et al., (1996) supra]; also known as PTP-K1 [Huang et al., (1996) supra], PTP20 [Aoki et al., (1996) supra] or FLP1 [Dosil et al., (1996) supra] and PTP BDP1 [Kim et al., (1996) supra].

The term "agonist" is used to refer to peptide and non-peptide analogs of the native PSTPIP polypeptides of the present invention and to antibodies specifically binding native PSTPIP provided that they retain at least one biological activity of a native PSTPIP. Preferably, the agonists of the present invention retain the qualitative ability to bind to a member of the PEST-type protein tyrosine phosphatases and/or induce the polymerization of actin monomers.

The term "antagonist" is used to refer to a molecule inhibiting a biological activity of a native PSTPIP polypeptide of the present invention. Preferably, the antagonists herein inhibit the ability of the PSTPIP polypeptide of the present invention to bind to members of the PEST-type protein tyrosine phosphatase enzymes. It is also preferred that antagonists inhibit the ability of the PSTPIP polypeptide to induce the polymerization of actin monomers.

Agonist and antagonist candidates may comprise a variety of different compounds including peptides, proteins, organic molecules, and the like. For example, it is well within the skill level in the art to prepare combinatorial oligopeptide libraries and screen those libraries for members which either bind to the PSTPIP polypeptide or which interfere with the binding of a PSTPIP polypeptide to a member of the PEST-type protein tyrosine phosphatases.

"Identity" or "homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known in the art.

Ordinarily, the terms "amino acid" and "amino acids" refer to all naturally occurring L-α-amino acids. In some embodiments, however, D-amino acids may be present in the polypeptides or peptides of the present invention in order to facilitate conformational restriction. For example, in order to facilitate disulfide bond formation and stability, a D amino acid cysteine may be provided at one or both termini of a peptide functional derivative or peptide antagonist of the native PSTPIP polypeptide of the present invention. The amino acids are identified by either the single-letter or three-letter designations:

| Asp D | aspartic acid | Ile I | isoleucine |
|---|---|---|---|
| Thr T | threonine | Leu L | leucine |
| Ser S | serine | Tyr Y | tyrosine |
| Glu E | glutamic acid | Phe F | phenylalanine |
| Pro P | proline | His H | histidine |
| Gly G | glycine | Lys K | lysine |

-continued

| Ala A | alanine | Arg R | arginine |
|---|---|---|---|
| Cys C | cysteine | Trp W | tryptophan |
| Val V | valine | Gln Q | glutamine |
| Met M | methionine | Asn N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids
 Acidic Residues: aspartic acid, glutamic acid
 Basic Residues: lysine, arginine, histidine
II. Uncharged Amino Acids
 Hydrophilic Residues: serine, threonine, asparagine, glutamine
 Aliphatic Residues: glycine, alanine, valine, leucine, isoleucine
 Non-polar Residues: cysteine, methionine, proline
 Aromatic Residues: phenylalanine, tyrosine, tryptophan The term "amino acid sequence variant" refers to molecules with some differences in their amino acid sequences as compared to a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

"Antibodies (Abs)" and "immunoglobulins (Igs)" are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186:651–663 (1985) and Novotny and Haber, Proc. Natl. Acad. Sci. USA 82:4592–4596 (1985)).

The term "variable" refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) or hypervariable regions both in the light chain and the heavy chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., *Sequences of Proteins of Immunological Interest*, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen binding fragments, called Fab fragments, each with a single antigen binding site, and a residual "Fc" fragment, whose name reflects its ability to crystallize readily. Pepsin treatment yields an $F(ab')_2$ fragment that has two antigen combining sites and is still capable of cross-linking antigen.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other, chemical couplings of antibody fragments are also known.

The light chains of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

The term "antibody" is used in the broadest sense and specifically covers single monoclonal antibodies (including agonist and antagonist antibodies), antibody compositions with polyepitopic specificity, as well as antibody fragments (e.g., Fab, $F(ab')_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods (see, e.g. U.S. Pat. No. 4,816,567 by Cabilly et al.).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 by Cabilly et al.; Morrison et al., *Proc. Natl. Acad. Sci. USA* 81:6851–6855 (1984)).

"Humanized" forms of non-human (e.g. murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature* 321:522–525 (1986); Reichmann et al., *Nature* 332:323–329 1988; EP-B-239 400 published Sep. 30, 1987; Presta, *Curr. Op. Struct. Biol.* 2:593–596 (1992); and EP-B-451 216 published Jan. 24, 1996.

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

"Immunoadhesins" or "PSTPIP-immunoglobulin chimeras" are chimeric antibody-like molecules that combine the functional domain(s) of a binding protein (usually a receptor, a cell-adhesion molecule or a ligand) with the an immunoglobulin sequence. The most common example of this type of fusion protein combines the hinge and Fc regions of an immunoglobulin (Ig) with domains of a protein that recognizes and binds to a specific ligand. This type of molecule is called an "immunoadhesin", because it combines "immune" and "adhesion" functions; other frequently used names are "Ig-chimera", "Ig-" or "Fc-fusion protein", or "receptor-globulin."

"Oligonucleotides" are short length, single- or double-stranded polydeoxynucleotides that are chemically synthesized by known methods such as phosphotriester, phosphite, or phosphoramidite chemistry, using solid phase techniques such as those described in EP 266,032, published May 4, 1988, or via deoxynucleoside H-phosphonate intermediates as described by Froehler et al., *Nucl. Acids Res.* 14:5399 (1986). They are then purified on polyacrylamide gels.

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50° C., or (2) employing during hybridization a denaturing agent, such as formamide, for example, 50% (vol/vol) formamide with 0. 1% bovine serum albumin/ 0.1% Ficoll/0.1% polyvinylpyrrolidone/50 nM sodium phosphate buffer at pH 6.5 with 750 mM sodium chloride, 75 mM sodium citrate at 42° C. Another example is use of 50% formamide, 5×SSC (0.75 M NaCl, 0.075 M sodium citrate), 50 mM sodium phosphate (pH 6/8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. Yet another example is hybridization using a buffer of 10% dextran sulfate, 2×SSC (sodium chloride/sodium citrate) and 50% formamide at 55° C., followed by a high-stringency wash consisting of 0.1×SSC containing EDTA at 55° C.

"Transformation" means introducing DNA into an organism so that the DNA is replicable, either as an extrachromosomal element or by chromosomal integration. Depending on the host cell used, transformation is done using standard techniques appropriate to such cells. The calcium treatment employing calcium chloride, as described by Cohen, *Proc. Natl. Acad. Sci USA* 69:2110 (1972) and Mandel et al., *J. Mol. Biol.* 53:154 (1970), is generally used for prokaryotes or other cells that contain substantial cell-wall barriers. For mammalian cells without such cell walls, the calcium phosphate precipitation method of Graham and van der Eb, *Virology* 52:456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.* 130:946 (1977) and Hsiao et al., *Proc. Natl. Acad. Sci. USA* 76:3829 (1979). However, other methods for introducing DNA into cells such as by nuclear injection, electroporation or by protoplast fusion may also be used.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.* 9:6103–6114 (1981) and Goeddel et al., *Nucleic Acids Res.* 8:4057 (1980).

"Ligation" refers to the process of forming phosphodiester bonds between two double stranded nucleic acid fragments (Maniatis et al., (1982) supra). Unless otherwise provided, ligation may be accomplished using known buffers and conditions with 10 units of T4 DNA ligase ("ligase") per 0.5 mg of approximately equimolar amounts of the DNA fragments to be ligated.

"Preparation" of DNA from transformants means isolating plasmid DNA from microbial culture. Unless otherwise provided, the alkaline/SDS method of Maniatis et al., (1982) supra, may be used.

B. Production of PSTPIP Polypeptides by Recombinant DNA Technology

1. Identification and Isolation of Nucleic Acid Encoding PSTPIP

Nucleic acids encoding the native PSTPIP proteins of the present invention may be isolated from cDNA or genomic libraries. For example, a suitable cDNA library can be constructed by obtaining polyadenylated mRNA from cells known to express the desired PSTPIP protein (for example Baf3, available through the American Type Culture Collection), and using the mRNA as a template to synthesize double stranded cDNA. mRNA encoding the native PSTPIP of the present invention is expressed, for example, in tissues derived from adult lung and spleen as well as in very early 7 day murine embryos. The gene encoding the novel PSTPIP polypeptide of the present invention can also be obtained from a genomic library, such as a human genomic cosmid library, or a mouse-derived embryonic cell (ES) genomic library.

Libraries, either cDNA or genomic, are then screened with probes designed to identify the gene of interest or the protein encoded by it. For cDNA expression libraries, suitable probes include monoclonal and polyclonal antibodies that recognize and specifically bind to a PSTPIP polypeptide. For cDNA libraries, suitable probes include carefully selected oligonucleotide probes (usually of about 20–80 bases in length) that encode known or suspected portions of a PSTPIP polypeptide from the same or different species, and/or complementary or homologous cDNAs or fragments thereof that encode the same or a similar gene. Appropriate probes for screening genomic DNA libraries include, without limitation, oligonucleotides, cDNAs, or fragments thereof that encode the same or a similar gene, and/or homologous genomic DNAs or fragments thereof. Screening the cDNA or genomic library with the selected probe may be conducted using standard procedures as described in Chapters 10–12 of Sambrook et al., *Molecular Cloning: A Laboratory Manual*, New York, Cold Spring Harbor Laboratory Press, 1989.

If DNA encoding a polypeptide of the present invention is isolated by using carefully selected oligonucleotide sequences to screen cDNA libraries from various tissues, the oligonucleotide sequences selected as probes should be sufficient in length and sufficiently unambiguous that false positives are minimized. The actual nucleotide sequence(s) is/are usually designed based on regions which have the least codon redundancy. The oligonucleotides may be degenerate at one or more positions. The use of degenerate oligonucleotides is of particular importance where a library is screened from a species in which preferential codon usage is not known.

The oligonucleotide must be labeled such that it can be detected upon hybridization to DNA in the library being screened. The preferred method of labeling is to use ATP (e.g., $\gamma^{32}P$) and polynucleotide kinase to radiolabel the 5' end of the oligonucleotide. However, other methods may be used to label the oligonucleotide, including, but not limited to, biotinylation or enzyme labeling.

cDNAs encoding PSTPIP polypeptides can also be identified and isolated by other known techniques of recombinant DNA technology, such as by direct expression cloning, or by using the polymerase chain reaction (PCR) as described in U.S. Pat. No. 4,683,195, issued Jul. 28, 1987, in section 14 of Sambrook et al., supra, or in Chapter 15 of *Current Protocols in Molecular Biology*, Ausubel et al. eds., Greene Publishing Associates and Wiley-Interscience (1991).

Once cDNA encoding a PSTPIP polypeptide from one species has been isolated, cDNAs from other species can also be obtained by cross-species hybridization. According to this approach, human or other mammalian cDNA or genomic libraries are probed by labeled oligonucleotide sequences selected from known PSTPIP sequences (such as murine PSTPIP) in accord with known criteria, among which is that the sequence should be sufficient in length and sufficiently unambiguous that false positives are minimized. Typically, a $^{32}P$-labeled oligonucleotide having about 30 to 50 bases is sufficient, particularly if the oligonucleotide contains one or more codons for methionine or tryptophan. Isolated nucleic acid will be DNA that is identified and separated from contaminant nucleic acid encoding other polypeptides from the source of nucleic acid. Hybridization is preferably performed under "stringent conditions", as herein above defined.

Once the sequence is known, the gene encoding a particular PSTPIP polypeptide can also be obtained by chemical synthesis, following one of the methods described in Engels and Uhlmann, Agnew. *Chem. Int. Ed. Engl.* 28:716 (1989). These methods include triester, phosphite, phosphoramidite and H-phosphonate methods, PCR and other autoprimer methods, and oligonucleotide syntheses on solid supports.

2. Cloning and Expression of Nucleic Acid Encoding PSTPIP

Once the nucleic acid encoding PSTPIP is available, it is generally ligated into a replicable expression vector for further cloning (amplification of the DNA), or for expression.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transcription termination sequence. Construction of suitable vectors containing one or more of the above listed components, the desired coding and control sequences, employs standard ligation techniques. Isolated plasmids or DNA fragments are cleaved, tailored, and religated in the form desired to generate the plasmids required. For analysis to confirm correct sequences in plasmids constructed, the ligation mixtures are commonly used to transform *E. coli* cells, e.g. *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9:309 (1981) or by the method of Maxam et al., *Methods in Enzymology* 65:499(1980).

The polypeptides of the present invention may be expressed in a variety of prokaryotic and eukaryotic host cells. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), Pseudomonas species, or *Serratia Marcesans* are suitable.

In addition to prokaryotes, eukaryotic microbes such as filamentous fungi or yeast are suitable hosts for vectors herein. *Saccharomyces cerevisiae*, or common baker's yeast, is the most commonly used among lower eukaryotic host microorganisms. However, a number of other genera, species and strains are commonly available and useful herein, such as *S. pombe* (Beach and Nurse, *Nature* 290:140 (1981)), *Kluyveromyces lactis* (Louvencourt et al., *J. Bacteriol.* 737 (1983)); yarrowia (EP 402,226); *Pichia pastoris* (EP 183,070), *Trichoderma reesia* (EP 244,234), *Neurospora crassa* (Case et al., *Proc. Natl. Acad. Sci USA* 76:5259–5263 (1979)) and Aspergillus hosts such as *A. nidulans* (Ballance et al., *Biochem. Biophys. Res. Commun.* 112:284–289 (1983); Tilburn et al., *Gene* 26:205–221 (1983); Yelton et al., *Proc. Natl Acad. Sci. USA* 81:1470–1474 (1984)) and *A. niger* (Kelly and Hynes, *EMBO J* 4:475–479(1985)).

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g. Luckow et al, *Bio/Technology* 6:47–55 (1988); Miller et al., in *Genetic Engineering*, Setlow, J. K. et al., eds., Vol. 8 (Plenum Publishing, 1986), pp. 277–279; and Maeda et al., *Nature* 315:592–594(1985). A variety of such viral strains are publicly available, e.g. the L-1 variant of *Autographa californica* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the PSTPIP DNA. During incubation of the plant cell culture with *A. tumefaciens*, the DNA encoding a PSTPIP polypeptide is transferred to the plant cell host such that it is transfected, and will, under appropriate conditions, express the PSTPIP DNA. In addition, regulatory and signal sequences compatible with plant cells are available, such as the nopaline synthase promoter and polyadenylation signal sequences. Depicker et al., *J. Mol. Appl. Gen.* 1:561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) is per se well known. See *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney cell line (293 or 293 cells subcloned for growth in suspension culture, Graham et al., *J. Gen. Virol.* 36:59 (1977)); baby hamster kidney cells 9BHK, (ATCC CCL 10); Chinese hamster ovary cells/-DHFR [CHO, Urlaub and Chasin, *Proc. Natl. Acad. Sci. USA* 77:4216 (1980)]; mouse sertolli cells [TM4, Mather, *Biol. Reprod* 23:243–251 (1980)]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TRI cells [Mather et al., *Annals N.Y. Acad. Sci.* 383:44068 (1982)]; MRC 5 cells; FS4 cells; and a human hepatoma cell line (Hep G2). Preferred host cells are human embryonic kidney 293 and Chinese hamster ovary cells.

Particularly useful in the practice of this invention are expression vectors that provide for the transient expression in mammalian cells of DNA encoding a PSTPIP polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by clones DNAs, as well as for the rapid screening of such polypeptides for desired biological or physiological properties. Thus, transient expression systems are particularly useful in the invention for purposes of identifying analogs and variants of a PSTPIP polypeptide.

Other methods, vectors, and host cells suitable for adaptation to the synthesis of the PSTPIP polypeptides in recombinant vertebrate cell culture are described in Getting et al., *Nature* 293:620–625 (1981); Mantel et al., *Nature* 281:40–46 (1979); Levinson et al.; EP 117,060 and EP 117,058. Particularly useful plasmids for mammalian cell culture expression of the PSTPIP polypeptides are pRK5 (EP 307,247) or pSVI6B (PCT Publication No. WO 91/08291).

Other cloning and expression vectors suitable for the expression of the PSTPIP polypeptides of the present invention in a variety of host cells are, for example, described in EP 457,758 published Nov. 27, 1991. A large variety of expression vectors are now commercially available. An exemplary commercial yeast expression vector is pPIC.9 (Invitrogen), while an commercially available expression vector suitable for transformation of *E. coli* cells is PET15b (Novagen).

C. Culturing the Host Cells

Prokaryote cells used to produced the PSTPIP polypeptides of this invention are cultured in suitable media as describe generally in Sambrook et al., supra.

Mammalian cells can be cultured in a variety of media. Commercially available media such as Ham's F 10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace, *Meth. Enzymol.* 58:44 (1979); Barnes and Sato, *Anal. Biochem.* 102:255 (1980), U.S. Pat. Nos. 4,767,704; 4,657,866; 4,927,762; or 4,560,655; WO 90/03430; WO 87/00195 or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan.

The host cells referred to in this disclosure encompass cells in in vitro cell culture as well as cells that are within a host animal or plant.

It is further envisioned that the PSTPIP polypeptides of this invention may be produced by homologous recombination, or with recombinant production methods utilizing control elements introduced into cells already containing DNA encoding the particular PSTPIP polypeptide.

D. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci USA* 77:5201–5205 (1980)], dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as a site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hse et al., *Am. J. Clin. Pharm.* 75:734–738 (1980).

Antibodies useful for immunohistochemical staining and/or assay of sample fluids may be either monoclonal or polyclonal, and may be prepared in any animal. Conveniently, the antibodies may be prepared against a native PSTPIP polypeptide, or against a synthetic peptide based on the DNA sequence provided herein as described further hereinbelow.

E. Amino Acid Sequence Variants of Native PSTPIP Polypeptides

Amino acid sequence variants of native PSTPIP polypeptides are prepared by methods known in the art by introducing appropriate nucleotide changes into a PSTPIP DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the PSTPIP, the amino acid sequence variants of PSTPIP polypeptides are preferably constructed by mutating the DNA, either to arrive at an allele or an amino acid sequence variant that does not occur in nature.

One group of the mutations will be created within the N-terminal coiled coil region of the polypeptides of the present invention. Non-conservative substitutions within this region may result in PSTPIP variants which lose their ability to be bound and/or dephosphorylated by PTP HSCF (or any other PEST PTP). PSTPIP variants mutated to alter their ability to associate with actin will be useful, for example, as inducers or inhibitors of cytokinesis.

In the murine PSTPIP sequence (SEQ ID NO:1) the coiled-coil domain is defined as extending from about amino acid position 30 to about amino acid position 261 (see FIG. 1A). However, in a broader sense, the coiled-coil domain may be viewed as starting at the N-terminus of the PSTPIP protein. Mutational analysis revealed that the six cysteine residues present within this region are not critical for the correct folding and function of PSTPIP. Unexpectedly, the tryptophan (W) residue at amino acid position 232 of the murine sequence was found to be critical for binding PTP HSCF. Mutation of this tryptophan residue to alanine resulted in a complete loss of binding. Accordingly, in order to retain biological activity, the tryptophan at position 232 must be retained, although substitution by other aromatic amino acids, e.g. tyrosine and phenylalanine might result in variants which retain their ability to bind PTP HSCF to some extent. Conversely, if variants that do not bind PTP HSCF are required, the tryptophan residue at position 232 of the murine sequence, and corresponding residues in the PSTPIP proteins from other mammalian species, including human, are a primary target for substitution.

While the tryptophan residue at position 232 of SEQ. ID. NO: 1 plays a critical role in PTP HSCF binding, the tryptophan at position 205, the phenylalanine at position 221 and leucine at position 224 are not critical, and can be readily mutated.

Alternatively, or in addition, amino acid alterations can be made at sites that differ in PSTPIP proteins from various species, or in highly conserved regions, depending on the goal to be achieved. Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3. One helpful technique is called "alanine scanning" (Cunningham and Wells, *Science* 244, 1081–1085 [1989]).

Naturally-occurring amino acids are divided into groups based on common side chain properties:

(1) hydrophobic: norleucine, met, ala, val, leu, ile;
(2) neutral hydrophobic: cys, ser, thr;
(3) acidic: asp, glu;
(4) basic: asn, gin, his, lys, arg;
(5) residues that influence chain orientation: gly, pro; and
(6) aromatic: trp, tyr, phe.

Conservative substitutions involve exchanging a member within one group for another member within the same group, whereas non-conservative substitutions will entail exchanging a member of one of these classes for another. Substantial changes in function or immunological identity are made by selecting substitutions that are less conservative, i.e. differ more significantly in their effect on maintaining (a) the structure of the polypeptide backbone in the area of substitution, for example as a sheet or helical conformation, (b) the charge or hydrophobicity of the molecule at the target site or (c) the bulk of the side chain. The substitutions which in general are expected to produce the greatest changes in the properties of the novel native PSTPIP polypeptides of the present invention will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g. glycine.

Amino acid sequence deletions generally range from about 1 to 30 residues, more preferably about 1 to 10 residues, and typically are contiguous.

The results discosed in the examples show that the N-terminus of PSTPIP is required for the formation of a correctly folded protein that is capable of binding PTPH-SCF. Accordingly, if structural integrity and biological activity are to be retained, any N-terminal deletion should not extend beyond about amino acid 25 of the murine PSTPIP sequence or the corresponding amino acid in the human or other mammalian sequences. The presence of the C-terminal portion of the PSTPIP proteins is less critical. The coiled-coil domain is sufficient for proper folding of the protein, as attested by data showing that transfection of the coiled-coil domain of PSTPIP results in co-localization of the protein with the cortical actin cytoskeleton and the lamellipodia, an event which presumably requires a correctly folded protein. As noted before, and is shown in FIG. 1A, in the murine PSTPIP sequence (SEQ ID NO:1) the coiled-coil domain is defined as extending from about amino acid position30 to about amino acid position 261. Similar domains can be readily identified in PSTPIPs from other mammalian species, e.g. humans.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the PSTPIP protein amino acid sequence) may range generally from about 1 to 10 residues, more preferably 1 to 5 residues, more preferably 1 to 3 residues.

Examples of terminal insertions include the PSTPIP polypeptides with an N-terminal methionyl residue, an artifact of its direct expression in bacterial recombinant cell culture, and fusion of a heterologous N-terminal signal sequence to the N-terminus of the PSTPIP molecule to facilitate the secretion of the mature PSTPIP from recombinant host cells. Such signal sequences will generally be obtained from, and thus homologous to, the intended host cell species. Suitable sequences include STII or lpp for *E. coli,* alpha factor for yeast, and viral signals such as herpes gD for mammalian cells.

Other insertional variants of the native PSTPIP molecules include the fusion of the N- or C-terminus of the PSTPIP molecule to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions), albumin, or ferritin, as described in WO 89/02922 published on Apr. 6, 1989.

Further insertional variants are immunologically active derivatives of the novel PSTPIP polypeptides, which comprise the PSTPIP polypeptide and a polypeptide containing an epitope of an immunologically competent extraneous polypeptide, i.e. a polypeptide which is capable of eliciting an immune response in the animal to which the fusion is to be administered or which is capable of being bound by an antibody raised against an extraneous polypeptide. Typical examples of such immunologically competent polypeptides are allergens, autoimmune epitopes, or other potent immunogens or antigens recognized by pre-existing antibodies in the fusion recipient, including bacterial polypeptides such as trpLE, β-galactosidase, viral polypeptides such as herpes gD protein, and the like.

Immunogenic fusions are produced by cross-linking in vitro or by recombinant cell culture transformed with DNA encoding an immunogenic polypeptide. It is preferable that the immunogenic fusion be one in which the immunogenic sequence is joined to or inserted into a novel PSTPIP molecule or fragment thereof by (a) peptide bond(s). These products therefore consist of a linear polypeptide chain containing the PSTPIP epitope and at least one epitope foreign to the PSTPIP polypeptide. It will be understood that it is within the scope of this invention to introduce the epitopes anywhere within a PSTPIP molecule of the present invention or a fragment thereof. These immunogenic insertions are particularly useful when formulated into a pharmacologically acceptable carrier and administered to a subject in order to raise antibodies against the PSTPIP molecule, which antibodies in turn are useful as diagnostics, in tissue-typing, or in purification of the novel PSTPIP polypeptides by immunoaffinity techniques known per se. Alternatively, in the purification of the PSTPIP polypeptides of the present invention, binding partners for the fused extraneous polypeptide, e.g. antibodies, receptors or ligands, are used to adsorb the fusion from impure admixtures, after which the fusion is eluted and, if desired, the novel PSTPIP is recovered from the fusion, e.g. by enzymatic cleavage.

After identifying the desired mutation(s), the gene encoding a PSTPIP variant can, for example, be obtained by chemical synthesis using well known techniques. More preferably, DNA encoding a PSTPIP amino acid sequence variant is prepared by site-directed mutagenesis of DNA that encodes an earlier prepared variant or a nonvariant version of the PSTPIP. Site-directed (site-specific) mutagenesis allows the production of PSTPIP variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as Edelman et al., *DNA* 2:183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA,* A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published by Zoller et al., *Nucleic Acids Res.* 10:6487–6500 [1982]). Also, plasmid vectors that contain a single-stranded phage origin of replication (Veira et al., *Meth. Enzymol* 153:3 [1987]) may be employed to obtain single-stranded DNA. Alternatively, nucleotide substitutions are introduced by synthesizing the appropriate DNA fragment in vitro, and amplifying it by PCR procedures known in the art.

The PCR technique may also be used in creating amino acid sequence variants of a PSTPIP polypeptide. In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GENEAMP® kits (obtained from Perkin-Elmer Cetus, Norwalk, Conn. and Emeryville, Calif.), and 25 pmole of each oligonucleotide primer, to a final volume of 50 μl. The reaction mixture is overlayered with 35 μl mineral oil. The reaction is denatured for 5 minutes at 100° C., placed briefly on ice, and then 1 μl *Thermal aquaticus* (Taq) DNA polymerase (5 units/μl), purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C., 30 sec. 72° C., then 19 cycles of the following:

30 sec. 94° C., 30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector.

Another method for preparing variants, cassette mutagenesis, is based on the technique described by Wells et al., *Gene* 34:315 (1985).

Additionally, the so-called phagemid display method may be useful in making amino acid sequence variants of native or variant PSTPIP polypeptides or their fragments. This method involves (a) constructing a replicable expression vector comprising a first gene encoding a receptor to be mutated, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a suitable antigen so that at least a portion of the phagemid particles bind to the antigen; and (g) separating the phagemid particles that bind from those that do not. Steps (d) through (g) can be repeated one or more times. Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M1 3R408, M13-VCS, and Phi X 174. The preferred helper phage is M13K07, and the preferred coat protein is the M 13 Phage gene III coat protein. The preferred host is *E. coli*, and protease-deficient strains of *E. coli*.

Since it is often difficult to predict in advance the characteristics of a variant PSTPIP, it will be appreciated that some screening will be needed to select the optimum variant.

Further details of the foregoing and similar mutagenesis techniques are found in general textbooks, such as, for example, Sambrook et al., supra, and *Current Protocols in Molecular Biology*, Ausubel et al. eds., supra.

F. Glycosylation Variants

Glycosylation variants are included within the scope of the present invention. They include variants completely lacking in glycosylation (unglycosylated), variants having at least one less glycosylated site than the native form (deglycosylated) as well as variants in which the glycosylation has been changed. Included are deglycosylated and unglycosylated amino acid sequences variants, deglycosylated and unglycosylated native PSTPIP, and other glycosylation variants. For example, substitutional or deletional mutagenesis may be employed to eliminate the N- or O-linked glycosylation sites in the a native or variant PSTPIP molecule of the present invention, e.g. the asparagine residue may be deleted or substituted for another basic residue such as lysine or histidine. Alternatively, flanking residues making up the glycosylation site may be substituted or deleted, even though the asparagine residues remain unchanged, in order to prevent glycosylation by eliminating the glycosylation recognition site.

Additionally, unglycosylated PSTPIP polypeptides which have the glycosylation sites of a native molecule may be produced in recombinant prokaryotic cell culture because prokaryotes are incapable of introducing glycosylation into polypeptides.

Glycosylation variants may be produced by selecting appropriate host cells or by in vitro methods. Yeast and insect cells, for example, introduce glycosylation which varies significantly from that of mammalian systems. Similarly, mammalian cells having a different species (e.g. hamster, murine, porcine, bovine or ovine), or tissue origin (e.g. lung, liver, lymphoid, mesenchymal or epidermal) than the source of the PSTPIP polypeptide are routinely screened for the ability to introduce variant glycosylation as characterized for example by elevated levels of mannose or variant ratios of mannose, fucose, sialic acid, and other sugars typically found in mammalian glycoproteins. In vitro processing of the PSTPIP typically is accomplished by enzymatic hydrolysis, e.g. neuraminidase digestion.

G. Covalent Modifications of PSTPIP Polypeptides

Covalent modifications of PSTPIP polypeptides are included within the scope herein.

Such modifications are traditionally introduced by reacting targeted amino acid residues of the PSTPIP polypeptides with an organic derivatizing agent that is capable of reacting with selected sites or terminal residues, or by harnessing mechanisms of post-translational modifications that function in selected recombinant host cells. The resultant covalent derivatives are useful in programs directed at identifying residues important for biological activity, for immunoassays of the PSTPIP, or for the preparation of anti-PSTPIP antibodies for immunoassays of the recombinant. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Cysteinyl residues most commonly are reacted with α-haloacetates (and 1 5 corresponding amines), such as chloroacetic acid or chloroacetamide,to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizoleand tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R'—N=C=N—R') such as 1 -cyclohexyl-3-(2-morpholinyl4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl, threonyl or tyrosyl residues, methylation of the a-amino groups of lysine, arginine, and histidine side chains (T. E. Creighton, *Proteins: Structure and Molecular Properties,* W. H. Freeman & Co., San Francisco, pp. 79–86 [1983]), acetylation of the N-terminal amine, and amidation of any C-terminal carboxyl group. The molecules may further be covalently linked to nonproteinaceous polymers, e.g. polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

Derivatization with bifunctional agents is useful for preparing intramolecular aggregates of the PSTPIP polypeptides with polypeptides as well as for cross-linking the PSTPIP polypeptide to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio]propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other derivatives comprise the novel peptides of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The PSTPIP polypeptides may be linked to various nonproteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The PSTPIP polypeptides may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences,* 16th Edition, Oslo, A., Ed.

Further derivatives of the PSTPIP polypeptides herein are the so-called "immunoadhesins". To date, more than fifty immunoadhesins have been reported in the art.

Immunoadhesins reported in the literature include, for example, fusions of the T cell receptor (Gascoigne et al.,

*Proc. Natl. Acad. Sci. USA* 84:2936–2940 [1987]); CD4 (Capon et al., *Nature* 337:525–531 [1989]; Traunecker et al., *Nature* 339:68–70 [1989]; Zettmeissel et al., *DNA Cell Biol. USA* 9:347–353 [1990]; Byrn et al., *Nature* 344:667–670 [1990]); L-selectin (homing receptor) (Watson et al., *J Cell. Biol.* 110:2221–2229 [1990]; Watson et al., *Nature* 349:164–167 [1991]); E-selectin [Mulligan et al., *J. Immunol.* 151:6410–17 [1993]; Jacob et al., *Biochemistry* 34:1210–1217 [1995]); P-selectin (Mulligan et al., supra; Hollenbaugh et al., *Biochemistry* 34:5678–84 [1995]); ICAM-1 (Stauton et al., *J. Exp. Med.* 176:1471–1476 [1992]; Martinet al., *J. Virol.* 67:3561–68 [1993]; Roep et al., *Lancet* 343:1590–93 [1994]); ICAM-2 (Damle et al., *J. Immunol.* 148:665–71 [1992]); ICAM-3 (Holness et al., *J. Biol. Chem.* 270:877–84 [1995]); LFA-3 (Kanner et al., *J. Immunol.* 148:223–229 [1992]); L1 glycoprotein (Doherty et al., *Neuron* 14:57–66 [1995]); TNF-R1 (Ashkenazi et al., *Proc. Natl. Acad. Sci USA* 88:10535–539 [1991]; Lesslauer et al., *Eur. J. Immunol.* 21:2883–86 [1991]; Peppel et al., *J. Exp. Med.* 174:1483–1489 [1991]); TNF-R2(Zack et al., *Proc. Natl. Acad. Sci. USA* 90:2335–39 [1993]; Wooley et al., *J. Immunol.* 151:6602–07 [1993]); CD44 [Aruffo et al., *Cell* 61:1303–1313 (1990)]; CD28 and B7 [Linsley et al., *J. Exp. Med* 173:721–730 (1991)]; CTLA-4 [Lisley et al., *J. Exp. Med.* 174:561–569 (1991)]; CD22 [Stamenkovic et al., *Cell* 66:1133–1144 (1991)]; NP receptors [Bennett et al., *J. Biol. Chem.* 266:23060–23067 (1991)]; IgE receptor α [Ridgway and Gorman, *J. Cell. Biol.* 115, abstr. 1448 (1991)]; HGF receptor [Mark, M. R. et al., 1992, *J. Biol. Chem.* submitted]; IFN-γR α- and β-chain [Marsters et al., *Proc. Natl. Acad. Sci USA* 92:5401–05 [1995]); trk-A, -B, and -C (Shelton et al., *J. Neurosci.* 15:477–91 [1995]); IL-2 (Landolfi, *J. Immunol.* 146:915–19 [1991]); IL-10 (Zheng et al., *J. Immunol.* 154:5590–5600 [1995]).

The simplest and most straightforward immunoadhesin design combines the binding region(s) of the 'adhesin' protein with the hinge and Fc regions of an immunoglobulin heavy chain. Ordinarily, when preparing the PSTPIP-immunoglobulin chimeras of the present invention, nucleic acid encoding the desired PSTPIP polypeptide will be fused C-terminally to nucleic acid encoding the N-terminus of an immunoglobulin constant domain sequence, however N-terminal fusions are also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics of the PSTPIP-immunoglobulin chimeras.

In a preferred embodiment, the sequence of a native, mature PSTPIP polypeptide, or variant or fragment thereof, is fused to the N-terminus of the C-terminal portion of an antibody (in particular the Fc domain), containing the effector functions of an immunoglobulin, e.g. IgG-1. It is possible to fuse the entire heavy chain constant region to the PSTPIP sequence. However, more preferably, a sequence beginning in the hinge region just upstream of the papain cleavage site (which defines IgG Fc chemically; residue 216, taking the first residue of heavy chain constant region to be 114 [Kabat et al., supra], or analogous sites of other immunoglobulins) is used in the fusion. In a particularly preferred embodiment, the PSTPIP sequence (full length or fragment or variant) is fused to the hinge region and CH2 and CH3 or CH1, hinge, CH2 and CH3 domains of an IgG-1, IgG-2, or IgG-3 heavy chain. The precise site at which the fusion is made is not critical, and the optimal site can be determined by routine experimentation.

In some embodiments, the PSTPIP-immunoglobulin chimeras are assembled as multimers, and particularly as homodimers or -tetramers (WO 91/08298). Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Various exemplary assembled PSTPIP-immunoglobulin chimeras within the scope herein are schematically diagramed below:

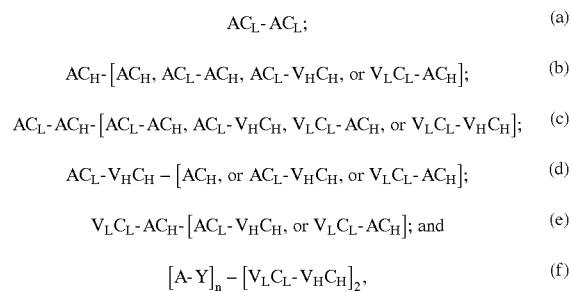

wherein
each A represents identical or different novel PSTPIP polypeptide amino acid sequences;
$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed as being present in the ordinary locations which they occupy in the immunoglobulin molecules.

Alternatively, the PSTPIP amino acid sequences can be inserted between immunoglobulin heavy chain and light chain sequences such that an immunoglobulin comprising a chimeric heavy chain is obtained. In this embodiment, the PSTPIP polypeptide sequences are fused to the 3' end of an immunoglobulin heavy chain in each arm of an immunoglobulin, either between the hinge and the CH2 domain, or between the CH2 and CH3 domains. Similar constructs have been reported by Hoogenboom, H. R. et al., *Mol. Immunol.* 28:1027–1037 (1991).

Although the presence of an immunoglobulin light chain is not required in the immunoadhesins of the present invention, an immunoglobulin light chain might be present either covalently associated to a PSTPIP-immunoglobulin heavy chain fusion polypeptide, or directly fused to the PSTPIP polypeptide. In the former case, DNA encoding an immunoglobulin light chain is typically coexpressed with the DNA encoding the PSTPIP-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Method suitable for the preparation of such structures are, for example, disclosed in U.S. Pat. No. 4,816,567 issued Mar. 28, 1989.

In a preferred embodiment, the immunoglobulin sequences used in the construction of the immunoadhesins of the present invention are from an IgG immunoglobulin heavy chain constant domain. For human immunoadhesins, the use of human IgG-1 and IgG-3 immunoglobulin sequences is preferred. A major advantage of using IgG-1 is that IgG-1 immunoadhesins can be purified efficiently on immobilized protein A. In contrast, purification of IgG-3 requires protein G, a significantly less versatile medium. However, other structural and functional properties of immunoglobulins should be considered when choosing the Ig fusion partner for a particular immunoadhesin construction. For example, the IgG-3 hinge is longer and more flexible, so it can accommodate larger 'adhesin' domains that may not fold or function properly when fused to IgG-1. While IgG immunoadhesins are typically mono- or bivalent, other Ig subtypes like IgA and IgM may give rise to dimeric or pentameric structures, respectively, of the basic Ig homodimer unit. Multimeric immunoadhesins are advantageous in that they can bind their respective targets with greater avidity than their IgG-based counterparts. Reported examples of such structures are CD4-IgM (Trauneckeret al., supra); ICAM-IgM (Martin et al., *J. Virol.* 67:3561–68 [1993]); and CD2-IgM (Arulanandam et al., *J. Exp. Med.* 177:1439–50 [1993]).

For PSTPIP-Ig immunoadhesins, which are designed for in vivo application, the pharmacokinetic properties and the effector functions specified by the Fc region are important as well. Although IgG-1, IgG-2 and IgG-4 all have in vivo half-lives of 21 days, their relative potencies at activating the complement system are different. IgG-4 does not activate complement, and IgG-2 is significantly weaker at complement activation than IgG-1. Moreover, unlike IgG-1, IgG-2 does not bind to Fc receptors on mononuclear cells or neutrophils. While IgG-3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG-l has only four serologically-defined allotypic sites, two of which (G1m and 2) are located in the Fc region; and one of these sites G1ml, is non-immunogenic. In contrast, there are 12 serologically-defined allotypes in IgG-3, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

PSTPIP-Ig immunoadhesins are most conveniently constructed by fusing the cDNA sequence encoding the PSTPIP portion in-frame to an Ig cDNA sequence. However, fusion to genomic Ig fragments can also be used (see, e.g. Gascoigne et al., *Proc. Natl. Acad. Sci. USA* 84:2936–2940 [1987]; Aruffo et al., *Cell* 61:1303–1313 [1990]; Stamenkovic et al., *Cell* 66:1133–1144 [1991]). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques.

H. Anti-PSTPIP Antibody Preparation (i) Polyclonal antibodies

Polyclonal antibodies to a PSTPIP molecule generally are raised in animals by multiple subcutaneous (sc) or intraperitoneal (ip) injections of the PSTPIP and an adjuvant. It may be useful to conjugate the PSTPIP or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to ¹/₁₀ the original amount of conjugate in Freund's complete adjuvant by subcutaneous injection at multiple sites. 7 to 14 days later the animals are bled and the serum is assayed for anti-PSTPIP antibody titer. Animals are boosted until the titer plateaus. Preferably, the animal boosted with the conjugate of the same PSTPIP polypeptide, but conjugated to a different protein and/or through a different cross-linking reagent. Conjugates also can be made in recombinant cell culture as protein fusions. Also, aggregating agents such as alum are used to enhance the immune response.

(ii) Monoclonal antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-PSTPIP monoclonal antibodies of the present invention may be made using the hybridoma method first described by Kohler & Milstein, *Nature* 256:495 (1975), or may be made by recombinant DNA methods [Cabilly et al., U.S. Pat. No. 4,816,567].

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, *Monoclonal Antibodies: Principles and Practice*, pp.59–103 (Academic Press, 1986)]. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, California USA, and SP-2 cells available from the American Type Culture Collection, Rockville, Md. USA. Human myeloma and mouse-human heteromyeloma cell lines also have been described for the production of human monoclonal antibodies [Kozbor, *J. Immunol.* 133:3001 (1984); Brodeur et al., *Monoclonal Antibody Production Techniques and Applications,* pp.51–63 (Marcel Dekker, Inc., New York, 1987)].

Culture medium in which hybridoma cells are growing is assayed for production of monoclonal antibodies directed against a PSTPIP polypeptide. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson & Pollard, *Anal. Biochem.* 107:220 (1980).

After hybridoma cells are identified that produce antibodies of the desired specificity, affinity, and/or activity, the clones may be subcloned by limiting dilution procedures and grown by standard methods. Goding, *Monoclonal Antibodies: Principles and Practice,* pp.59–104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al., *Proc. Nat. Acad. Sci.* 81:6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-PSTPIP monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a PSTPIP polypeptide and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; biotin or an enzyme, such as alkaline phosphatase, β-galactosidase or horseradish peroxidase.

Any method known in the art for separately conjugating the antibody to the detectable moiety may be employed, including those methods described by Hunter et al., *Nature* 144:945(1962); David et al., *Biochemistry* 13:1014(1974); Pain et al., *J. Immunol. Meth.* 40:219 (1981) and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques,* pp.147–158 (CRC Press, Inc., 1987).

Competitive binding assays rely on the ability of a labeled standard (which may be a PSTPIP polypeptide or an immunologically reactive portion thereof) to compete with the test sample analyte (PSTPIP) for binding with a limited amount of antibody. The amount of PSTPIP polypeptide in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat No. 4,376, 110. The second antibody may itself be labeled with a detectable moiety (direct sandwich assays) or may be measured using an anti-immunoglobulinantibody that is labeled with a detectable moiety (indirect sandwich assay). For example, one type of sandwich assay is an ELISA assay, in which case the detectable moiety is an enzyme.

(iii) Humanized antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature* 321:522–525 (1986); Riechmann et al., *Nature* 332:323–327 (1988); Verhoeyen et al., *Science* 239:1534–1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

Alternatively, it is now possible to produce transgenic animals (e.g. mice) that are capable, upon immunization, of producing a fill repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90:2551–255 (1993); Jakobovits et al., *Nature* 362:255–258 (1993).

(iv) Bispecific antibodies

Bispecific antibodies are monoclonal, preferably human or humanized, antibodies that have binding specificities for at least two different antigens. In the present case, one of the binding specificities is for a PSTPIP polypeptide, the other one is for any other antigen. Methods for making bispecific antibodies are known in the art.

Traditionally, the recombinant production of bispecific antibodies is based on the coexpression of two immunoglobulin heavy chain-light chain pairs, where the two heavy chains have different specificities (Millstein and Cuello, *Nature* 305:537–539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication NO. WO 93/08829 (published May 13, 1993), and in Traunecker et al., *EMBO J.* 10:3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, and second and third constant regions of an immunoglobulin heavy chain (CH2 and CH3). It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in PCT application WO 94/04690 published Mar. 3, 1994.

For further details of generating bispecific antibodies see, for example, Suresh et al., *Methods in Enzymology* 121:210 (1986).

(v) Heteroconjugate antibodies

Heteroconjugate antibodies are also within the scope of the present invention.

Heteroconjugate antibodies are composed of two covalently joined antibodies. Such antibodies have, for example, been proposed to target immune system cells to unwanted cells (U.S. Pat. No. 4,676,980),and for treatment of HIV infection(PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

I. Peptide and Non-Peptide Analogs of PSTPIP Polypeptides

Peptide analogs of the PSTPIP polypeptides of the present invention are modeled based upon the three-dimensional structure of the native polypeptides. Peptides may be synthesized by well known techniques such as the solid-phase synthetic techniques initially described in Merrifield, *J. Am. Chem. Soc.* 15:2149–2154 (1963). Other peptide synthesis techniques are, for examples, described in Bodanszky et al., *Peptide Synthesis*, John Wiley & Sons, 2nd Ed., 1976, as well as in other reference books readily available for those skilled in the art. A summary of peptide synthesis techniques may be found in Stuart and Young, *Solid Phase Peptide Synthesis*, Pierce Chemical Company, Rockford, Ill. (1984). Peptides may also be prepared by recombinant DNA technology, using a DNA sequence encoding the desired peptide.

In addition to peptide analogs, the present invention also contemplates non-peptide (e.g. organic) compounds which display substantially the same surface as the peptide analogs of the present invention, and therefore interact with other molecules in a similar fashion.

J. Use of the PSTPIP Polypeptides

The PSTPIP polypeptides of the present invention are useful for a variety of purposes. For example, the PSTPIP polypeptide shown in FIG. 1A is useful for identifying and isolating a PSTPIP homologue in another mammalian species. Native PSTPIP polypeptides and their functional equivalents are also useful in screening assays to identify antagonists or agonists of the native PSTPIP polypeptide. Such assays may take the form of any conventional cell-type or biochemical binding assay, and can be performed in a variety of different assay formats well known to those skilled in the art.

The PSTPIP polypeptides of the present invention are shown herein to be involved with the polymerization of actin monomers in eukaryotic cells. As such, the PSTPIP polypeptides are useful in a variety of indications wherein the skilled artisan wishes to induce the polymerization of actin monomers.

The PSTPIP polypeptides of the present invention and the nucleic acids encoding them are also useful as molecular markers of the tissues in which they are specifically expressed. As such, the PSTPIP polypeptides and nucleic acids encoding them are useful for tissue typing of specific mammalian tissues.

The PSTPIP polypeptides of the present invention are also useful as protein molecular weight markers on protein gels.

Nucleic acids encoding the PSTPIP polypeptides of the present invention are also useful for the preparation of PSTPIP polypeptides by recombinant techniques exemplified herein and in providing hybridization probes for searching cDNA and genomic libraries for the coding sequence of other PSTPIP polypeptides analogs in other species.

Antagonists of the PSTPIP polypeptides of the present invention are useful for inhibiting at least one biological activity of the polypeptides.

Further details of the invention are illustrated in the following non-limiting examples.

The PSTPIP polypeptides of the present invention can also be used in in vitro assays together with PTP HSCF, to identify inhibitors of the PTP-PSTPIP interaction. Such inhibitors may, for example, be polypeptides, peptides or small (organic) molecules, which inhibit the PTP-PSTPIP interaction by binding to PSTPIP and/or to PTP HSCF. Similar assays can be used to find enzymatic inhibitors of dephosphorylation of the phosphatase. Such inhibitors may be useful as chemotherapeutic agents, which are able to stop or inhibit the cell division of tumor cells.

Mutants (amino acid sequence variants) of native PSTPIP polypeptides can be used in vivo in transfected recombinant host cells to identify other components of the cell divisional machinery. In addition, regions of PSTPIP can be used in vivo in the yeast two-hybrid system, or in any functionally similar assay configuration, to identify other interacting proteins potentially involved with cell division.

Antibodies specifically binding PSTPIP can be used, for example, to identify rapidly dividing cells, which, in turn, are used to image tumors comprised of such rapidly dividing cells.

Nucleic acid ancoding native PSTPIP molecules can be used to isolate homologous genes specifically expressed in tumor cells, which might provide more specific targets for tumor therapy.

K. Materials and Methods

1. Two-Hybrid Screening Assay

The yeast two-hybrid screening assay was performed essentially as described (Chien et al., Proc. Natl. Acad. Sci. USA 88:9578–9582 (1991) and Bartel et al., Methods Enzymol 254:241–263 (1995)). A $C_{221}$-S active site mutant of PTP HSCF (Cheng et al., (1996) supra) was cloned in frame with the Gal4 binding domain in the plasmid pPC97. A library of $6\times10^6$ individual clones was produced from Baf3 lymphoid progenitor cells in the Gal4 activation domain plasmid pPC86 using standard procedures. Yeast were transformed with both plasmids and were incubated on histidine minus plates for 3 days at 30° C. Colonies which grew under these conditions were restreaked onto histidine minus plates and were tested for β-galactosidase activity (Bartel et al., (1995) supra). Colonies which manifested various levels of β-galactosidase activity were isolated, and the cDNA inserts in the pPC86 vector were isolated by PCR and sequenced using standard procedures. Clones encoding PSTPIP were tested for dependence on the PTP interaction by transfection into cells with and without the original PTP HSCF containing pPC97 plasmid and subsequent analysis for growth on histidine minus plates and β-galactosidase activity.

2. Mapping of Interaction Domains

To obtain a cDNA encoding full-length PSTPIP tagged with the FLAG epitope (DYKDDDDK) (SEQ ID NO:8) at the C-terminus, PCR was performed using primers 48.BAMHI.F (CGCGGATCCACCA TGATGGCCCAGCTGCAGTTC) (SEQ ID NO:9) and 48.SALFLAG.R (GTACGCGTCGACTCACTTGTCATCGTCGTCC TTGTAGTCGAGCTT)(SEQ ID NO:10). The resulting PCR fragment was digested with BamHI and Sal I and subcloned into the BamHI and Sal I sites of pRK.tkneo, an expression plasmid containing the cytomegalovirus promoter, thus creating plasmid pRK.PIP.FLAG.C. The PTP HSCF deletion mutants were derived from a construct containing the influenza hemagglutinin epitope at its N-terminus and were made as follows: PCR was performed on PRK.HSCF using primers prkr (TGCCTTTCTCTCCACAGG) (SEQ ID NO:11) and 38.spe.mid.R (CTCCTTGAGGTTCTACTAGTGGGGG CTGGTGTCCTG) (SEQ ID NO: 12). The resulting PCR fragment encoding the phosphatase domain (amino acids 1–312) was digested with Cla I and Spe I and subcloned into pRK.tk.neo digested with Cla I and Xba I resulting in plasmid pRK.hscf.ptp domain. Similarly, PCR using primers prkr and 39.spe endR (GCGGCCGCACTAGTATCCAGTCTG TGCTCCATCTGTTAC) (SEQ ID NO:13) was performed and the resulting fragment encoding amino acids 1–439 of hscf was digested with Cla I and Spe I and subcloned into the Cla I and Xba I sites of pRKtkneo. GST fusion proteins were prepared essentially according to the manufacturer (Pharmacia Biotech) in DH5-alpha bacterial cells. A Sal I to Not I fragment containing the full-length cDNA for PSTPIP (amino acids 2–415) was subcloned into pGEX-4T-2 (Pharmacia) cleaved at the Sal I and Not I sites.

To obtain a DNA fragment encoding the coiled-coil domain of PST?IP, PCR was performed using primers PC86F (GCGTTTGGAATCA CTAC) (SEQ ID NO:14) and pip48.1706R (TTATAGTTTAGCGGCCGCTCACCGGTAGTCCTGGG CTGATG) (SEQ ID NO:15). The PCR fragment was digested with Sal I and Not I and subsequently cloned into the Sal I and Not I sites of pGEX-4T-2.

To obtain a cDNA fragment encoding the SH3 domain of PSTPIP, PCR was performed using primers pip48.1673.F (GTACGCGTCGACC GCACTCTACGACTACACTGCACAG) (SEQ ID NO:16) and PC86R 20 (CTCTGGCGAAGAAGTCC) (SEQ ID NO:17) and the resulting product was digested with Sal I and Not I and subcloned into the Sal I and Not I sites of pGEX-4T-2. To obtain a cDNA fragment encoding the PST (and C-terminal homology) of PTP HSCF (amino acids 304–453), PCR Was performed using primers PST38-RI (GATCGAATTCCCAGAACCTCAA GGAGAACTGC) (SEQ ID NO:18) and PST38-XHOI (GATCCTCGAGTTACACCCGTGTCCACTCTGCTGGA GGA) (SEQ ID NO:19). The resulting PCR product was digested with EcoRI and Xhol and subcloned into the EcoRI and Sal sites of pGEX-4T-2. Protein determinations were carried out according to the Couprus assay with a kit from Geno Technology (St Louis).

The binding was carried out according to the method of Wong and Johnson (Wong et al., *J. Biol. Chem.* 271(35) :20981–20984(1996)). Briefly, 1 µg of plasmid with either the PSTPIP protein or PTP HSCF under the control of the Sp6 promoter was in vitro transcribed/translated using the Promega TnT Rabbit Reticulocyte system. Samples were diluted in 50 mM HEPES, pH 7.2, 1% triton X 100, 10% glycerol, 100 mM NaCI, 5 mM EDTA and 2 µg/ml each of leupeptin, pepstatin, aprotinin, and PMSF. Samples were pre-cleared with resin for 1 hour and 1 µg GST-fusion protein was added along with 30 µl of GSH-Sepharose that was previously blocked in 3% BSA for 1 hour. This was reacted for 1 hour at 4° C. and then the resin washed 6 tines in HEPES/Triton binding buffer before SDS gel electrophoresis. The peptides were synthesized on an automated Milligen 9050 Peptide Synthesizer using standard solid phase chemistry with FMOC protected amino acids on a p-alkoxybenzyl alcohol resin. Dried peptides were re-suspended in the HEPES/Triton Binding buffer at a concentration of 10 mg/ml. Peptide inhibition was performed by adding the peptide first to the in vitro translation product and then the GST-fusion followed by the GSH-Sepharose. The binding/washing steps were as previously described. The peptides synthesized and the PTPs they were derived from were:

PXXP-HSCF: $_{432}$GFNLRIGRPKGPRDPPAEWT$_{451}$ (PTP HSCF) (SEQ ID NO:20),

PXXP-PEP: $_{782}$GFGNRFSKPKGPRNPPSAW$_{800}$ (PTP PEP) (SEQ ID NO:21),

PXXP-PEST: $_{761}$GFGNRCGKPKGPRDPPSEWT$_{780}$ (PTP PEST) SEQ ID NO:22),

PXXP-CONTROL: $_{334}$GGVLRSISVPAPPTLP-MADT$_{353}$ (PTP HSCF) (SEQ ID NO:23).

3. Analysis of Tyrosine Phosphorylation

Baf3 cells were lysed in 1% Triton, 50 mM HEPES, 10% glycerol and 5 mM EDTA containing 1 µg/ml aprotinin, PMSF, leupeptin and pepstatin with 1 mM Sodium Vanadate and 10 mM Iodoacetic acid. Cells were treated with 0.1 mM Pervanadate for 4 hours before lysis. Immunoprecipitations were performed in the vanadate-containing lysis buffer using 1 µg/ml anti-PSTPIP polyclonal antibody and 400 µg of lysate protein at 4° C. overnight. Western blots were performed using 1 µg/ml affinity purified anti-PSTPIP or 1:5000 dilution of commercial 4G10 anti-phosphotyrosine monoclonal (Upstate Biotech). Signal was detected by HRPO-ECL reagents (Pierce). The $C_{221}$-S mutant was as previously described (Cheng et al., (1996supra). The PTP HSCF $D_{197}$-A mutant was generated using PCR. Mutagenesis primer D197A.F (GTATATGTCCTGGCCAGCCCATGGGGTTCCCAGCA G) (SEQ ID NO:24), corresponding to nucleotide 591, and primer D197A.R (GCAGGTCGACTCTAGATTACACCCGTGTCCACTCT G) (SEQ ID NO:25) which corresponds to the stop codon, were used in PCR to generate a fragment that could be cut with Mscl and Xbal. pRK.HA.38 WT, a plasmid which encoded the wild type enzyme under the control of the cytomegalovirus promoter(Cheng et al., (1996) supra), was digested with Clal and Mscl and the resulting 600 bp fragment was ligated with the Mscl-Xbal PCR fragment into the Clal and Xbal sites of pRK.tkneo. A plasmid encoding the V-src oncogene under the control of the SV40 early promoter was the kind gift of Dr. Art Levinson (CEO-Genentech, Inc.). NIH 3T3 cells and COS-7 cells were cultured in high glucose DMEM supplemented with 10% FBS, 2 mM L-Glutamine, 10 mM HEPES pH 7.2 and pen-strep.

COS-7 cells were transfected by electroporation. Briefly, $1.5 \times 10^6$ COS-7 cells were mixed with 24 µg total DNA in PBS and electroporated at 960 µF, 0.22 volts (Bio-Rad Gene Pulsar). Following electroporation, cells were seeded in 10cm dishes and incubated for 3 days. 10-cm dishes of transfected COS cells were washed twice with ice-cold PBS, and lysed in 1 ml of M-RIPA (50 mM Tris 7.4, 1% NP40, 0.25% DOC, 150 mM NaCI, 1 mM sodium ortho-vanadate, 1 mM NaF plus Complete™ Protease Inhibitors (Boehringer Mannheim)). Lysates were incubated for 15 minutes with 100 µl UltraLink Immobilized Protein A/G (Pierce) at 4° C., followed by centrifugation for 5 minutes. Supernatants were collected and stored at −70° C. or directly immunoprecipitated. 5 µg of M2 or 12CA5 was added to 500 µl of lysate and incubated overnight at 4° C. Ultralink Protein A/G was added and incubation continued for 2 hours at 4° C. The immune complexes were washed 3 times with M-RIPA. The proteins were subjected to SDS-PAGE and transferred to nitrocellulose 1× Transfer Buffer (Novex). Immunoblots were blocked overnight at 4° C. in 3% milk/PBS. To detect Flag-tagged PIP, blots were incubated with 10 µg/ml Bio-M2 (Biotinylated anti-FLAG monoclonal Ab, KODAK) followed by incubation in 10 µg/ml streptavidin-HRP (UBI). To detect HA-tagged PTPhscf, blots were incubated in anti-(HA)-peroxidase(Boehringer Mannheim) as per manufacturer's instructions. To detect phosphotyrosine, blots were incubated in HRP-conjugated 4G10 (anti-phosphotyrosine monoclonal, UBI) as per manufacturer's instructions.

4. Confocal Microscopy of Endogenous and Translated PSTPIP.

Rabbit polyclonal antibodies were produced against a GST-PSTPIP fusion protein. The complete PSTPIP-GST fusion protein was purified on GSH-sepharose and injected intramuscularly at 2 sites with 200 µg fusion protein and subcutaneously at multiple sites with a total of 300 µg PSTPIP-GST fusion protein in Complete Freunds Adjuvant. Rabbits were boosted every 3 weeks with 100 µg fusion protein in Incomplete Freunds. 15 ml of rabbit sera was reacted with 0.5 mg PSTPIP-GST-GSH-Sepharose for 3 hours at 4° C. with gentle rotation. The resin was collected by centrifugation and washed with 10 column volumes of PBS. Immunoglobulin was eluted from the affinity matrix with 100 mM acetic acid, 500 mM NaCl, neutralized with NaOH, and then dialyzed overnight with PBS. NIH 3T3 cells were seeded at 100,000 cells per chamber slide and allowed to adhere overnight.

The cells were transfected using Lipofectamine(2 ug pRK.PIP.FLAG.C/12 ul Lipofectamine in 0.8 ml OPTI-MEM) for 5 hours. The DNA/Lipofectamine solution was removed and fresh serum containing medium added. 48 hours following the start of transfection, the cells were fixed in 4% formaldehyde in PHEM 6.1 (60 mM PIPES, 25 mM HEPES, 10 mM EGTA and 2 mM $MgCl_2$) for 20 minutes, then permeabilized in 0.2% Triton X-100, 300 mM sucrose in PHEM 6.9 for 10 minutes. The cells were washed twice in PHEM 6.9 and then incubated with 10% FBS/PHEM 6.9 for 1 hour to block non-specific binding of the antibody.

Cells were incubated for 1 hour in 2% BSA/PHEM 6.9 containing 10 μg/ml M2 (KODAK, anti-FLAG monoclonal antibody) or 10 μg/ml 12CA5 (Boehringer Mannheim anti-HA monoclonal antibody) as an irrelevant antibody control. After washing cells twice with 2% BSA/PHEM6.9, cells were incubated with for 30 minutes with a 1:2000 dilution of Cy3-conjugated AfinniPure sheep anti-mouse IgG and a 1:200 dilution of Fluorescein Phalloidin (Molecular Probes) in 2% BSA/PHEM 6.9. Cells were washed in 2% BSA/PHEM6.9 and mounted in Vectashield Mounting Medium with DAPI. NIH3T3 cells were seeded at 200,000 cells per chamber slide and allowed to adhere overnight. Cells were stained with 0.4 μg/ml rabbit anti-PIP or 0.4 μg/ml rabbit IgG and detected with Cy3-conjugated goat anti-rabbit. Additionally, cells were co-stained with a 1:200 dilution of Fluorescein-Phalloidin.

L. EXAMPLES

Example 1

Identification of a PTP HCSF Binding Protein

In order to identify potential substrates for PTP HSCF (Cheng et al., (1996) supra), we performed a yeast two-hybrid screening assay using a catalytically inactive form of the enzyme as bait and a library derived from murine Baf3 hematopoietic progenitor cells, a cell type that has been previously demonstrated to express high levels of this phosphatase (Cheng et al., (1996), supra). This resulted in the isolation of approximately 70 yeast clones which grew in the absence of histidine and which expressed variable levels of β-galactosidase. Sequence analysis of the clones revealed that approximately 40% encoded related sequences with slightly divergent 5' fusions with the Gal 4 DNA-binding domain. The sequences of the remainder of the clones suggested that they were likely due to artefactual interactions. Analysis of histidine growth and β-galactosidase expression of all two-hybrid clones containing these related sequences revealed an absolute dependence on the inclusion of the phosphatase bait construct in the same cells (data not shown). The longest two hybrid clone was used to isolate a full length cDNA from the original Baf3 two hybrid library.

FIG. 1A illustrates that the protein which interacts with PTP HSCF is a novel 415 residue molecule (predicted molecular weight ~47,590 D) (SEQ ID NO:1) with significant sequence homology to the S. pombe cell cycle protein, CDC15p (SEQ ID NO:26), a cytoskeletal interacting protein involved with organization of the actin ring at the cleavage furrow during cytokinesis (Fankhauser, Cell 82:435–444 (1995)). This homology (~26% sequence similarity) stretches over the entire length of both molecules, with the exception of a large insertion of approximately 500 residues in the yeast molecule that is not found in the mammalian protein, and the yeast protein is the highest scoring homologue in the protein sequence database.

A number of features are conserved in these two proteins. For example, both have an SH3 domain at their carboxy termini (Feng et al., Proc. Natl. Acad. Sci. USA 92:12408–12415 (1995) and Pawson, (1995) supra), and the mammalian SH3 domain appears to be homologous to those found in a number of known cytoskeletal regulatory proteins including myosin heavy chain, spectrin, fodrin, hematopoietic specific protein 1 (HS 1) and the p80/85 src substrate, cortactin (FIG. 1B). In addition, both the mammalian and yeast (Fankhauser, (1995) supra) proteins contain a potential coiled coil domain at their N-termini which is predicted both on the basis of sequence homology as well as an analysis of the mammalian sequence using the Prostruct program (FIG. 1 C). Within these coiled coil domains is a region with an extraordinary content of acidic and basic residues (positions 99–180 of the mammalian protein). Because the mammalian protein was isolated on the basis of an interaction with a tyrosine phosphatase, it is possible that the protein is tyrosine phosphorylated (see below), and examination of the mammalian and yeast sequences revealed 5 conserved tyrosine residues (positions 53, 191, 287, 367 and 369 of the mammalian protein). Finally, examination of the proteins for proline rich regions which might function as SH3 binding sites (PXXP) (SEQ ID NO:27) revealed two such conserved sites in these proteins (starting at positions 278 and 323 of the mammalian protein) (Feng et al., (1995) supra and Pawson, (1995) supra). p80/85 cortactin (Wu et al., Mol. Cell. Biol. 11:5113–5124(1991)) and HS1 (Kitamura et al., Nuc. Acids. Res. 17:9367–9379 (1989)) are two other mammalian proteins that contain repeated coiled coil and SH3 domains and that bear a more distant relationship to the PTP HSCF interacting protein, although these two proteins contain homologous 37 amino acid repeats in their coiled coil regions which appear to be absent from the PTP interacting protein. Because the mammalian sequence was isolated based upon its ability to interact with the PEST phosphatase PTP HSCF, it has been termed PSTPIP (PST Phosphatase Interacting Protein).

Figure 2B:
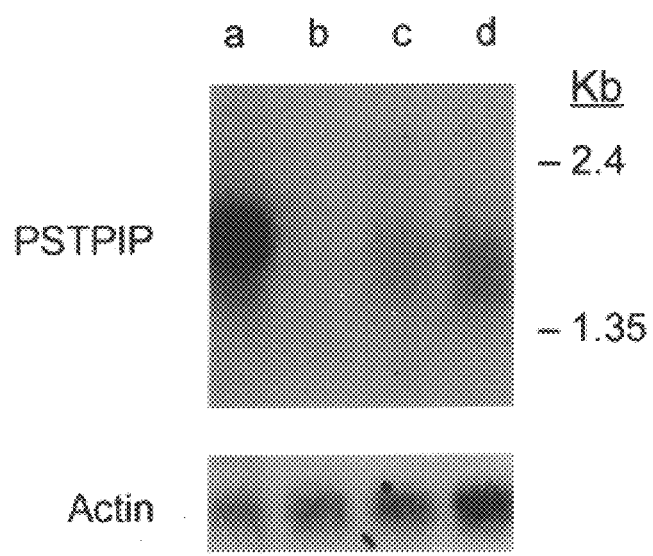

Northern blot analysis of the expression of PSTPIP during embryogenesis and in adult tissues is illustrated in FIG. 2. Interestingly, the protein is more highly expressed in the very early 7 day embryo as compared to later stages, and it appears to be significantly downregulated in the 11 day embryo (FIG. 2B). The protein is expressed at relatively high levels in adult lung and spleen and at lower levels in testis, muscle, kidney, brain and heart (FIG. 2A). However, the interacting protein is at far lower levels than actin, since the actin blots were exposed for 4 hours versus the one week exposure for the PSTPIP blots. Previously, we and others have demonstrated that PTP HSCF is also expressed at detectable levels in both adult lung and kidney (Cheng et al., (1996) supra and Huang et al., (1996) supra).

Example 2

Characterization of the Interaction Between PTP HSCF and PSTPIP

Figure 3:
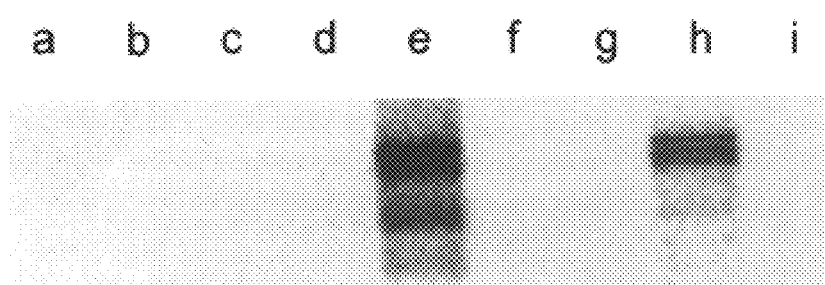
FIG. 3. Interaction Between PTP HSCF and GST-PSTPIP. Shown are precipitations of in vitro transcribed and translated PTP HSCF phosphatase with GST-p85 (lane a), GST alone (lane b), GST-Src (lane c), GST-Grb-2 (lane d), GST-PSTPIP (lane e), GST-Abl (lane f), GST-PLC (lane g), anti-PTP HSCF polyclonal antibody (lane h) and GST-Spectrin (lane i).

In order to characterize the regions involved with the binding between PTP HSCF and PSTPIP, a rapid and direct in vitro binding assay was performed. In this assay, various GST fusions of either the phosphatase or the interacting protein were used to precipitate in vitro translation products of the cognate binding proteins. FIG. 3 illustrates that precipitation of in vitro translated PTP HSCF by GST fusion proteins containing various SH3 domains as well as full length PSTPIP revealed a high degree of specificity in the interaction between the GST PSTPIP and the phosphatase. FIG. 3 also illustrates that at this concentration of GST fusion protein (~1 microgram per ml or ~1.5 micromolar), the PSTPIP fusion protein appeared to be more efficient at precipitating the phosphatase than a polyclonal antibody directed against the enzyme or a monoclonal antibody directed against a hemagglutinin tag at the PTP N-terminus (data not shown). This result is consistent with a relatively high affinity interaction between the GST PSTPIP and the in vitro translated PTP HSCF (see below).

Figure 4A:
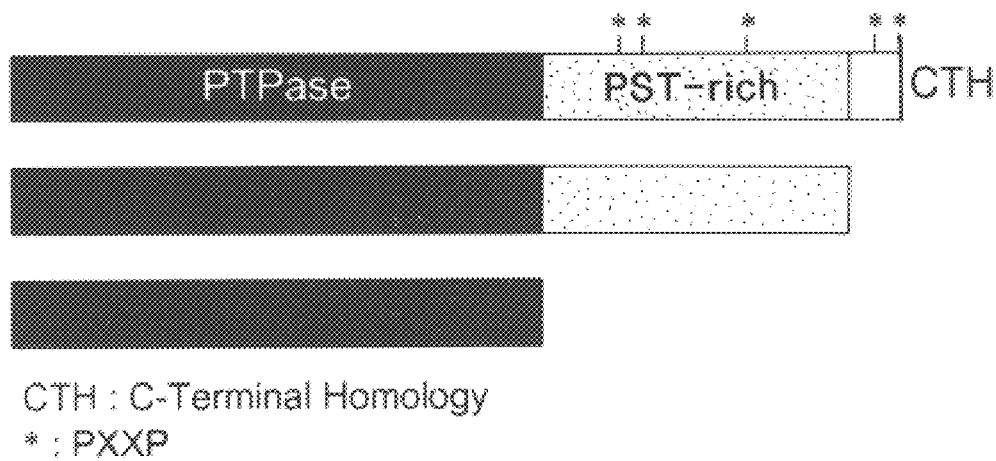
FIGS. 4A–4D. Mapping of the PSTPIP Interaction Site on PTP HSCF. A. Shown are PTP HSCF constructs containing full-length C-terminal homology (CTH) and PST-rich domain deletions used for in vitro transcription and translation. B. Precipitation of in vitro transcribed and translated forms of PTP HSCF with GST-PSTPIP or anti-PTP HSCF polyclonal antibody. Lanes are designated as follows: full-length PTP HSCF with anti-PTP HSCF (lane a), full-length PTP HSCF with GST-PSTPIP (lane b), PST-rich+CTH deleted PTP HSCF with anti-PTP HSCF (lane c), PST-rich+CTH deleted PTP HSCF with GST-PSTPIP (lane d), PST-rich+CTH deleted PTP HSCF with GST-Spectrin (lane e), CTH-deleted PTP HSCF with GST-Spectrin (lane f), CTH-deleted PTP HSCF with GST-PSTPIP (lane g), CTH-deleted PTP HSCF with anti-PTP HSCF (lane h), full-length PTP HSCF with anti-PTP HSCF (lane i). C. Precipitation of in vitro transcribed and translated PSTPIP with anti-PSTPIP polyclonal antibody (lane a), 10 µg of GST-PST-rich+CTHPTP HSCF (a GST construct containing the PST-rich and CTH domains of the phosphatase) (lane b), 5 µg of GST-PST-rich+CTHPTP HSCF (lane c), 2 µg of GST-PST-rich+CTH PTP HSCF (lane d) or 1 µg of GST-PST-rich+CTHPTP HSCF (lane e). D. Precipitation of in vitro transcribed and translated PSTPIP with GST-PST-rich+CTH PTP HSCF in the presence of increasing amounts of proline rich peptides derived from the C-terminal homology regions of PTPs HSCF, PEST and PEP or a control proline rich peptide from PTP HSCF.
Figure 4B:
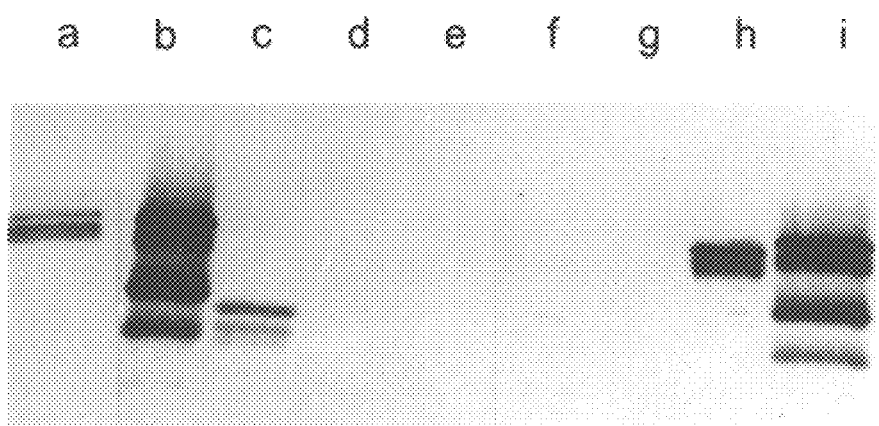
Figure 4C:
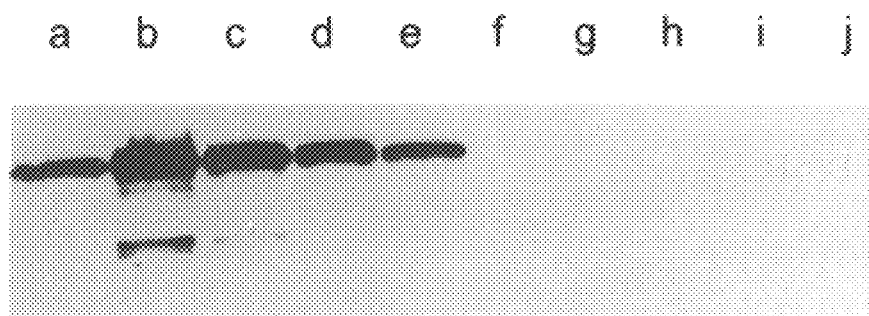
Figure 4D:
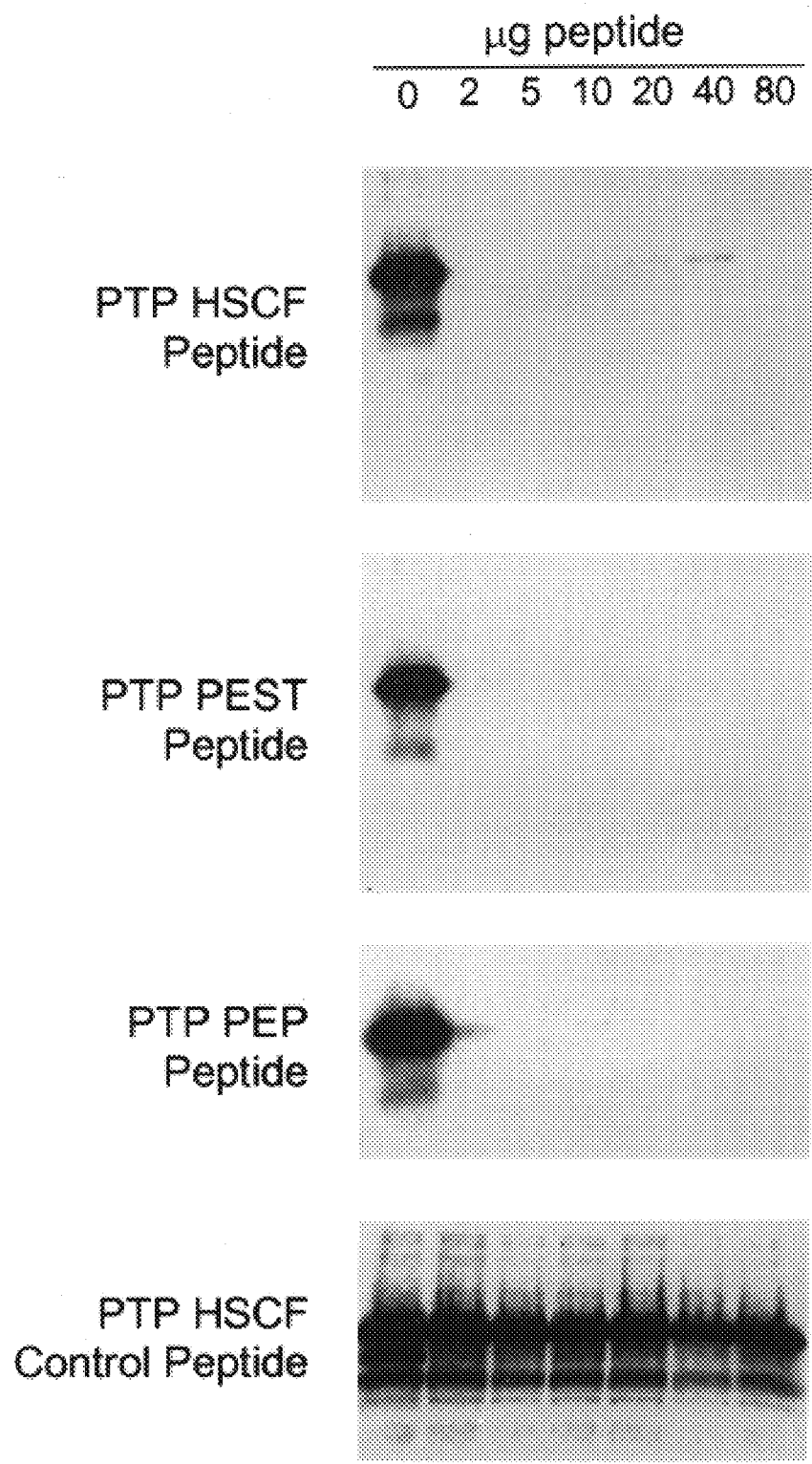
Figure 5A:
FIGS. 5A–5B. Mapping of PTP HSCF Interaction Site on PSTPIP. A. Shown are GST fusions containing the full-length, coiled coil and SH3 domains of PSTPIP. B. Precipitation of full-length PTP HSCF with GST-full-length PSTPIP (lane a), anti-hemagglutinin (directed against a hemagglutinin epitope tag at the N-terminus of the PTP HSCF) (lane b), GST-Grb2 (lane c), GST-Spectrin (lane d), GST-full-length PSTPIP (lane e), GST-SH3 PSTPIP (lane f) and GST-coiled coil PSTPIP (lane g).
Figure 5A:
Figure 5A:
Figure 5B:
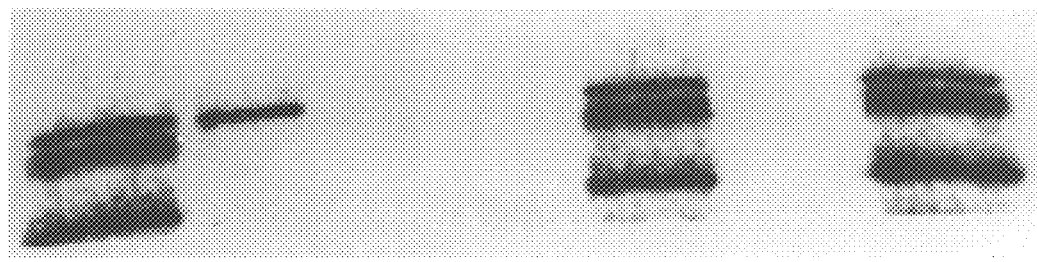
Figure 6A:
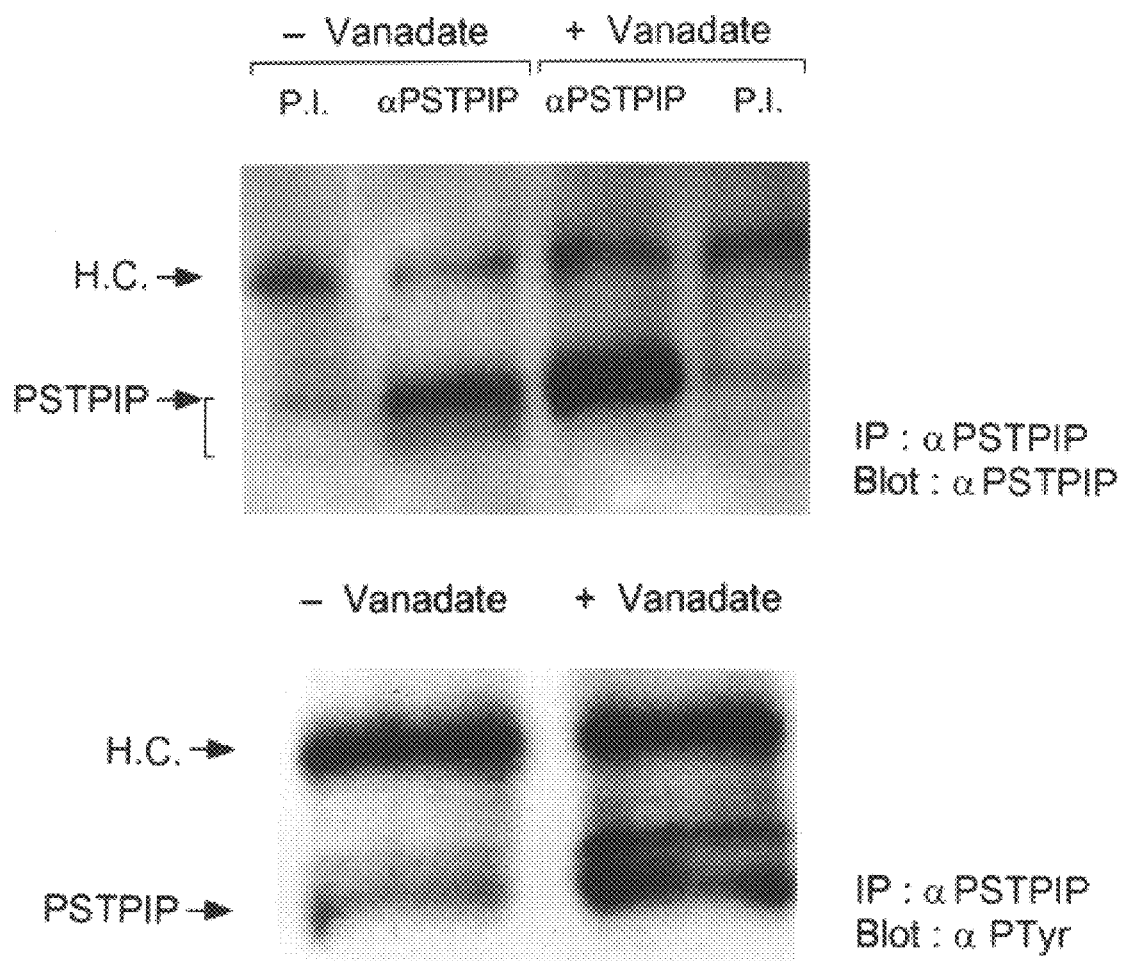
Figure 6F:
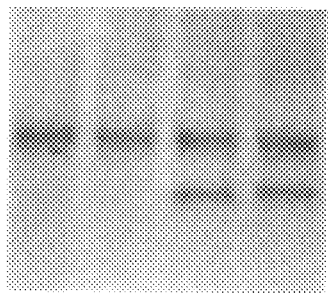
Figure 6F:
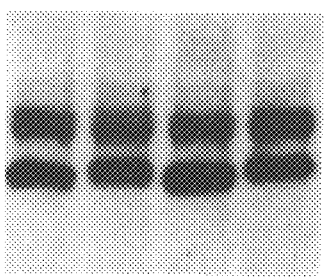
Figure 6F:
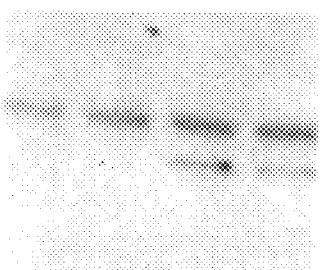
Figure 6F:
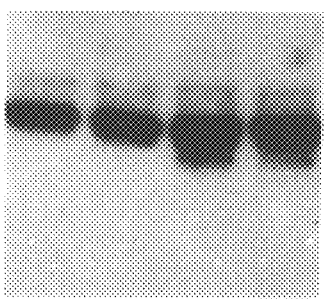
Figure 7A:
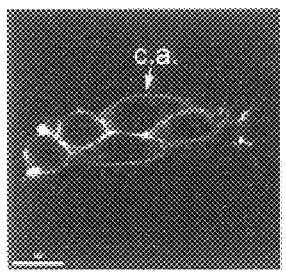
FIGS. 7(A–G). Localization of Endogenous PSTPIP in 3T3 Cells. Shown are confocal images of two different groups of 3T3 cells viewed at different focal planes stained with anti-PSTPIP antibody (Cy3) and phalloidin-FITC (panels a–d). Sites of colocalization appear yellow and are the cortical actin (c.a.), the lamellipodia (lam.) and the stress fibers (s.f.). Panels e–g illustrate a lower magnification and two high magnification views, respectively, of interphase cells and cells undergoing cytokinesis stained with the same reagents. The interphase cells show co-localization predominantly in the cortical actin (c.a) region at this focal plane, while the cells undergoing cytokinesis show colocalization predominantly at the cleavage furrow (c.f.) at both focal planes shown. The bars show sizes in microns.
Figure 7B:
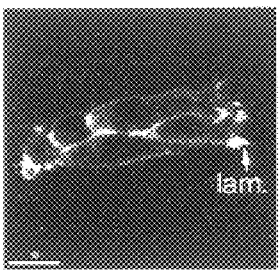
Figure 7C:
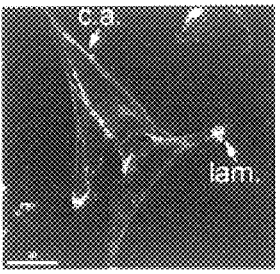
Figure 7D:
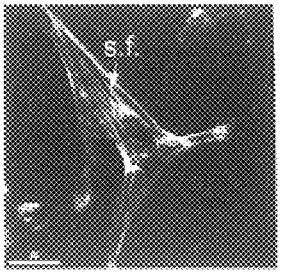
Figure 7E:
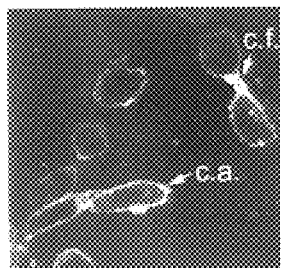
Figure 7F:
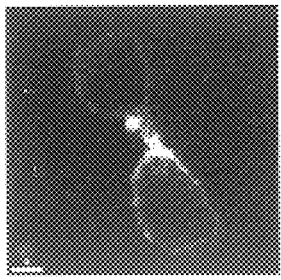
Figure 7G:
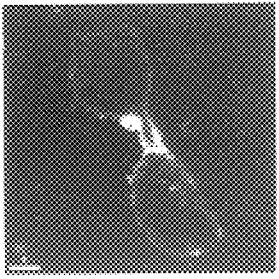

The region of PTP HSCF which interacts with PSTPIP was identified by producing deletion mutants of the enzyme missing either the 20 amino acid C-terminal domain which is highly conserved in all of the PEST PTPs (Yang et al., (1993) supra Matthews et al., (1992) supra, Cheng et al., (1996) supra, Huang et al., (1996) supra, Aoki et al., (1996) supra, Dosil et al., (1996) supra and Kim et al., (1996) supra) or both this domain as well as the longer proline, serine and threonine rich region C-terminal to the catalytic domain (FIG. 4A). FIG. 4B–C reveal that deletion of the C-terminal 20 amino acid homology domain of PTP HSCF completely abolished the interaction between PTP HSCF and PSTPIP. Because this region is conserved in all PEST PTPs, it is possible that both PTP PEST (Yang et al., (1993) supra) as well as PTP PEP (Matthews et al., (1992) supra) also interact with PSTPIP. In order to examine this possibility, as well as to examine if the 20 amino acid C-terminal region is sufficient for this interaction, 20 residue long peptides derived from the homologous C-terminal domain of three PEST PTPs were used to compete with the interaction between PTP HSCF and PSTPIP (FIG. 4D). In this form of the assay, a GST fusion derived from the PST-rich and C-terminal homology regions of the phosphatase was used to precipitate in vitro translated PSTPIP in the presence of varying amounts of peptides.

FIG. 4D illustrates that all three peptides effectively block the interaction at concentrations as low as ~800 nM, while a control peptide derived from a different proline-rich region of PTP HSCF is completely unable to block the interaction. These data suggest that this small proline rich region of the PEST PTPs is sufficient for mediating the high affinity interaction between the phosphatase and PSTPIP, and furthermore indicate the possibility that all of these PTPs may interact with PSTPIP via the C-terminal homology domain.

In order to examine the region of PSTPIP which interacts with the C-terminal homology region, GST fusions containing either the SH3 domain or the coiled coil domain of the interacting protein were used to immunoprecipitate in vitro translated PTP HSCF. The C-terminal homology region which interacts with PSTPIP contains 2 overlapping consensus SH3 (PXXP) (SEQ ID NO:27) binding sites, consistent with the possibility that the phosphatase-PSTPIP interaction was an SH3-type binding event (Pawson, (1995) supra and Feng et al., (1995) supra). However, the affinity of the interaction as measured in the peptide experiment was significantly greater than many of those previously reported for SH3 domain-PXXP (SEQ ID NO:27) interactions (Feng et al., (1995) supra), and as FIG. 5 illustrates, the interaction between these proteins was surprisingly mediated by the coiled coil domain and not the SH3 region. This outcome is consistent with the results of the two hybrid clones, all of which began at a site very close to the N-terminus of the coiled coil domain, suggesting that the PSTPIP site which interacts with the C-terminal proline rich domain includes the N-terminus. Thus, these data define a novel, apparently high affinity interaction between the C-terminal proline rich domain of PTP HSCF and the coiled coil region of PSTPIP.

Example 3

PSTPIP is a Substrate for PTP HSCF Phosphatase Activity

The association between PTP HSCF and PSTPIP suggested that the interacting protein might be a substrate for the phosphatase. In addition, the conservation of a number of tyrosines between PSTPIP and the highly phosphorylated CDC15 protein was also consistent with the possibility that the interacting protein was tyrosine phosphorylated. As FIG. 6 demonstrates, endogenous PSTPIP is indeed tyrosine phosphorylated in Baf 3 cells, and this phosphorylation was significantly enhanced by the tyrosine phosphatase inhibitor vanadate, consistent with the supposition that the protein is dephosphorylated in vivo by a PTP enzyme (Dixon, Ann. NY Acad. Sci 766:18–22 (1995)).

A potential tyrosine kinase which might phosphorylate PSTPIP in vivo is src. Previous data suggested that the V-src tyrosine kinase is associated with the cytoskeleton, modulates cytoskeletal elements which resulted in profound morphological changes (Cooper et al., Cell 73:1051–1054 (1993), Kaplan et al., EMBO J. 13:4745–4756 (1994) and Thomas et al., Nature 376:267–271 (1995)) and mediates the tyrosine phosphorylation of p80/85 cortactin (Wu et al., (1991) supra, Okamura et al., J. Biol. Chem.270 (44):26613–26618 (1995), Vuori et al., J. Biol. Chem. 270(38):22259–22262(1995) and Dehio et al., EMBO J. 14:2741–2782 (1995)), an SH3, coiled coil containing actin binding protein that bore a structural similarity to PSTPIP. In addition, HS 1, another SH3 containing protein that is also structurally similar to PSTPIP, is tyrosine phosphorylated by various SRC-family kinases (Yamanashi et al., Proc. Natl. Acad. Sci. USA 90:3631–3635 (1993), Nada et al., Oncogene 9:3571–3578 (1994), Takemoto et al., EMBO J. 14:3403–3414 (1995) and Takemoto et al., Int. Immunol. 8(11):1699–1705 (1996)). These results implied that V-src, a constitutively active form of the enzyme, might mediate the tyrosine phosphorylation of PSTPIP, thus allowing for an analysis of the possible substrate interactions between the interacting protein and PTP HSCF. In order to test this possibility, PSTPIP was transfected into COS cells together with the V-src tyrosine kinase and either wild type or dominant negative forms of PTP HSCF. Dominant negative phosphatases were produced by mutating either the active site cysteine to a serine ($C_{229}$-S), which abolishes the ability of the enzyme to form a covalent transition state intermediate with the phosphate attached to the tyrosine, or mutation of a critical active site aspartate residue to alanine ($D_{197}$-A), which inhibits the catalytic removal of the phosphate (Dixon, (1995) supra, Jia et al., Science 268(5218):1754–1758 (1995) and Garton et al., (1996) supra). In both cases, these mutants will tightly bind to the substrate but not dephosphorylate it, with the result being that the substrate will be hyperphosphorylated. This procedure has been previously utilized to characterize substrates for a number of different PTPs, including PTP PEST (Garton, (1996) supra) and PTP SHP-2 (Herbst et al., Cell 85:899–909 (1996)), and it has revealed that these mutant enzymes show exquisite substrate specificity in vivo.

As can be seen from FIGS. 6B–F, PSTPIP is tyrosine phosphorylated in response to V-src cotransfection. Transfection of the wild type PTP HSCF into PSTPIP and V-src expressing cells resulted in a decreased level of tyrosine phosphate on the interacting protein, consistent with the in vivo removal of the phosphate from PSTPIP tyrosines by the phosphatase enzyme, a result that would be expected if the interacting protein were a substrate for the enzyme. Even more compellingly, FIGS. 6B–F also illustrates that cotransfection of either dominant negative form of PTP HSCF into PSTPIP and V-src transfected cells resulted in a dramatic increase in the levels of tyrosine phosphate on the interacting protein. It appears that the $D_{197}$-A mutation was a slightly more efficient dominant negative protein than the $C_{229}$-S mutant, consistent with results found using dominant negative forms of PTP PEST interacting with one of its substrates, p130$^{CAS}$ (Garton, (1996) supra).

These results, in addition to the in vitro binding studies, suggest a direct physical interaction between PSTPIP and PTP HSCF, and FIGS. 6B–F also illustrate the in vivo physical association of these proteins by demonstrating the coprecipitation of either PSTPIP or PTP HSCF by antibodies to epitope tags on the cognate binding proteins. These data are thus consistent with the conclusion that PSTPIP interacts with PTP HSCF in vivo, and that this interaction allows the phosphatase to dephosphorylate tyrosine residues modified by the V-src kinase. In addition, because tyrosine phosphorylated PSTPIP was only observed in cells that were transfected with V-src, these data also suggest that COS cells may be deficient in the cellular kinase which tyrosine phosphorylates PSTPIP, or that the dramatic overexpression of the protein in these cells overwhelmed the endogenous tyrosine phosphorylation mechanism.

Example 4

Subcellular Localization of PSTPIP

S. pombe CDC15p is associated with the cortical actin cytoskeleton until it migrates to a region over the postmitotic nucleus and initiates formation of the actin-rich cleavage furrow (Fankhauser, (1995) supra). The protein remains associated with the cleavage furrow until the completion of cell division, when it migrates back to the region of the cell containing cortical actin. In order to analyze the subcellular localization of endogenous PSTPIP, 3T3 cells were stained with an affinity purified polyclonal antibody directed against a GST fusion of the protein and were imaged using confocal microscopy. FIG. 7 illustrates that the interacting protein is colocalized to several actin-containing sites in the cell. A large portion of the protein appears to be associated with the cortical actin cytoskeleton on the intracellular side of the plasma membrane. The protein also appears to co-localize with the actin stress fibers as well as in lamellipodial regions of the cell containing actin.

In addition, transfection of PSTPIP into CHO cells revealed expression at sites of focal contact (data not shown). These results are in contrast with the PSTPIP-related protein p80/85 cortactin, which shows localization on cortical actin and at the ends of the stress fibers but not the fibers themselves (Wu et al., (1991) supra). As is the case with S. pombe CDC15p (Fankhauser, (1995) supra), these data suggest that PSTPIP is associated with cytoskeletal actin during the non-cytokinetic stages of the cell cycle.

Importantly, examination of cells undergoing cytokinesis reveals that endogenous PSTPIP is predominantly associated with the cleavage furrow (Fishkind et al., Current Opinion in Cell Biology 7:23–31 (1995) and Fankhauser, (1995) supra). As FIG. 7 shows, both PSTPIP and the actin ring co-localize to this region of the dividing cells. FIG. 7 also illustrates that the PSTPIP in the cleavage furrow is predominantly associated with the membrane bound F actin which acts to constrict the cleavage furrow (Fishkind, (1995) supra), and examination of sections taken perpendicular to the cleavage furrow support this, showing donut-like structure containing both PSTPIP and actin attached to the constricting plasma membrane of the cleavage furrow (data not shown). It also appears from FIG. 7 that much of the cortically associated actin and PSTPIP migrate to the cleavage furrow during cytokinesis, a result that is remarkably similar to that observed for yeast CDC 1 5p and actin (Fankhauser,(1995) supra). These subcellular localization data are thus consistent with the conclusion that PSTPIP is an actin binding protein that is potentially involved with the regulation of the cleavage furrow.

Example 5

Filopodial Induction by Overexpressed PSTPIP

Figure 8A:
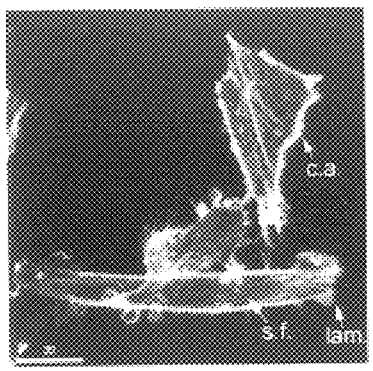
FIGS. 8(A–C). Expression of PSTPIP in Transfected 3T3 Cells. Panel a shows a group of 3T3 cells transfected with an expression plasmid containing a C-terminal FLAG version of PSTPIP under the control of the cytomegalovirus promoter. Cells were stained with anti-FLAG (Cy3) and phalloidin-FITC. PSTPIP co-localizes with actin at the cortical region (c.a.), the stress fibers (s.f.) and the lamellipodia (lam.). Panels b and c illustrate two cells with abnormal morphology expressing PSTPIP. Note that these filopodial structures are greater than 100 microns in length. Panel c also illustrates that these cells have a different morphology from normally elongated 3T3 cells.
Figure 8B:
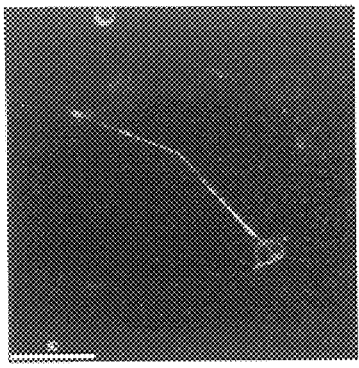
Figure 8C:
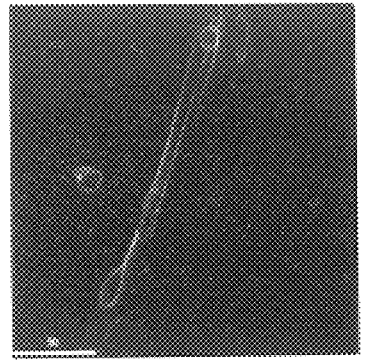

One role that PSTPIP might play in the cleavage furrow is the reorganization of polymerized actin (Cao et al., J. Cell Biol. 111:1905–1911 (1990a), Cao et al., J. Cell Biol. 110:1089–1095 (1990b), Fishkind et al., J. Cell Biol. 123 (4):837–848 (1993) and Fishkind, (1995) supra). In order to examine the possible function of PSTPIP in actin assembly, 3T3 cells were transfected with an epitope tagged version of the protein under the control of the powerful cytomegalovirus promoter, and the transfected cells were subsequently examined for expression of transfected PSTPIP as well as F actin. As can be seen in FIG. 8, 3T3 cells with normal morphology which expressed transfected PSTPIP showed co-localization of the protein at the cortical surface with F actin as well as in lamellipodial structures and the F actin stress fibers, in agreement with data obtained examining endogenous PSTPIP localization (see FIG. 7). FIG. 8 also illustrates that the overexpression of the protein often induced a remarkable morphological change in a high percentage of cells expressing it. These cells contained extended, filopodial-like structures that were filled with polymerized actin. In many cases, the structures were up to ~150 microns in length, and they often showed a knob-like morphology. In addition, the majority of cells contained a single extended filapodial structure. It appears that this structure was probably produced in the absence of significant cell growth or plasma membrane synthesis, since the overall size of the cell body appeared to decrease dramatically concomitant with the lengthening of the filapodial structure. This type of cell morphology is never observed with transfection of the green fluorescent protein (data not shown), and FIG. 8 illustrates that it is very different from the morphology of normally elongated, non-transfected cells. In summary, these results suggest that the unregulated expression of PSTPIP in vivo results in the induction of extended filopodial-like structures, consistent with the possibility that the protein may induce an inappropriate polymerization of the cortical cytoskeleton.

Example 6

N-terminal Deletions in PSTPIP

Materials and Methods

Deletional mutagenesis

Deletions in the PST PIP molecule were made from both the amino terminus and carboxy-terminus. The deletions were constructed from pfu-PCR fragments which were ligated back into the original PST PIP expression vector (Spencer et al, (1997), supra). The PCR primers for the N-terminal deletions were (all 5' to 3'):

| | | |
|---|---|---|
| N-coil.1; | CAGTTCGGATCCATGATGCTGCAGAGGCTGCTGGACGGCAGG-Leu26 | (SEQ ID NO: 30) |
| N-coil.2; | CAGTTCGGATCCATGATGGAGAGGTACGGGAAGGAGCTGGTG-Glu51 | (SEQ ID NO: 31) |
| N-coil.3; | CAGTTCGGATCCATGATGTCCTTTGACTCCCTGAAGCAGCAA-Ser76 | (SEQ ID NO: 32 |

-continued

N-coil.4; CAGTTCGGATCCATGATGGAGCTGCGGAGCCTGGAGGAGTTC-Glu101 (SEQ ID NO: 33)

N-coil.5; CAGTTCGGATCCATGATGGTCCAGAAGAGCAAGTTGTCGCTC-Ala151 (SEQ ID NO: 34)

N-coil.6; CAGTTCGGATCCATGATGGCAGATGATGCTGAGCAGGCCTTC-Ala201 (SEQ ID NO: 35)

Common 3-prime end primer; ACGTCACTCGAGTCACTTGTCATCGTCGTCCTT (SEQ ID NO: 36)

The primers for the C-terminal deletions were:

C-coil.1; TTGACCTCGAGTCATCACCGCTCAGGGGTGGGAGTCAGAGTC-Arg339 (SEQ ID NO: 37)

C-coil.2; TTGACCTCGAGTCATCACAGCCCAGAGAACCTCTTTATCA-Leu314 (SEQ ID NO: 38)

C-coil.3; TTGACCTCGAGTCATCAGTCATAGTAGTTCTGATAAGGCACCGGA-Asp289 (SEQ ID NO: 39)

C-coil.4; TTGACCTCGAGTCATCAGTCACCTTCCACATCACAGCCCTCAAGGGTC-Asp264 (SEQ ID NO: 40)

C-coil.5; TTGACCTCGAGTCATCAGGAGAGCTGGTTACAGTGCACCCACAGGGCA-Ser239 (SEQ ID NO: 41)

C-coil.6; TTGACCTCGAGTCATCACTCACGCAGGGCCAGGGCCAGCTGGATGTG-Glu100 (SEQ ID NO: 42)

The primer N-coil.1 was used as the common 5-prime PCR primer for the C-terminal deletions.

In vitro and in vivo analysis of PST PIP and PTP HSCF interactions

In vitro binding analyses between various PTP HSCF and PST PIP constructs were performed as previously described (Spencer et al, (1997), supra). Briefly, plasmids were transcribed and translated in vitro using the TnT Rabbit Reticulocyte Lysate System (Promega). Samples were diluted in 50 mM HEPES, pH 7.2, 1% triton X-100, 10% glycerol, 100 mM NaCl, and 2 µg/ml each of leupeptin, pepstatin, aprotinin and PMSF (lysis buffer). Samples were than reacted with GST fusion proteins at various concentrations, and the bound proteins were centrifuged using glutathione-sepharosebeads and analyzed on SDS polyacrylamide gels. C-terminally-derived peptide inhibition studies were performed by incubating the GST fusion protein binding reactions in the presence of 10 µg/ml of the indicated peptides. Peptides were produced by FMOC-protected amino acids as previously described (Spencer et al, (1997), supra). In vivo interactions between various forms of PTP HSCF and PST PIP were also performed as previously described (Spencer et al, (1997), supra). Briefly, COS cells were transfected with various constructs, and after 48 hours, lysates were prepared and immunoprecipitated with antibodies to either the FLAG epitope contained at the C-terminus of PST PIP or an HA epitope contained at the N-terminus of PTP HSCF. The resultant blots were probed with anti-FLAG to detect PST PIP, anti-HA to detect PTP HSCF or anti-phosphotyrosine to detect levels of this modified amino acid in each protein.

Confocal microscopy of transfected cells

Confocal microscopy was performed as previously described (Spencer et al, (1997), supra). Briefly, CHO cells in chamber slides were transfected using Lipofectamine and the indicated plasmids. 48 hours later, cells were fixed in formaldehyde and stained with an anti-FLAG epitope specific antibody (Kodak) and Fluorescein-Phalloidin (Molecular Probes). Anti-Flag stained cells were washed and stained with Cy3-conjugated sheep anti-mouse IgG. Stained cells were observed using a Molecular Dynamics Confocal Microscope (2001) and analyzed with ImageSpace software (Molecular Dynamics).

Results

PST PIP was originally isolated as a binding partner of the PEST-type PTP, PTP HSCF, in a yeast two-hybrid screen. Interestingly, all of the clones isolated in this procedure began within 10–15 amino acids of the N-terminus of PST PIP, consistent with the proposal that the N-terminus was critical for binding to PTP HSCF. In order to examine this possibility, deletions of 25 (delta 25), 50 (delta 50) and 75 (delta 75) amino acids of the N-terminus of the PST PIP coiled-coil domain were created. These deletion mutants were produced by in vitro transcription/translation, and they were tested for binding to a GST fusion protein containing the C-terminal 149 amino acids of PTP HSCF, including the proline-rich PST PIP binding site (GST-PTP HSCF). The full length and delta 25 forms of PST PIP were capable of interacting with the GST PTP HSCF fusion protein, while the delta 50 and delta 75 forms were not. This lack of binding might have been due either to a deletion of the actual binding site or to a misfolding of the protein. Transfection of either the full length or coiled-coil domain of PST PIP results in co-localization of the proteins with the cortical actin cytoskeleton and the lamellipodia, an event which presumably requires a correctly-folded protein. Thus, the analysis of the cellular localization of mutant forms of PST PIP can be utilized as an assay for correct folding of the protein. Both the wild type and delta 25 forms of PST PIP predominantly co-localized with the cortical actin cytoskeleton, while the delta 50 and delta 75 forms of the protein both formed large aggregates within the cytoplasm and showed no cortical localization, consistent with the hypothesis that these deletion mutants were improperly folded. These data are consistent with the results of the original two-hybrid assay, and they suggest that the N-terminus of PST PIP is required for the formation of a correctly folded protein that is capable of binding to PTP HSCF.

Discussion

The modulation of the tyrosine phosphorylation of a diversity of cellular proteins by protein tyrosine phosphatases is a critical aspect of cellular regulation (Neel and Tonks, Opin. Cell Biol., 9(2): 193–204 (1997). Many of these enzymatic dephosphorylations are mediated by the recognition of phosphotyrosine residues by SH2-type domains as well as direct recognition of the substrates by the catalytic domains of the enzymes (Garton et al., (1996), supra; Saxton et al., EMBO J 16(9):2352–2364 (1997)). Here we describe a novel mechanism for the regulation of tyrosine phosphorylationwhich involves the recognition of a proline rich motif at the C-terminus of the PTP by a tryptophan-containing site in the cytoskeletal-associated protein, PST PIP, which is divergent from the previously described SH3- and WW-type poly-proline binding modules. Because this protein-protein interaction appears to be required for the dephosphorylation of PST PIP phosphotyrosines (Spencer et al, (1997), supra), it may be a potentially important new mechanism for the regulation of the cytoskeleton.

The mechanisms utilized by both SH3 and WW domains in recognizing proline-rich helices have been elucidated through structure-function analyses using X ray crystallography, NMR and site directed mutagenesis. The SH3 domain consists of a highly structured 60 amino acid long module which appears to fold properly when expressed in the absence of other protein domains, and this short motif is capable of binding to proline-rich peptides with relatively high affinity (Terasawa et al., *Nat. Struc. Biol.*, 1:891–897 (1994); Wittekind et al., *J. Mol. Biol.* 267(4):933–952; Feng et al., *Proc. Natl. Acad. Sci. USA* 92:12408–12415 (1995)). The WW domain is also a relatively small (~38 amino acids), highly structured motif that is capable of forming an active protein when expressed in the absence of other modules (Macias et al., *Nature* 382:646–649(1996)). This is in contrast to the poly-proline recognition sequence found in PST PIP. In this case, deletion of the N-terminal 50 amino acids of the protein resulted in an apparently misfolded molecule that did not bind to the C-terminal proline-rich domain of PTP HSCF. These data are consistent with the possibility that this type of poly-proline recognition domain may require a greater complexity of interactions than either the SH3 or WW modules.

Example 7-Mutational analysis of PSTPIP

Materials and Methods

Mutagenesis

The mutagenesis of PST PIP was accomplished using the Dut/Ung procedure (BioRad Laboratories, Richmond, Calif.). The mutagenesis primers were designed to change 3 contiguous amino acids to alanine. Mutations were spaced approximately 12 amino acids apart, with new restriction sites engineered in for identification of mutant clones. Primer annealing was carried out at 70° C. for 10 minutes, 37° C. for 10 minutes, room temperature for 5 minutes, and then on ice prior to T7 DNA polymerase addition. The primers used for PST PIP alanine-scan mutagenesis were (all 5' to 3'):

```
D38VE:  GTCTGAGGAGCTCCGCCGCAGCCTTGCAC              (SEQ ID NO:43)

E50ER:  CCTTCCCGTACGCCGCCGCCGCCTGAGCTCTCTG          (SEQ ID NO:44)

R62K:   GGCCACCAGCCGCGGCTGCAATCTGCACGAGC            (SEQ ID NO:45)

R73TS:  CAGGGAGTCAAAGGCGGCCGCCAGGGAGTTCATC          (SEQ ID NO:46)

N84VG:  CTGGATGTGCGCGCTGGCCGCAGCCTCTGTTTGC          (SEQ ID NO:47)

R99EE:  CCTCCAAGCTTCGCAGCGCCGCAGCCAGGGCCAGGGC       (SEQ ID NO:48)

E110RQ: CCGCTGCTCTTTCGCTGCCGCTCGGAATTCCTCC          (SEQ ID NO:49)

I122MD: CTTCTGGACACGGGCCGCGGCGGCCTCATACTTCT         (SEQ ID NO:50)

L132YK: GGTCTTCTTGGCGGCCGCAAGCTTGCTCTTCT            (SEQ ID NO:51)

D145QK: GCATCCCTGCACGCCGCGGCATATAAGCTTTCTTGGACTCCA  (SEQ ID NO:52)

E159RV: GTGGCCATTGGCACTCGCAGCCGCGAAAGCTTGCTCAGCATC  (SEQ ID NO:53)

Q169VE: GGCTTTGTTCTGGCTCTTTGCTGCTGCCTTCTGGTGACCATTGGC (SEQ ID NO:54)

R194QN: CCTCGCTCTCTCCAGTTGTTCAATAGCTGCCGCGTACACTCT  (SEQ ID NO:55)

W204:   CTCCTGCTCCGCCTCGGTCCGAGCTCTCTCC             (SEQ ID NO:56)

F221:   GGATGGTGAGCCGGTCTGCCTCCTGCAGCTGGAGGCC       (SEQ ID NO:57)

L224:   CGGAGGATGGTGGCCCGGTCGAATTCCTGCAACTGG        (SEQ ID NO:58)

W232:   ATGGAGAGCTGGTTACAGTGCACCGCCAATGCATTGCGGAGG  (SEQ ID NO:59)

Cysteines within the region of PTP HSCF binding domain of
PST PIP were also mutated to alanine using the following
primers (all 5' to 3'):

Cys36:  TCCACATCCTTGGACATCTTCCTG                    (SEQ ID NO:60)

Cys148: CATCATCTGCATCCCTGGCCTTCTGGTCATATCCCTTCTTG   (SEQ ID NO:61)

Cys180: GGCTGACTCCTTGGACTGGTTGGC                    (SEQ ID NO:62)

Cys213: GAAGGCCTCGGAGGTAGTCCGGTGCTG                 (SEQ ID NO:63)
```

```
                                      -continued
Cys235:  ATGGAGAGCTGGTTGGAGTGCACCCACA                    (SEQ ID NO:64)

Cys242:  CATCATCCTTGACGGACTGCATGGAGAGCT                  (SEQ ID NO:65)

Cys259:  GATGTCACCTTCCACATCGGAGCCCTCAAGGGTCAG            (SEQ ID NO:66)
```

In vitro and in vivo analysis of PSTPIP and PTP HSCF interactions and confocal microscopy of transfected cells were performed as described in Example 6.

Analysis of v-Src mediated PST PIP tyrosine phosphorylation

COS cells were transfected with a constant amount of either the wild type or W232A mutant of PST PIP and cotransfected with increasing amounts of a plasmid encoding the v-Src tyrosine kinase (Spencer et al, (1997), supra). Plasmid concentrations were equalized with an empty vector containing the CMV promoter. After 48 hours, lysates were prepare and immunoprecipitated with anti-FLAG monoclonal antibody. Precipitates were run on SDS polyacrylamide gels, blotted, and probed with either anti-FLAG antibody or anti-phosphotyrosine antibody as previously described (Spencer et al, (1997), supra). Bound antibodies were visualized using enhanced chemiluminescent reagents.

Results

In order to more accurately define the binding site within the PST PIP coiled-coil domain, a collection of cluster and point mutations was produced within this domain. Preliminary deletionmapping suggestedthat binding of PTP HSCF could be obtained with a form of PST PIP containing amino acids 1–264 of the coiled coil domain, and the mutagenesis was thus confined to this region of the protein. Because protein folding appeared to be critical for the binding of PTP HSCF, all 6 cysteine residues within this part of the protein were mutated to serines, and the resultant mutants were tested for interaction with the PTP HSCF GST fusion protein. The elimination of individual cysteine residues did not appear to affect the binding of these two proteins, suggesting that the protein could fold and function appropriately in the absence of individual cysteines (data not shown). Further mutational analysis of PST PIP was thus performed to identify a region(s) that was potentially directly involved with PTP HSCF binding. Clustered alanine substitutions were produced at approximately 12 amino acid intervals throughout the PST PIP coiled-coil domain, and each mutant was subsequently tested for binding to the PTP HSCF GST fusion protein. Mutation of residue clusters L26QR, D38VE, E50ER, R62K, R73TS, N86VG, R99EE, E100RQ, I122MD, L133YK, D145QK, E159RV, Q169VE, E184S and R194QN individually to alanine resulted in either no or a minor change in the binding activity of these two proteins in vitro (data not shown). In the foregoing designations,the subscriptednumberfollowingthe firstone letteramino acid code identifies the amino acid position in SEQ ID NO: 1 where the alanine substitution begins, while the subsequent one letter amino acid codes identify the other, congruent amino acids which were replaced by alanine in each individual cluster. The mutation of the tryptophan residue at position 232 of PST PIP to alanine resulted in a complete loss of binding to the PTP HSCF GST fusion protein in vitro. Additionally, co-transfection of wild type PST PIP together with PTP HSCF into COS cells resulted in in vivo associationofthe proteins, as previously described (Spencer et al, (1997), supra), while cotransfection of the W232A mutant of PST PIP resulted in a complete lack of in vivo association, consistent with the in vitro binding studies. As expected, this mutant non-binding form of PST PIP could no longer be "substrate trapped" (Jia et al., (1995), supra; Garton et al., (1996),supra; Flint et al., (1997), sor; Spencer et al, (1997), supra) by a dominant negative Cys-Ser mutant of PTP HSCF (FIG. 12), although it could clearly be tyrosine phosphorylated in the presence of v-Src (FIG. 4) or pervanadate (data not shown). Thus, while the wild type PST PIP showed enhanced tyrosine phosphorylation in the presence of a dominant negative substrate trapping form of PTP HSCF (PTP HSCF C-S) (Jia et al, (1995), supra; Garton et al., (1996), supra; Flint et al., (1997), supra; (Spencer et al, (1997), supra), the W232A mutant of PST PIP was not hyperphosphorylated in the presence of this mutant form of the enzyme. Because previous results suggested that tryptophan, aromatic and hydrophobic residues are involved with the recognition of proline-rich domains when found appropriately spaced together in the context of other residues in WW-type domains (Macias et al., (1996), supra; Chen et al., (1 997), supra), we examined the PST PIP sequence for these residues near W232. This examination revealed that W232 is 27 amino acids C-terminal to another tryptophan at position 205. In addition, a phenylalanine (F221) and leucine (L224) residue also occur near the W232 residue with a spacing that is reminiscent of the WW motif (Andre et al., Biochem. Biophys. Res. Comm. 205(2):1201–1205 (1994). However, when these residues were mutated to alanine, no effect on PTP HSCF binding was observed in vitro. Thus, while the juxtaposition of these two tryptophan residues, together with the involvement of W232 in the recognition of the PTP HSCF proline-rich motif, is reminiscent of the WW module, comparison of the region containing these nearby tryptophans to the consensus sequence described for WW- type domains (Andre et al., (1994), supra) reveals that most of the conserved residues within the WW module are not found in this region of PST PIP (data not shown). In addition, the spacing of the two tryptophan residues in PST PIP is somewhat longer than that found for typical WW-type motifs (27 amino acids for PST PIP versus ~22 amino acids for consensus WW domains). Finally, in order to insure that mutation of the critical tryptophan did not result in a global effect on protein folding, as was observed for the delta 50 and 75 deletion mutants, the W232A mutant was transfected into CHO cells and analyzed by confocal microscopy. This mutant protein appears to co-localize with the cortical actin cytoskeleton in a manner that is indistinguishable from the wild type protein, consistent with the supposition that the W232A mutant was appropriately folded in vivo. These data thus suggest that tryptophan residue 232 may be directly involved with the interactionbetween PST PIP and PTP HSCF. In addition, because W232 does not appear to be embedded in a typical WW module (Andre et al., (1994), supra), they also suggest that this region defines a novel type of protein-protein recognition motif.

Previously, we demonstrated that PST PIP was tyrosine phosphorylated when co- transfected with v-Src tyrosine kinase (Spencer et al, (1997), supra). In addition, we showed that this tyrosine phosphorylated PST PIP was a substrate for dephosphorylation or "substrate trapping" by wild type or dominant negative PTP HSCF, respectively, and that the substrate trapping activity required an interaction between the two proteins mediated by the C-terminal proline rich region of the PTP (Spencer et al, (1997), supra). We also established that an endogenous tyrosine kinase(s) was capable of phosphorylating tyrosines within PST PIP in both BaF3 and transfected COS cells, and an endogenous tyrosine phosphatase(s) was capable of dephosphorylating these tyrosine residues. In addition, preliminary evidence suggested that the W232A mutant was more efficiently phosphorylatedthan the wild type PST PIP in the presence of v-Src. In order to more quantitatively examine the role of the W232 residue in v-Src-induced tyrosine phosphorylation, we transfected constant amounts of the wild type and W232A mutant forms of PST PIP into COS cells together with increasing quantities of the v-Src expression plasmid and subsequently analyzed the levels of phosphotyrosine in imnmunoprecipitated PST PIP. The W232A mutant form of PST PIP, which was deficient in binding to PTP HSCF, was significantly more efficiently tyrosine phosphorylated in the presence of v-Src in vivo than the PTP-binding wild type protein. These data are consistent with the hypothesis that PST PIP likely interacts with, and is dephosphorylated by, an endogenous PEST-type PTP in COS cells, and the loss of this interaction, as observed with the W232A mutant, results in enhanced tyrosine phosphorylation of the protein in the presence of v-Src.

Discussion

The importance of overall structure to ligand recognition by the WW domain is emphasized by mutation of the proline which is C-terminal to the critical tryptophan recognition residue (Chen et al. (1997), supra). Mutation of this residue, which is conserved in all WW motifs, to alanine results in an inactive WW module, presumably due to a disruption in the fold of the domain. The PST PIP poly-proline recognition sequence is missing this highly conserved proline (Spencer et al, (1997), supra), consistent with the possibility that other residues in the protein may be involved with the formation of the ligand binding site. Of potential importance is the finding that the region containing the poly-proline recognition sequence in PST PIP is in a domain that is predicted to form a coiled coil [31], and preliminary data suggest that this area of PST PIP mediates dimerization, a characteristic of coiled coil-containing proteins. This, together with the results of the N-terminal deletion studies discussed in Example 6, suggests that the overall fold of this relatively extended domain might be critical for the formation of a correctly structured poly-proline recognition site.

While these results suggest that the PST PIP poly-proline recognition domain is functionally and structurally divergent from the SH3 and WW modules, an interesting connection between these binding motifs is the inclusion of a critical tryptophan residue in all three domains. In both SH3 and WW motifs, these tryptophans are conserved in all of the modules that have thus far been identified. In the case of both the SH3 (Feng et al., Science 266:1241–1247(1994)) and WW (Chenetal. (1997),supra) motifs, the tryptophan appears to be critical for the interaction with the proline rich peptide, as mutation of this residue results in diminished binding. Interestingly, this is also the case for the PST PIP proline-rich recognition site, consistent with the possibility that tryptophan residues are uniquely suited for the recognition of poly-proline rich domains. Structural data from both SH3 and WW domains confirms this hypothesis. In the case of the SH3 domain, the conserved tryptophan residue is found in the binding pocket, and this residue appears to interact by stacking with helically oriented prolines in the proline rich ligand (Feng et al., (1994), supra;Terasawa et al., (1994), supra; Wittekind et al., (1997), supra)). NMR analysis of the WW domain from the yes kinase associated protein (YAP) (Sudol et al., *J Biol. Chem.* 270(24) :14733–14741 (1995)) likewise reveals an interaction between the conserved tryptophan residue and prolines in the proline helix recognized by this protein, although it is also possible that this conserved tryptophan is involved with the structure of the binding pocket (Macias, et al., (1996), supra; Chen et al. (1997), supra). The fact that mutation of a single tryptophan in the coiled coil region of PST PIP abolishes both in vitro and in vivo binding to the phosphatase is consistent with the hypothesis that this tryptophan residue may similarly interact with potentially helically oriented prolines in the C-terminus of the PEST PTPs. Alternatively, it is possible that conversion of this hydrophobic residue to an alanine results in a misfolding of the protein. However, if the W232A mutant protein is improperly folded, it is likely that this is only a localized disruption, since it is still capable of associating with the cytoskeleton and is tyrosine phosphorylated in the presence of transfected v-Src or the PTP inhibitor, pervanadate. Interestingly, the tryptophan located N-terminal to the critical tryptophan involved with binding of PST PIP to PTP HSCF does not seem to be required for ligand recognition, a result which is similar to that found for the N-terminal tryptophan of the WW domain in YAP (Chen et al. (1997), supra). Finally, while it appears that a number of other residues, particularly with hydrophobic and aromatic side chains, are involved with the recognition of the proline-rich ligand by both SH3 and WW (Macias, et al., (1996), supra; Chen et al. (1997), supra) domains, mutation of two such residues in PST PIP (F221 and L224) does not have a significant effect on binding, consistent with the supposition that the poly-proline recognition domain of PST PIP is divergent from the WW module.

The potential importance of W232 in the function of PST PIP is underlined by the finding that expression of the W232A mutant in COS cells together with the v-Src tyrosine kinase results in an enhanced tyrosine phosphorylationof the cytoskeletal associated protein. These data are consistent with the hypothesis that PST PIP interacts with endogenous PTPs in vivo, and this interaction mediates the removal of phosphates from tyrosine residues. Furthermore, because this mutation blocks the binding of the PEST-type PTP HSCF via the C-terminal proline rich domain, these results suggest that it is probable that PST PIP interacts with one or more endogenous PEST-type tyrosine phosphatases in COS cells. However, the question remains as to why the W232A mutant is not constituitivelytyrosine phosphorylated in the absence of v-Src, since it is likely that the protein is unable to efficiently bind endogenous PEST-type PTPs. While it might be argued that the appropriate tyrosine kinase is not present in COS cells, we have previously demonstrated that the protein is tyrosine phosphorylated in the presence of vanadate, both in in its endogenous state in BaF3 cells as well as when it is transfected into COS cells (Spencer et al, (1997), supra). A likely explanation for these data is that the kinase that phosphorylates PST PIP requires an activation event, such as tyrosine phosphorylation,to mediate this modification. Thus, v-Src, which is a constituitively activated tyrosine kinase, would be predicted to mediate the tyrosine phosphorylation of the W232A mutant in the absence of vanadate. In addition, the data suggests that vanadate must activate an endogenous tyrosine kinase(s), presumably by inhibiting an endogenous tyrosine phosphatase (Jia et al, (1995), supra)), which subsequently mediates the tyrosine phosphorylation of PST PIP.

Example 8-Mutational analysis of PTP HSCF

Materials and Methods

Mutagenesis

Single codon mutations to alanine were made in the carboxy-terminus of PTP HSCF following the procedure described in Example 7, and using the following primers (all 5' to 3'):

| | | |
|---|---|---|
| HSCF R436: | CCCTTTGGGTCGACCGATGGCCAAGTTGAAGCC | (SEQ ID NO:67) |
| HSCF P440: | AGGATCTCGGGGCCCTTTGGCCCTTCCGATGCGC | (SEQ ID NO:68) |
| HSCF G442: | CTGGAGGATCTCGAGGTGCTTTGGGCCTTCC | (SEQ ID NO:69) |
| HSCF P443: | GGAGGATCTCGGGCCCTTTGGGCCTTCCG | (SEQ ID NO:70) |
| HSCF R444: | CTGCAGGAGGATCCGCGGGCCCTTTGGGCCTTCC | (SEQ ID NO:71) |
| HSCF P447: | GTCCACTCTGCAGCAGGATCCCGGGGCCCTT | (SEQ ID NO:72) |
| HSCF W450: | GTTACACCCGTGTCGCCTCTGCAGGAGGATCCCG | (SEQ ID NO:73) |

The R444+W450 double mutant was made with the HSCF W450 primer on a single-strand template of the R444 mutant phosphatase. The mutants were all confirmed by DNA sequencing.

The other techniques were performed as described in the previous examples.

Results

In order to analyze the residues within the C-termiinal 20 amino acid region of PTP HSCF that were critical for PST PIP binding, 20 amino acid peptides with alanines incorporated separately at each position were tested for blocking of the interaction in vitro. Previously we demonstrated that a 20 amino acid peptide derived from this region of three different PEST-type PTPs (Yang et al., J Biol. Chem. 268(23) :17650 (1993); Matthews et al, (1992), supra; Cheng et al., (1996), sura)) was capable of efficiently blocking the binding of an in vitro translated form of PST PIP to a GST fusion of PTP HSCF containing the C-terminal 149 amino acids, including the C-terminal proline-richbinding site (GST PTP HSCF) (Spencer et al, (1997), supra). Alanine replacement of R436, P440, G442, P443, R444, P447, and W450 individually in a peptide derived from the C- terminus of PTP HSCF resulted in a decreased inhibition of binding by the mutant peptides, while alanine replacement at the other sites within the peptide had little or no effect on the ability of these peptides to block the interaction in vitro. Importantly, these residues are conserved in all of the PEST-type PTP C-termini (Yang et al., (1993), sura; Matthews et al., (1992). supra; Cheng et al., (1996),supra); Kim et al., Oncogene 13:2275–2279(1996)), consistent with previous data (Spencer et al, (1997), supra) demonstrating that peptides derived from the other members of this family of phosphatases all effectively blocked this interaction). To confirm the peptide mutation analysis, each residue found to be critical for PST PIP binding in the PTP HSCF C-terminal region was mutated to alanine in the context of the whole protein, and the ability of each mutant PTP to bind PST PIP was analyzed in vitro and in vivo. FIG. 14 illustrates that mutants of the phosphatase containing alanines at all but one of the positions predicted from the peptide mapping study (P443, ) were substantially deficient in binding to GST PST PIP in the in vitro binding assay, although 10 fold increased amounts of GST PST PIP could interact with the mutant PTP HSCF proteins, suggesting only a partial loss of binding. In addition production of a double mutation in two of the critical residues in this region of PTP HSCF (R444 and W450) resulted in a stronger inhibitory effect on binding to PST PIP. In vivo analysis ofthese point mutants revealed only a modest effect on binding in the single mutants of PTP HSCF, consistent with the in vitro data suggesting that sufficiently high levels of PST PIP could interact with the mutant proteins. However, as was observed in the in vitro experiments, the doubly mutated form of PTP HSCF (R444+W450) was as poor at interacting in vivo with PST PIP as the mutant which was missing the entire C-terminal proline rich domain (PTP HSCF D24) (Spencer et al, (1997), supra). These data confirm the importance of these residues to the binding interaction, and they suggest that much of the C-terminal region of PTP HSCF may be required for highest affinity binding to PST PIP.

Discussion

Mutational analysis of the proline rich domain of PTP HSCF is compatible with the proposal that the PST PIP binding site is a novel poly-proline recognition module. These data demonstrated that the binding site in the phosphatase appeared to stretch over a length of approximately 15 amino acids, from R436 to W450. This is in contrast to structural studies on SH3 and WW domain recognition sites, where mutagenesis, X ray crystallography and NMR analyses have demonstrated that stretches of 10–12 (Feng et al, (1994), supra;Terasawa et al., (1994),supra; Wittekind et al., (1997), supra)) or 6 (Macias, et al., (1996), supra; Chen et al. (1997), supra) residues, respectively, are required for the highest affinity interaction. In addition, while the PST PIP poly-proline recognition domain appears most like the WW module in that it contains two relatively closely spaced tryptophans, the ligands recognized by the WW motif have been found to have the general structure, XPPXY, with both prolines and the tyrosine performing critical recognition functions (Chen et al., (1995), supra; Einbond et al., FEBS Letts. 384:1–8 (1996); (Macias, et al., (1996), supra; Pirozzi et al., J Biol. Chem. 272(23)14611–14616 (1997). The PTP HSCF poly-proline region contains two adjacent proline residues, one of which was found to be involved with binding, but there is not a tyrosine residue C-terminal to the second proline. While these results suggest that the recognition of the PTP HSCF poly-proline domain by PST PIP is quite different from the mechanisms utilized by SH3 and WW modules, a striking similarity is found in the involvement of closely spaced proline residues. Similar requirements have been found for the prolines in SH3 recognition sites (Feng et al., (1994), supra) while mutation of these residues in WW recognition sites, while not quantitatively measured, also showed an effect on binding (Chen et al. (1997), supra). Again, structural analysis of SH3 and WW modules bound to their cognate ligands illuminates the role of these prolines in binding. In the case of both of these motifs, the ligand adopts a type II poly-proline helical conformation which allows for interactions between residues within the helical region and conserved side chains within the recognition modules (Feng et al., (1994), supra; Feng et al., Proc. Natl. Acad. Sci. USA 92:12408–12415 (1995)). Because mutation of the prolines in the PST PIP C-terminal region resulted in an effect on binding, it is likely that this region may also form a type II proline helix which disposes the relevant side chains in the appropriate conformation. In addition, and in contrast to the SH3 and WW recognition motifs, the glycine contained within this region also appears to be involved with binding to PST PIP. Because glycine residues are also mediators of peptide structure, it is possible that this residue may serve to fold this small region into an appropriate conformation, and it may be this high concentration of structure inducing residues that allows this diminutive peptide to bind to PST PIP so efficiently (Spencer et al, (1997), supra). Significantly, mutagenesisstudieshave also revealed the importance of non-proline residues in the binding of both SH3 and WW motifs to poly-proline ligands. In the case of the WW domain, the conserved tyrosine residue of the ligand is important for the interaction and makes a direct contact with the binding module (Macias, et al., (1996), supra), while amino acids in the N- or C-terminal regions of the SH3 recognition site can determine the orientation and affinity of binding of the peptide ligands (Feng et al., (1995), supra)). Because mutation of the arginines contained within the PTP HSF C-terminus had an effect on binding, it is possible that electrostatic interactions are involved with the binding event, as has been observed for SH3 recognition modules (Feng et al., (1995), supra)). The importance of the C-terminal tryptophan suggests the possibility of hydrophobic stacking interactions, perhaps with the important tryptophan residue in PST PIP. Finally, because the residues involved with binding are highly conserved (Cheng et al., (1996), supra)), these data are completely consistent with previous studies demonstrating that C-terminal proline- rich peptides derived from the C-termini of the related PTPs PEST, PEP (Spencer et al, (1997), supra) and BDP-1 effectively block the interaction between PTP HSCF and PST PIP.

M. Summary

We have isolated a novel member of the actin binding protein family, PSTPIP, which binds to the PEST tyrosine phosphatases via an interaction between the proline rich C-terminal homology domain of the PTP and the coiled coil domain of the interacting protein. Like many other proteins associated with the cytoskeleton, PSTPIP is tyrosine phosphorylated in V-src transfected cells, and at least a subset of these phosphorylated residues appear to be substrates for the catalytic site of the bound PTP HSCF. PSTPIP is localized to the cortical cytoskeleton, as well as in lamellipodia and on stress fibers, and it appears to migrate to the actin-rich cleavage furrow during cytokinesis. Overexpression of the protein in 3T3 cells induces long filopodial structures, consistent with a role for PSTPIP in the reorganization of the cytoskeleton. These data demonstrate that PSTPIP is a cytoskeletal binding protein whose physiological function is, in part, regulated by its degree of tyrosine phosphorylation.

Analysis of the protein database for sequences with homology to PSTPIP suggests potential functions for this novel protein. Most of the sequences with significant homology to PSTPIP fall into the actin binding family of proteins, and it is clear from the confocal studies reported here that PSTPIP interacts with actin. While a number of other actin binding type proteins, including myosin, fodrin and spectrin, show homology to PSTP IP, the bulk of these homologies are within the SH3 domain, with little or no match in other regions of the protein. This is also true for another protein which binds to the actin cytoskeleton in a similar, but not identical, manner, p80/85 cortactin (Wu et al., (1991) supra), although there is weak homology in a small region of the coiled coil domain as well as the SH3 region. This is in contrast to the protein with the greatest degree of homology, the yeast S. pombe cdcl5p, which shows significantsequence conservationin both the SH3 as well as the coiled coil domains (Fankhauseret al., (1995) supra). Cdc 15p is a highly phosphorylated protein which is absolutely required for the formation of the actin ring at the cleavage flurow of the post-mitotic cell, and mutations in this protein result in an inability to assemble the actin ring over the postmitoticnucleus, thus resulting in multi-nucleatecells. As with PSTPIP, cdcl5p is localized to the cortical actin cytoskeleton until anaphase, when it migrates over the postmitotic nucleus and presumably mediates the reorganization of the cytoskeleton to the cleavage plane (Fankhauser et al., (1995) supra Chang et al., Cell 84:191–194 (1996) and Simanis, Sem. in Cell Biol 6:79–87 (1995)). While the timing of PSTPIP migration to the cleavage firrow remains to be determnined, its striking co-localization with the actin ring at this site during cytokinesis is analogous to what is observed with cdcl 5p (Fankhauser et al., (1995) supra). In addition, the cdcl5p is hyperphosphorylated until the onset of anaphase and the formation of the F actin cytokinetic cleavage ring, when it becomes significantly dephosphorylated. Interestingly, the yeast protein regains its high state of phosphorylation at the conclusion of cell division, suggesting that phosphorylation regulates its association with the cleavage furrow. While the type of phosphorylation of cdcl5p has not yet been analyzed, this suggests that tyrosine and/or serine threonine phosphatases must be involved with the regulation of the function of cdc 15p, and provides a mechanism whereby the binding and catalytic activity of a PTP such as PTP HSCF might function to control cytokinesis. Again, while the timing of tyrosine phosphorylation of PSTPIP during the cell cycle has yet to be determined, both the exact conservation of 5 tyrosine residues between PST-PIP and cdcl5p as well as the vanadate sensitive tyrosine phosphorylation of endogenous PTP interacting protein in Baf3 cells are suggestive of modulation of phosphotyrosine levels during the cell cycle. Thus, the sequence, cellular localization, and phosphorylation of both PSTPIP and cdc15 suggest that the mammalian protein is a potential homologue of cdcl5p.

Phosphorylation, especially of serine and threonine residues, has been previously shown to play important roles in regulating events in cytokinesis and reorganization of the cytoskeletal (Yamakita et al., J. Cell Biol. 124:129–137 (1994), Egelhoff et al., Cell 75:363–371 (1993) and Fishkind et al., (1995) supra). To date, however, the possibilitythat tyrosine phosphorylation may play a role in these finctions has been incompletely examined. The data reported in this paper demonstrate that the regulation of tyrosine phosphorylation on PSTPIP by PTP HSCF may play a role in aspects of cytoskeletal control including, possibly, cytokinesis. While the possible kinases involved in such phosphorylation are numerous, the information described here as well as elsewhere suggests that a member of the Src family of tyrosine kinases may be involved with the phosphorylation of this interacting protein by either direct or indirect mechanisms. Two other PSTPIP-related proteins, p80/85 cortactin and the HS1 protein, are both known to be tyrosine phosphorylated in V-src transformed cells, and cortactin is known to interact with the cytoskeleton in a manner similar to PSTPIP (Wu et al., (1991) supra). In addition, a plethora of other proteins which are involved with the cytoskeleton are also tyrosine phosphorylated in V-src transformed cells (Schaller et al., *Prog. Nuc. Acid Res. and Mol. Biol.* 44:205–227 (1993)). Interestingly, the tyrosine phosphorylation of cortactin is also dramatically enhanced in cells isolated from mice deficient in the Csk kinase (Thomas et al., (1995) supra), a tyrosine kinase which phosphorylates the C-terminal inhibitory tyrosine on C-src, suggesting that cortactin is either a direct or indirect C-src substrate in vivo. In addition, it has been demonstrated that HS1 can bind to the SH3 and SH2 domains of Src in vitro, and it is also tyrosine phosphorylated by this kinase in vitro and in vivo (Takemoto et al., (1996) sra). Although only distantly related to cortactin and HS1, the tyrosine phosphorylation of PSTPIP by V-src in transfected cells may therefore be of physiological relevance.

In addition, previous data have demonstrated that C-src associates with the focal adhesions and lamellipodia, as well as other actin-containing sites, consistent with the possibility that it could phosphorylate PSTPIP, which also localizes to these regions (Kaplan et al., (1994) supra). Finally, V-src is known to induce cytoskeletal changes in transformed cells, and it has been clearly shown that cortactin, an actin binding protein, becomes reoriented from the ends of the stress fibers to the podosomes of these Src-transformed cells, consistent with the possibility that phosphorylation of such actin binding proteins might mediate changes in their cellular localization (Wu et al., (1991) supra).

The use of dominant negative forms of PTPs has been previously utilized to identify substrates for several enzymes, most notably PTP PEST (Garton et al. (1996) supra) and the corkscrew PTP (SH PTP-2) (Herbst et al., (1996) supra). In general, these studies have demonstrated that these dominant negative mutants enhance the tyrosine phosphorylation of a surprisingly limited number of substrates in vivo, in contrast to the relatively promiscuous behavior of these enzymes in vitro. The demonstration here that co-expression of two different dominant negative forms of PTP HSCF mediates a dramatic increase in V-src induced PSTPIP tyrosine phosphorylation is thus consistent with several conclusions. The first is that these two proteins interact intimately in vivo, probably through the C-terminal homology domain and the coiled coil region interaction determined from the in vitro binding studies, and the co-precipitation analysis (FIG. 6) supports such a physical interaction. This then provides yet another example of the use of a non-catalytic region by a PTP to bring the catalytic domain in close proximity to the substrate, although the binding mechanism utilized in this case is novel (Tonks, (1993) supra). The second is that it is likely that tyrosine phosphorylate d PSTPIP is an in vivo substrate for the PTP HSCF and it suggests that the enzyme inhibited by vanadate in the endogenous phosphotyrosine experiment in Baf3 cells, where both PSTPIP and PTP HSCF are expressed, is likely to be PTP HSCF. Finally, if we assume that the mutant forms of PTP HSCF are endowed with the same degree of substrate specificity that has been found with other dominant negative PTPs, than the V-src co- transfection studies further suggest that either Src or a related family member may be a kinase which is involved with the tyrosine phosphorylation of PSTPIP in vivo in non- transfected cells.

The nature of the high affinity binding between the proline rich C-terminal homology domain and the coiled coil region is reminiscent of that previously described for the SH3-proline rich core interaction (Pawson, (1995) supra). In this latter case, proline helices induce the formation of highly structured small peptide domains that bind with relatively high affinity and specificity to the binding pocket of the SH3 domain, and various interactions, including salt bridges, mediate the specificity and direction of peptide binding (Feng et al., (1995) supra). Analysis of the proline rich C-terminal homology domains of three PEST PTPs, all of which appear to inhibit the PSTPIP-PTP HSCF binding interaction with similar $IC_{50s}$, reveals that they share a proline rich core region that would be predicted to form a proline helix similar to that seen for SH3 binding sites (Yang et al., (1993) supra, Matthews et al., (1992) supra and Cheng et al., (1996) supra). This region contains a number of charged residues, and it is possible that the potential helical nature of this domain positions these residues in an appropriate binding conformation for interaction with a site within the coiled coil domain. Because all of the PEST PTPs are predicted to bind to PSTPIP via this proline rich region, it is possible that the interacting protein's phosphotyrosine content is modulated by different PEST PTPs in different cell types. Along these lines, it is interesting to note that the only hyperphosphorylated protein observed in COS cells transfected with dominant negative (D-A) PTP PEST was $p130^{cas}$ (Garton et al., (1996) supra). This results suggest that, if PSTP IP is expressed in COS cells, it is either not tyrosine phosphorylated or is not a substrate for this PTP in this cell line. The mechanism by which PSTPIP migrates from the cortical actin, lamellipodia and stress fiber regions in resting cells to the cytokinetic cleavage furrow in dividing cells can only be speculated upon (Strome, *Cell* 72:3–6 (1993)). One possibility is that this protein binds tightly to actin, and when the actin is reoriented to the cleavage plane, the PSTPIP accompaniesit passively (Cao et al., (1990a) supra, (Cao et al., (1990b) supra and Fishkind, (1993) supra). However, experiments in yeast where cdc15p is deleted revealed that cortical actin did not migrate to the cleavage plane in the absence of this protein, suggesting that cdc15p actively traverses to this site and mediates the assembly of the actin ring (Simanis (1995) supra). These data thus suggest that if PSTPIP is a mammalian homologue of cdc15p, that dominant negative mutants in this protein should abolish the assembly of actin at the cleavage furrow. Interestingly, it appears that deletion mutants of cdc15p which lack the SH3 domain are incapable of rescuing the cdc15 mutants, suggesting a critical role for this C-terminal domain in assembling the cytokinetic actin ring (Fankhauser et al., (1995) supra).

A possible mechanism by which PSTPIP finctions is suggested by the results of overexpression studies in murine 3T3 cells. The extended filopodial structures in many of these transfected cells are consistent with the possibility that the unregulated expression of the protein mediates an ectopic and organized assembly of actin filaments, thus resulting in a cellular protrusion containing PSTPIP and F actin. In this regard, the striking level of lysines in the predicted coiled coil domain of this protein is consistent with previously described actin binding sites (Vandekerckhove, *Curr. Opin. Cell Biol.* 2:41–50 (1990) and Friederich et al., *Cell* 70:81–92 (1992)). Interestingly, many of the transfected cells contained a single filopodial-like structure, suggesting that this morphological feature is rapidly formed and is likely to have a negative influence on cell viability. The apparent small size of many of these cells suggests that this actin-containing spike is formed in the absence of plasma membrane synthesis, also consistent with a rapid formation of the structure. The apparent heterogeneity in penetrance of this morphological entity may be due either to expression levels or differences in post-translational modifications of the transfected proteins. Thus, it would appear that PSTPIP may play a role in the rapid assemble of a highly organized F actin containing structure.

Example 9

Expression of PSTPIP in E. coli

This example illustrates preparation of an unglycosylated form of PSTPIP by recombinant expression in E. coli.

The DNA sequence encoding PSTPIP (SEQ ID NO:2) is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PSTPIP coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centriflgation. The cell pellet obtained by the centrifagation can be solubilized using various agents known in the art, and the solubilized PSTPIP protein can then be purified using a metal chelating column under conditions that allow tight binding of the protein.

Example 10

Expression of PSTPIP in mammalian cells

This example illustrates preparation of a glycosylated form of PSTPIP by recombinant expression in mammalian cells.

The vector, pRK5 (see EP 307,247, published Mar. 15, 1989), is employed as the expression vector. Optionally, the PSTPIP DNA is ligated into pRK5 with selected restriction enzymes to allow insertion of the PSTPIP DNA using ligation methods such as described in Sambrook et al., supra. The resulting vector is called pRK5-PSTPIP.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 $\mu$g pRK5-PSTPIP DNA is mixed with about 1 $\mu$g DNA encoding the VA RNA gene [Thinumappaya et al., Cell, 31:543 (1982)] and dissolved in 500 $\mu$ of 1 mM Tris-HCl, 0.1 mM EDTA, 0.227 M $CaCl_2$. To this mixture is added, dropwise, 500 $\mu$l of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200, $\mu$Ci/ml $^{35}$S-cysteine and 200 $\mu$Ci/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PSTPIP polypeptide. The cultures containing transfected cells may undergo further incubation (in serum free medium) and the medium is tested in selected bioassays.

In an alternative technique, PSTPIP may be introduced into 293 cells trnsiently using the dextran sulfate method described by Somparyrac et al., Proc. Natl. Acad. Sci. 12:7575 (1981). 293 cells are grown to maximal density in a spinner flask and 700 $\mu$g pRK5-PSTPIP DNA is added. The cells are first concentrated from the spinner flask by centrifugation and washed with PBS. The DNA-dextranprecipitate is incubated on the cell pellet for four hours. The cells are treated with 20% glycerol for 90 seconds, washed with tissue culture medium, and re-introduced into the spinner flask containing tissue culture medium, 5 $\mu$g/ml bovine insulin and 0.1 $\mu$g/ml bovine transferrin. After about four days, the conditioned media is centrifuged and filtered to remove cells and debris. The sample containing expressed PSTPIP can then be concentratedand purified by any selected method, such as dialysis and/or column chromatography.

In another embodiment, PSTPIP can be expressed in CHO cells. The pRK5-PSTPIP can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PSTPIP polypeptide,the culture medium may be replaced with serum free medium. Preferably, the cultures are incubated for about 6 days, and then the conditioned medium is harvested. The medium containing the expressed PSTPIP can then be concentrated and purified by any selected method.

Epitope-tagged PSTPIP may also be expressed in host CHO cells. The PSTPIP may be subcloned out of the pRK5 vector. The subclone insert can undergo PCR to fuse in frame with a selected epitope tag such as a poly-his tag into a Baculovirus expression vector. The poly-his tagged PSTPIP insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PSTPIP can then be concentrated and purified by any selected method, such as by $Ni^{2+}$-chelate affinity chromatography.

Example 11

Expression of PSTPIP in Yeast

The following method describes recombinant expression of PSTPIP in yeast.

First, yeastexpressionvectors are constructed for intracellularproductionor secretion of PSTPIP from the ADH2/GAPDH promoter. DNA encoding PSTPIP, a selected signal peptide and the promoter is inserted into suitable restriction enzyme sites in the selected plasmid to direct intracellular expression of PSTPIP. For secretion, DNA encodingPSTPIP can be cloned into the selected plasmid, together with DNA encoding the ADH2/GAPDH promoter, the yeast alpha-factor secretory signalleader sequence, and linker sequences (if needed) for expression of PSTPIP.

Yeast cells, such as yeast strain AB 110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PSTPIP can subsequently be isolated and purified by removing the yeast cells from the fermentation medium by centrifugation and then concentrating the medium using selected cartridge filters. The concentrate containing PSTPIP may further be purified using selected column chromatography resins.

Example 12

Expression of PSTPIP in Baculovirus

The following method describes recombinant expression of PSTPIP in Baculovirus.

The PSTPIP is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the PSTPIP or the desired portion of the PSTPIP (such as the sequence encoding the extracellular domain of a taansmembrane protein) is amplified by PCR with primers complementary to the 5' and 3' regions. The 5' primer may incorporate flanking (selected) restriction enzyme sites. The product is then digested with those selected restriction enzymes and sub-eloned into the expression vector.

Recombinant baculovirus is generated by co-transfecting the above plasmid and BaculoGold virus DNA (Pharmingen) into *Spodoptera fugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged PSTPIP can then be purified, for example, by $Ni^{2+}$-chelate affinity chromatography as follows. Extracts are prepared from recombinant virus-infected Sf9 cells as described by Rupert et al., *Nature*, 3:175–179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imnidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged PSTPIP are pooled and dialyzed against loading buffer.

Alternatively, purification of the IgG tagged (or Fc tagged) PSTPIP can be performed using known chromatography techniques, including for instance, Protein A or protein G column chromatography.

N. Concluding Remarks:

The foregoingdescriptiondetails specific methodswhichcan be employedto practice the present invention. Having detailed such specific methods, those skilled in the art will well enough known how to devise alternative reliable methods at arriving at the same information in using the fruits of the present invention. Thus, however, detailed the foregoing may appear in text, it should not be construed as limiting the overall scope thereof; rather, the arnbit of the present invention is to be determined only by the lawfiul construction of the appended claims. All documents cited herein are expressly incorporated by reference.

What is claimed is:

1. An isolated nucleic acid molecule hybridizing under stringent conditions to the complement of the nucleic acid of SEQ ID NO: 2 and which encodes a polypeptide substantially retaining the ability to bind to a protein tyrosine phosphatase which (a) possesses a non-catalytic domain comprising a region rich in proline, serine and threonine residues and a C-terminal 20 amino acid segment which is rich in proline residues, and (b) defines at least one SH3 binding domain, wherein said stringent conditions are hybridization in a solution containing 50% formamide, 5×SSC (0.75 M NaCl, 0.075 M sodium citrate), 50 mM sodium phosphate (pH 6–8), 0.1% sodium pyrophosphate, 5×Denhardt's solution, 50 µg/ml sonicated salmon sperm DNA, 0.1% sodium dodecyl sulfate (SDS) and 10% dextran sulfate at 42° C., followed by wash at 42° C. in 0.2×SSC and 0.1% SDS.

2. A vector comprising the nucleic acid molecule of claim 1 operably linked to control sequences recognized by a host cell transformed with the vector.

3. A host cell comprising the vector of claim 2.

4. A host cell comprising the nucleic acid molecule of claim 1.

5. The isolated nucleic acid molecule of claim 1 comprising the sequence of SEQ ID NO: 2, SEQ ID NO: 28 or SEQ ID NO: 29.

6. A vector comprising the nucleic acid molecule or claim 5 operably linked to control sequences recognized by a host cell transformed with the vector.

7. A host cell transformed with the vector of claim 6.

8. A method for producing a PST phosphatase interacting protein comprising transforming a host cell with nucleic acid hybridizing under stringent conditions to the complement of the nucleic acid of SEQ ID NO: 2 and which encodes a polypeptide substantially retaining the ability to bind to a protein tyrosine phosphatase which (a) possesses a non-catalytic domain comprising a region rich in proline. serine and threonine residues and a C-terminal 20 amino acid segment which is rich in proline residues, and (b) defines at least one SH3 binding domain, wherein said stringent conditions are hybridization in a solution containing 50% formamide, 5×SSC (0.75 M NaCl, 0.075 M sodium citrate), 50 mM sodium phosphate (pH 6–8), 0.1% sodium pyrophosphate, 5×Denhardt's solution, 50µg/ml sonicated salmon sperm DNA, 0.1% sodium dodecyl sulfate (SDS) and 10% dextran sulfate at 42° C., followed by wash at 42° C. in 0.2×SSC and 0.1% SDS, culturing the transformed cell and recovering said protein from the cell culture.

9. The method of claim 8, wherein the step of transforming comprises introducing into said cell the vector of claim 2.

10. A method of claim 8 wherein the nucleic acid that hybridizes under stringent conditions to the complement of the nucleic acid of SEQ ID NO: 2 comprises the sequence of SEQ ID NO:2, SEQ ID NO:28 or SEQ ID NO:29.

* * * * *

UNITED STATES PATENT AND TRADEMARK OFFICE
CERTIFICATE OF CORRECTION

PATENT NO. : 6,040,437
DATED : March 21, 2000
INVENTOR(S) : Lawrence A. Lasky and Donald J. Dowbenko It is certified that error appears in the above-identified patent and that said Letters Patent is hereby corrected as shown below:

<u>Title page,</u>
Item [60], Related U.S. Application Data, change "60/104,590, Feb. 7, 1997" to -- 60/104,589, Feb. 7, 1997 --.

Signed and Sealed this

Sixteenth Day of May, 2006

JON W. DUDAS
*Director of the United States Patent and Trademark Office*